(12) United States Patent
Mascola et al.

(10) Patent No.: US 9,382,311 B2
(45) Date of Patent: Jul. 5, 2016

(54) HIV-1 BROADLY NEUTRALIZING ANTIBODIES

(71) Applicants: International AIDS Vaccine Initiative, New York, NY (US); The Scripps Research Institute, La Jolla, CA (US); THE UNITED STATES OF AMERICA, AS REPRESENTED BY THE SECRETARY, DEPARTMENT OF HEALTH AND HUMAN SERVICES, Washington, DC (US)

(72) Inventors: John Mascola, Rockville, MD (US); Dennis R. Burton, La Jolla, CA (US); Wayne Koff, Stony Brook, NY (US); Peter Kwong, Washington, DC (US); Gary Nabel, Washington, DC (US); Sanjay K. Phogat, Edison, NJ (US); Pascal Raymond Georges Poignard, San Diego, CA (US); Melissa Danielle De Jean St. Marcel Simek-Lemos, Brooklyn, NY (US); Xueling Wu, Potomac, MD (US); Tongqing Zhou, Boyds, MD (US); Zhi-Yong Yang, Potomac, MD (US)

(73) Assignees: INTERNATIONAL AIDS VACCINE INITIATIVE, New York, NY (US); THE SCRIPPS RESEARCH INSTITUTE, La Jolla, CA (US); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 13/792,098

(22) Filed: Mar. 10, 2013

(65) Prior Publication Data
US 2013/0251726 A1    Sep. 26, 2013

Related U.S. Application Data

(63) Continuation-in-part of application No. PCT/US2011/052933, filed on Sep. 23, 2011.

(60) Provisional application No. 61/515,528, filed on Aug. 5, 2011, provisional application No. 61/386,211, filed on Sep. 24, 2010.

(51) Int. Cl.
C07K 16/10    (2006.01)
A61K 39/42    (2006.01)
A61K 45/06    (2006.01)
A61K 39/00    (2006.01)

(52) U.S. Cl.
CPC ............. *C07K 16/1063* (2013.01); *A61K 39/42* (2013.01); *A61K 45/06* (2013.01); *A61K 2039/505* (2013.01); *C07K 2317/21* (2013.01); *C07K 2317/33* (2013.01); *C07K 2317/34* (2013.01); *C07K 2317/76* (2013.01)

(58) Field of Classification Search
CPC ........... C07K 16/1063; C07K 2317/76; C07K 2317/21; A61K 39/42
See application file for complete search history.

(56) References Cited

U.S. PATENT DOCUMENTS

2008/0286290 A1    11/2008    Furusako et al.

FOREIGN PATENT DOCUMENTS

WO    WO 99/01475        1/1999
WO    WO 2010/107939 A2  9/2010

OTHER PUBLICATIONS

Gallo, R. C., et al., Nov. 2005, The end or the beginning of the drive to an HIV-preventive vaccine: a view from over 20 years, The Lancet 366:1894-1898.*
Letvin, N. L., Dec. 2006, Progress and obstacles in the development of an AIDS vaccine, Nature Rev. Immunol. 6:930-939.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biolog. 35:367-371.*
Aarons, E. J., et al., 2001, Adaptation to blockade of human immunodeficiency virus type 1 entry imposed by the anti-CCR5 monoclonal antibody 2D7, Virol. 297:382-390.*
Xiang, J., et al., 1995, Framework residues 71 and 93 of the chimeric B72.3 antibody are major determinants of the conformation of heavy-chain hypervariable loops, J. Mol. Biol. 253:385-390.*
Liu, Z., et al., 1999, Fine mapping of the antigen-antibody interaction of scFv215, a recombiant antibody inhibiting RNA polymerase II from *Drosophila melanogaster*, J. Mol. Recognit. 12:103-111.*
Xueling Wu et al: "Rational design of envelope identifies broadly neutralizing human monoclonal antibodies to HIV-1", Science, American Association for the Advancement of Science, US, vol. 329, No. 5993, p. 856-861. Aug. 13, 2010.
Clapham Paul R et al: "Vaccinology: precisely tuned antibodies nab HIV.", Nature, vol. 477, No. 7365, pp. 416-417. Sep. 22, 2011.

\* cited by examiner

*Primary Examiner* — Jeffrey Parkin
(74) *Attorney, Agent, or Firm* — Vedder Price P.C.; Thomas J. Kowalski; Deborah L. Lu

(57) ABSTRACT

The present application relates broadly neutralizing monoclonal antibodies directed against HIV-1. In particular, monoclonal antibodies VRC-PG04 and VRC-PG05 are disclosed.

8 Claims, 49 Drawing Sheets

Figure 8

A. Heavy-chain

```
            -------FR1-----------    -----CDR1------    ------FR2------      ------CDR2-----------                          -----FR3----------------------------               IGHD3-16*02                        JH1*01
                                                                                                                                                                                                                 -----CDR3-----                  ----FR4----
IGHV1-02*02 QVQLVQSGAEVKKPGASVKVSCKASGYTF.TGYYMEHWVRQAPGQGLEWMGWINPNSGGTNY.AQKFQGRVTMTR.......DTSISTAYMELSRLRSDDTAVYYCAR        DYVW            AEYFQHWGQGTLVTVSS
VRC01       QVQLVQSGGQMKKPGESMRISCRASGYEF.IDCTLNWIRLAPGKRPEWMGWLKPRGGAVNY.ARPLQGRVTMTR.......DVYSDTAFLELRSLTVDDTAVYFCTRGKNCDYNW                 DFEHWGRGTPVIVSS
VRC02       QVQLVQSGGQMKKPGESMRISCQASGYEF.IDCTLNWIRLAPGRRPEWMGWLKPRGGAVNY.ARPLQGRVTMTR.......DVYSDTAFLELRSLTADDTAVYCTRGKNCDYNW                   DFEHWGRGTPVTVSS
VRC03       QVQLVQSGAVIKTPGSSVKISCRASGYNF.RDYSIHNVRLIPDKGFEWIGWIKPLWGAVSY.ARQLQGRVSMTRQLSQDPDDPWGVAYMEFSGLTPADTAEYFCVRRGSCDYCGDFPWQ                YWGQGTVVVSS
VRC-PG-04   QVQLVQSGSGVKKPGASVRVSCWTSEDIPERTELIHWVRQAPGQGLEWIGWKTVTGAVNFGSPDFRQRVSLTR.......DRDLFTAHMDIRGLTQGDTATYFCARQKFYTGGQWYFD              LWGRGTLIVSS

-------FR1-----------    -----CDR1------    ------FR2------      ------CDR2-----------                          -----FR3----------------------------                                                  -----CDR3-----                  ----FR4----
IGHV3-7*01  EVQLVESGGGLVQPGGSLRLSCAASGFTFSSYWMSWVRQAPGKGLEWVANIKQDGSEKYYVDSVKGRFTISRDNAKNSLYLQMNSLRAEDTAVYYCAR
VRC-PG-05   EVQLVESGGGLVQPGGSLRLSCAASGFPFNRDWMTWVRQAPGKGLEWVANINMDGKKDYVDSVKGRFTISRDNAKTSLYLQMNSLRAGDTAVYYCARIRQVSKYLQWYPGVFEMWGQGTMVTVSS
```

B. Light-chain

```
            -------FR1----------    ------CDR1--------    ------FR2------   ---CDB2---                     ----------FR3-----------------------               ---CDR3------         ----FR4----
                                                                                                                                                                                                           JK2*01
IGKV3-11*01 EIVLTQSPATLSLSPGERATLSCRASQSVS  SYLAWYQQKPGQAPRLLIYDASNRATGIPARFSGSGSGRDFTLTISSLEPEDFAVYYCQQRSNWP YTFGQGTK.LEIK
VRC01       EIVLTQSPGTLSLSPGETAIISCRTSQYGS..LAWYQQRPGQAPRLVIYSGSTRAAGIPDRFSGSRWGPDYNLTISNLESGDFGVYYCQQ                YEFFGQGTKVQVDIK
VRC02       EIVLTQSPGTLSLSPGETAIISCRTSQYGS..LAWYQQRPGQAPRLVIYSGSTRAAGIPDRFSGSRWGPDYNLTIRNLESGDFGLYYCQQ                YEFFGQGTKVQVDIK

-------FR1----------    ------CDR1--------    ------FR2------   ---CDB2---                     ----------FR3-----------------------               ---CDR3------         ----FR4----
IGKV3-20*01 EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP
VRC03       EIVLTQSPGTLSLSPGETATLFCKASQGGNA..MTWYQKRRGQVPRLLIYDTSRRASGVPDRFVGSGSGTDFFLLINKLDREDFAVYYCQQ              FEFFGLGSE.LEVH
VRC-PG-04   EIVLTQSPGTLSLSPGETASLSCTAASYGH..MTWYQKKPGQPPKLLIFATSKRASGIPDRFSGSQFGKQYTLTITRMEPEDFARYYCQQ              LEFFGQGTR.LEIR

-------FR1----------    ------CDR1--------    ------FR2------   ---CDB2---                     ----------FR3-----------------------               ---CDR3------         ----FR4----
IGKV4-1*01  DIVMTQSPDSLAVSLGERATINCKSSQSVLYSSNNKNYLAWYQQKPGQPPKLLIYWAS  TRESGVPDRFSGSGSGTDFTLTISSLQAEDVAVYYCQQY
VRC-PG-05   DIVMTQSPDSLAVSLGERATIHCKSSQSVLYRPNNRNVAWYQQKPGQPPRLLIHWAS  FRESGVPDRTGSGSGTDFTLTISSLQAEDVAVYYCQQYFFLYSFGGGTKLEIN
```

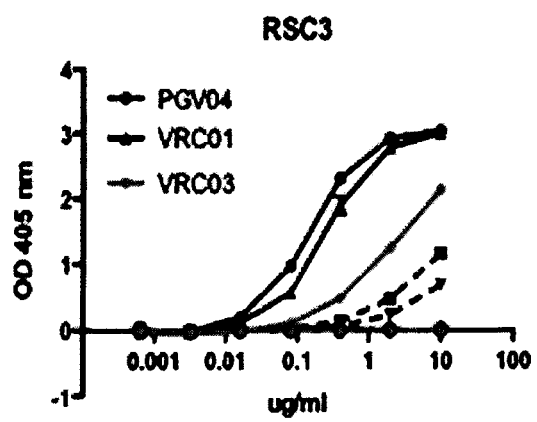
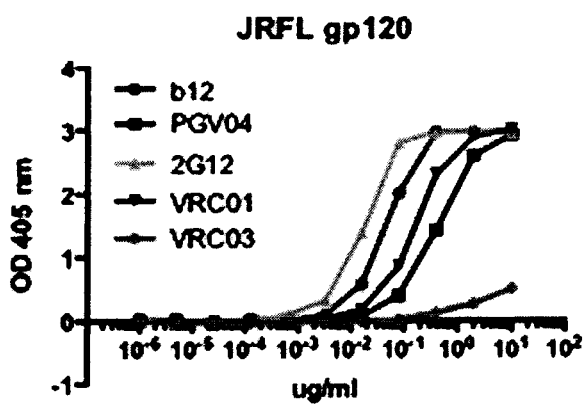
Figures 9A-B

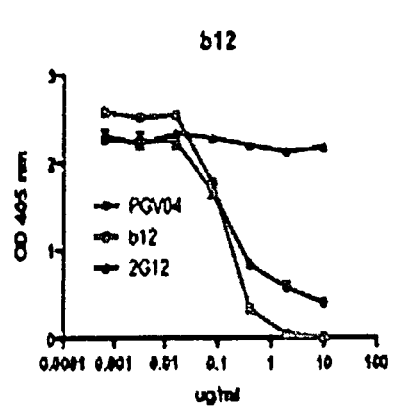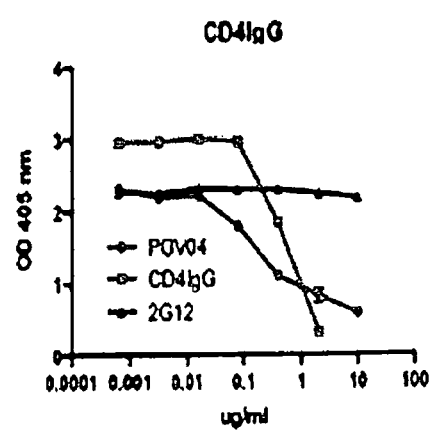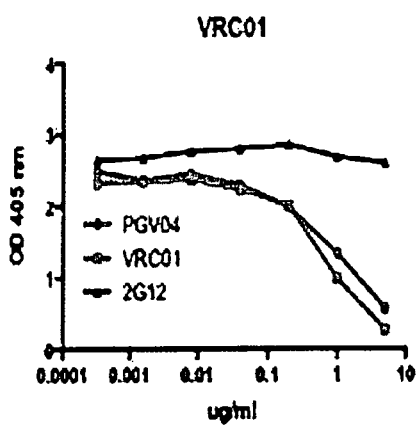
Figure 10A

B
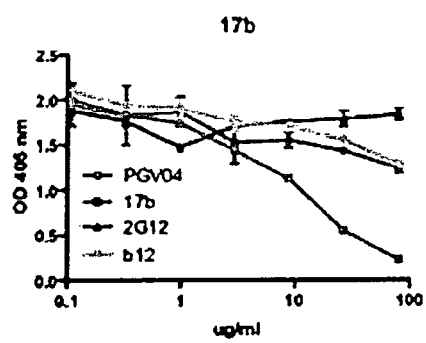
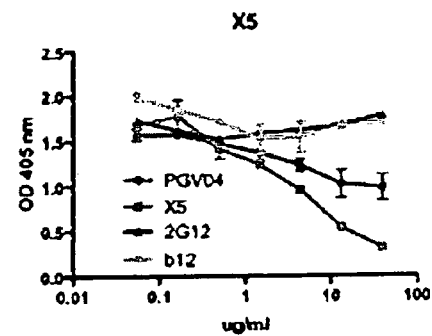
C
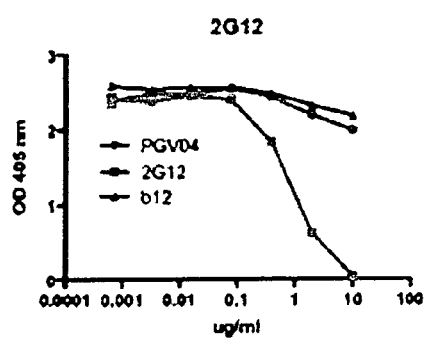
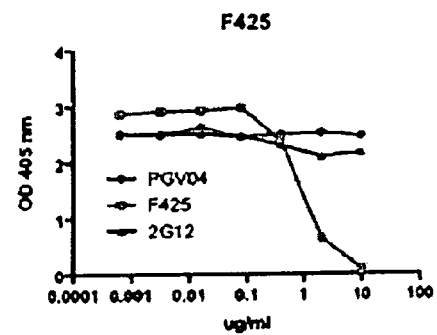
D
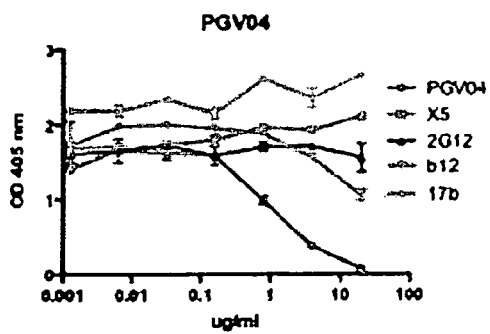
Figures 10B-D

Figure 11A-B

| A | | Median IC50 (µg/ml) against viruses neutralized with an IC50 <50µg/ml for mAbs or <100 (1/dil'n) for serum | | | | | | | |
|---|---|---|---|---|---|---|---|---|---|
| | | 162-virus panel | | | | 97-virus panel | | | |
| Clade | No. of viruses | PGV04 | PG9 | Donor #74 | | Clade | No. of viruses | PGV04 | PG9 | VRC01 |
| A | 26 | | | 469 | | A | 24 | | | |
| AE | 10 | 1.24 | | 251 | | | | | | |
| AG | 10 | | | 763 | | | | | | |
| B | 31 | | 0.96 | 617 | | B | 33 | | | |
| C | 27 | 0.79 | 0.39 | 317 | | C | 35 | 0.25 | | 0.35 |
| D | 25 | 0.44 | 0.21 | 313 | | | | | | |
| F | 15 | | | 388 | | | | | | |
| G | 15 | | 1.13 | 730 | | | | | | |
| TOTAL | 162 | 0.2 | 0.27 | 414 | | TOTAL | 97 | | | |

| B | | Percent viruses neutralized | | | | | | | |
|---|---|---|---|---|---|---|---|---|---|
| Clade | No. of viruses | PGV04 | PG9 | Donor #74 | | Clade | No. of viruses | PGV04 | PG9 | VRC01 |
| A | 26 | | 85 | 88 | | A | 24 | | | |
| AE | 10 | 90 | | 80 | | | | | | |
| AG | 10 | | 60 | 80 | | | | | | |
| B | 31 | | 71 | 84 | | B | 33 | 88 | 61 | |
| C | 27 | 70 | 74 | 70 | | C | 35 | 80 | 80 | 86 |
| D | 25 | 76 | 76 | 64 | | | | | | |
| F | 15 | | 67 | 80 | | | | | | |
| G | 15 | 87 | 80 | 80 | | | | | | |
| TOTAL | 162 | 86 | 75 | 78 | | TOTAL | 97 | 87 | 62 | 93 |

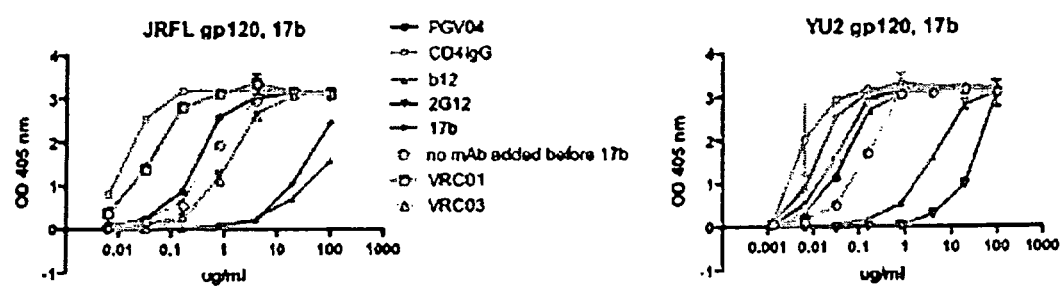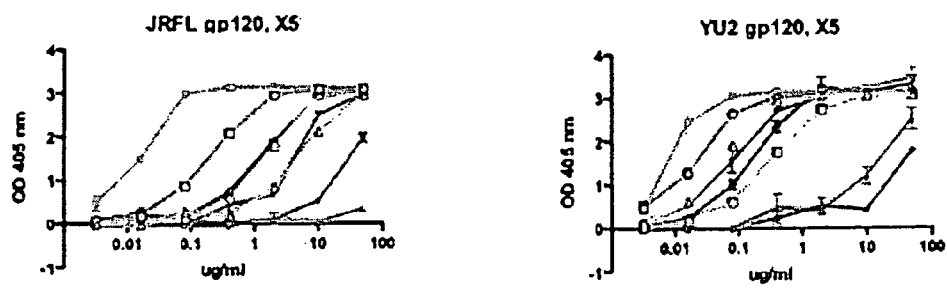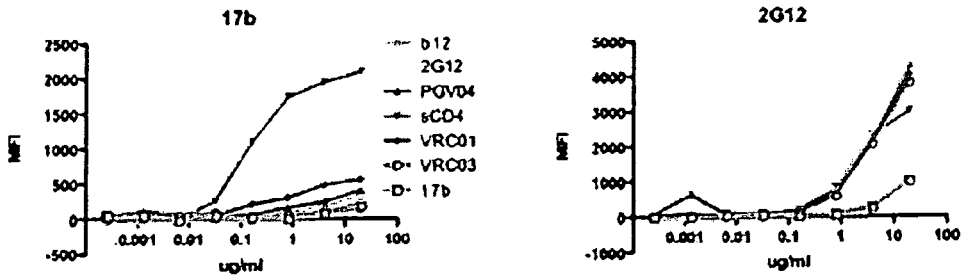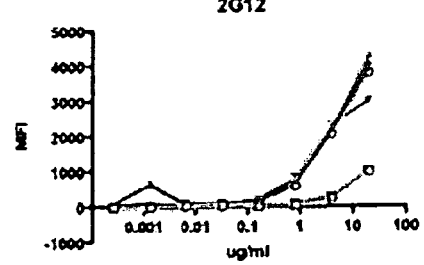
Figure 12A-D

Figure 13A

| gp120 domain | mutation | PGV04 | VRC01 | CD4-IgG | b12 |
|---|---|---|---|---|---|
| Neutralization potency relative to WT (%) | | | | | |
| C1 | E87A | 118 | | | |
| | M95A | 107 | | | |
| | K97A | 130 | | | |
| | E102A | 146 | | | |
| | W112A | 118 | | | |
| C1 (V1/V2 stem) | V120A | 84 | | | |
| | K121A | 78 | | | |
| | L122A | 106 | | | |
| | T123A | 121 | | | |
| | L125A | 89 | | | |
| | N156A | 73 | | | |
| | N160K | 176 | | | |
| V2 | T162A | 177 | | | |
| | I165A | 61 | | | |
| | R166A | 51 | | | |
| | D167A | 81 | | | |
| | K168A | 67 | | | |
| | K171A | 149 | | | |
| | E172A | 59 | | | |
| | Y177A | 135 | | | |
| | L179A | 88 | | | |
| | V182A | 68 | | | |
| | I184A | 135 | | | |
| | D185A | 120 | | | |
| | T189A | 240 | | | |
| C2 (V1/V2 stem) | K194S | 236 | | | |
| | T198A | 95 | | | |
| | S199A | >1000 | >1000 | >1000 | >1000 |
| | T202A | 61 | | | |
| C2 | F210A | 101 | | | |
| | I213A | 185 | | | |
| | R252A | 86 | | | |
| | S256A | 152 | | | |
| | T257A | 148 | | | |
| | N262A | 105 | | | |

Figure 13B

| | | | | | |
|---|---|---|---|---|---|
| | R273A | 120 | | | |
| | N276A | ▓ | 400 | 123 | 106 |
| | D279A | ▓ | ▓ | ▓ | 61 |
| | K282A | 81 | | | |
| | T283A | 225 | | | |
| V3 (base) | N295A | 97 | | | |
| | T297S | 179 | | | |
| | P299A | 84 | | | |
| | N301A | 85 | | | |
| V3 (stem) | N302A | 120 | | | |
| | R304A | 43 | | | |
| | K305A | 54 | | | |
| V3 (tip) | S306A | 130 | | | |
| | I307A | ▓ | ▓ | >1000 | >1000 |
| | H308A | 99 | | | |
| | I309A | ▓ | ▓ | >1000 | >1000 |
| | P313A | 111 | | | |
| | R315A | 92 | | | |
| | F317A | ▓ | ▓ | >1000 | >1000 |
| | Y318A | ▓ | ▓ | >1000 | >1000 |
| | T319A | 102 | | | |
| | T320A | 64 | | | |
| V3 (base) | E322A | 83 | | | |
| | D325A | 112 | | | |
| | N332A | 120 | | | |
| C3 | D337A | 172 | | | |
| | K343A | 117 | | | |
| | R350A | 106 | | | |
| | S365A | 155 | | | |
| | P369A | 113 | | | |
| | V372A | 125 | | | |
| | M373A | 135 | | | |
| | Y384A | 69 | | | |
| | N386A | 120 | | | |
| | T388A | 160 | | | |
| V4 | N392Q | 73 | | | |
| | W395A | 95 | | | |
| C4 | R419A | 111 | | | |
| | I420A | ▓ | ▓ | >1000 | 731 |

Figure 13C

| | | | | | |
|---|---|---|---|---|---|
| | K421A | 68 | | | |
| | Q422A | 98 | | | |
| | I423A | | | >1000 | >1000 |
| | I424A | 142 | | | |
| | N425A | 148 | | | |
| | V430A | 82 | | | |
| | K432A | 101 | | | |
| | Y435A | 73 | | | |
| | I439A | 88 | | | |
| | T450A | 135 | | | |
| | T455A | 142 | | | |
| | R456A | 55 | | | |
| | G459A | 239 | | | |
| | N461A | 509 | 321 | 129 | 233 |
| V5 | E462A | 116 | | | |
| | S463A | 252 | 340 | 243 | 152 |
| | G471A | 92 | | | |
| | D474A | 102 | | | |
| | M475A | 140 | | | |
| C5 | R476A | 141 | | | |
| | D477A | 107 | | | |
| | W479A | 138 | | | |
| | R480A | 113 | | | |

Figure 13D

| Apparent Binding Affinity | | | |
|---|---|---|---|
| Domain | Mutant | PGV04 | 2G12 |
| C1 | E87A | 53 | 88 |
| | M95A | 41 | 66 |
| | K97A | 98 | 103 |
| | E102A | | 47 |
| | W112A | 76 | 80 |
| | D113A | 70 | 91 |
| C1 (V1/V2-stem) | V120A | 79 | 93 |
| | K121A | 130 | 129 |
| | L122A | 96 | 83 |
| | T123A | 113 | 106 |
| | L125A | 93 | 134 |
| | V127A | | |
| | N156A | 72 | 98 |
| | N160K | 390 | 183 |
| V2 | T162A | 87 | 103 |
| | I165A | 139 | 125 |
| | R166A | 97 | 100 |
| | D167A | 97 | 90 |
| | K168A | 87 | 108 |
| | K171A | 84 | 103 |
| | E172A | 103 | 86 |
| | F176A | 104 | 102 |
| | Y177A | 120 | 131 |
| | L179A | 138 | 122 |
| | D180A | 46 | 57 |
| | V182A | 54 | 96 |
| | I184A | | 45 |
| | D185A | 55 | 78 |
| | T190A | 110 | 94 |
| C2 (V1/V2-stem) | K194S | | |
| | N197A | | 46 |
| | T198A | 49 | 81 |
| | S199A | 78 | 92 |
| | T202A | 58 | 94 |

Figure 13E

| | | | |
|---|---|---|---|
| C2 | K207A | | 201 |
| | F210A | 85 | 80 |
| | I213A | 81 | 83 |
| | R252A | 111 | 99 |
| | S256A | | |
| | T257A | 51 | 73 |
| | N262A | | 66 |
| | R273A | 78 | 78 |
| | N276A | | 102 |
| | D279A | | 107 |
| | N280A | | 38 |
| | K282A | | 80 |
| | T283A | 85 | 129 |
| V3 (base) | N295A | | |
| | T297S | 115 | 86 |
| | P299A | 115 | 99 |
| | N301A | 72 | 94 |
| V3 (stem) | N302A | 40 | 86 |
| | R304A | 44 | 88 |
| | K305A | 51 | 91 |
| V3 (tip) | S306A | 93 | 112 |
| | I307A | 67 | 126 |
| | H308A | | 98 |
| | I309A | 78 | 127 |
| | P313A | | 52 |
| | R315A | 90 | 96 |
| | F317A | 92 | 107 |
| | Y318A | 62 | 95 |
| | T319A | 52 | 88 |
| | T320A | | 84 |
| V3 (base) | E322A | | 83 |
| | D325A | 42 | 56 |
| | N332A | 68 | |

Figure 13F

| | | | |
|---|---|---|---|
| C3 | Q337A | 155 | 138 |
| | K343A | 124 | 80 |
| | R350A | 84 | 97 |
| | S365A | | 48 |
| | G366A | | 40 |
| | G367A | | 56 |
| | D368A | | 96 |
| | P369A | 70 | 112 |
| | E370A | | 84 |
| | I371A | | |
| | V372A | | 102 |
| | M373A | 77 | 106 |
| | Y384A | 42 | 105 |
| | N386A | 61 | |
| | T388A | | 70 |
| V4 | N392Q | 69 | |
| | W395A | | 7 |
| C4 | R419A | 97 | 96 |
| | I420A | 119 | 110 |
| | K421A | 69 | 97 |
| | Q422A | 78 | 103 |
| | I423A | 83 | 164 |
| | I424A | 110 | 96 |
| | N425A | 95 | 101 |
| | M426A | 67 | 107 |
| | W427A | 131 | 108 |
| | V430A | 108 | 97 |
| | K432A | 85 | 141 |
| | Y435A | 115 | 101 |
| | I439A | 118 | 109 |
| | T450A | | 40 |
| | T455A | 58 | 83 |
| | R456A | | 71 |
| | D457A | | 108 |
| | G458A | | |
| | G459A | 48 | 91 |

Figure 13G

| | | | |
|---|---|---|---|
| V5 | N461A | 264 | 144 |
| | E462A | 140 | 101 |
| | S463A | 276 | 108 |
| | I467A | | |
| | R469A | | 40 |
| | P470A | | 100 |
| | G471A | 114 | 123 |
| C5 | G472A | | 103 |
| | G473A | | 78 |
| | D474A | | 92 |
| | M475A | 75 | 93 |
| | R476A | 91 | 73 |
| | D477A | | 87 |
| | W479A | 82 | 70 |
| | R480A | 100 | 100 |
| V1-V3 | Delta V1 | | 43 |
| | Delta V1/2 | | |
| | Delta V3 | 70 | 90 |

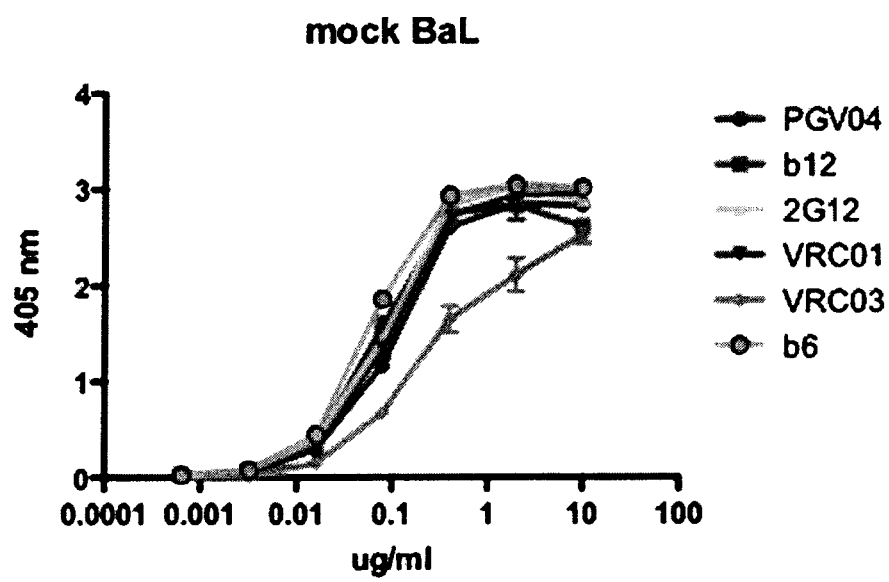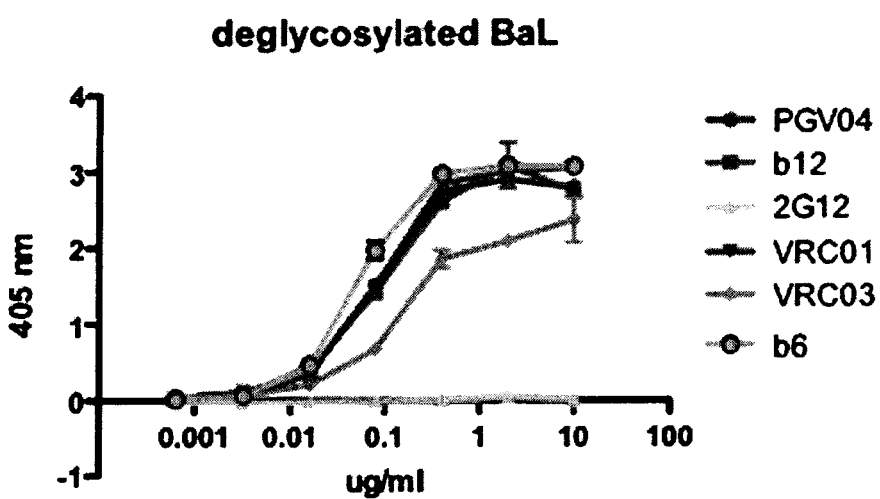
Figure 14A-B

Figure 15A

| | Subtype | IC50 (µg/mL) PGV04 | PG9( | NT50 (1/dil'n) donor serum |
|---|---|---|---|---|
| 92RW008 | A | 0.0144 | 0.0056 | 4129 |
| 92RW009 | A | 0.1083 | 0.0498 | 570 |
| 92RW020 | A | 0.0550 | 0.1410 | 1498 |
| 92RW021 | A | 0.0381 | 0.0274 | 1785 |
| 92RW024 | A | 0.3097 | 0.2578 | 256 |
| 92RW026 | A | 0.1404 | 0.1640 | 1679 |
| 92UG031 | A | 4.4631 | 3.6047 | 779 |
| 92UG037 | A | 0.1453 | 0.0136 | 469 |
| 93RW029 | A | 0.5401 | 0.6895 | 420 |
| 93UG077 | A | 0.0831 | >50 | 1827 |
| 94UG103 | A | 0.2020 | 0.3400 | 1129 |
| MGRM-A-001 | A | 6.7811 | >50 | <100 |
| MGRM-A-002 | A | 0.0926 | 0.0195 | 402 |
| MGRM-A-003 | A | 0.1278 | 1.9421 | 121 |
| MGRM-A-004 | A | 0.1750 | 0.0200 | 374 |
| MGRM-A-005 | A | 0.1336 | 0.7501 | 397 |
| MGRM-A-006 | A | 0.2440 | >50 | 376 |
| MGRM-A-007 | A | 7.2132 | 1.0608 | 213 |
| MGRM-A-008 | A | 0.5545 | >50 | <100 |
| MGRM-A-009 | A | 0.0334 | 0.0232 | 4347 |
| MGRM-A-010 | A | 0.2054 | 0.0215 | 221 |
| MGRM-A-011 | A | 0.0895 | 0.0330 | 351 |
| MGRM-A-012 | A | 0.2246 | 19.2941 | <100 |
| MGRM-A-013 | A | 0.0863 | 0.1215 | 1647 |
| MGRM-A-014 | A | 0.1715 | 1.2484 | 304 |
| VLGCA1 | A | 0.0244 | 0.0692 | 824 |
| 94KE105 | AC | 2.9806 | 37.8750 | 359 |
| 92TH021 | AE | 1.2885 | 0.0586 | 268 |
| CMU02 | AE | 1.2375 | >50 | 268 |
| MGRM-AE-001 | AE | 0.0631 | 20.5858 | 272 |
| MGRM-AE-002 | AE | 0.5686 | 0.0404 | 216 |
| MGRM-AE-003 | AE | 6.4007 | 0.0442 | 142 |
| MGRM-AE-004 | AE | 0.1825 | 0.0086 | 235 |
| MGRM-AE-005 | AE | 0.0508 | 0.2820 | 942 |
| MGRM-AE-006 | AE | >50 | 0.0627 | <100 |
| MGRM-AE-007 | AE | 5.7528 | 0.1800 | <100 |

Figure 15B

| | | | | |
|---|---|---|---|---|
| MGRM-AE-008 | AE | 1.5134 | 31.4817 | 137 |
| MGRM-AG-001 | AG | 0.2177 | 17.1248 | 292 |
| MGRM-AG-002 | AG | 0.8794 | 0.0760 | <100 |
| MGRM-AG-003 | AG | 0.0577 | >50 | 856 |
| MGRM-AG-005 | AG | 0.0270 | >50 | 912 |
| MGRM-AG-006 | AG | 1.2296 | >50 | 800 |
| MGRM-AG-008 | AG | 2.4839 | 0.0134 | 180 |
| MGRM-AG-009 | AG | 0.1476 | >50 | <100 |
| MGRM-AG-011 | AG | 0.0714 | 0.0068 | 386 |
| MGRM-AG-012 | AG | 0.0398 | 22.8451 | 725 |
| MGRM-AG-013 | AG | 0.0298 | 0.2589 | 2374 |
| 6535.3 | B | 0.7572 | 1.0528 | 525 |
| 92BR020 | B | 0.2502 | >50 | 650 |
| 93TH305 | B | 0.2549 | 8.1239 | 375 |
| APV_13 | B | 1.2266 | >50 | 341 |
| APV_17 | B | 0.3085 | 34.7782 | 237 |
| APV_6 | B | 24.1871 | 0.1805 | 224 |
| CAAN.A2 | B | 2.2618 | 19.2666 | 811 |
| JRFL | B | 0.0319 | >50 | 2450 |
| MGRM-Chronic-B-001 | B | 0.0478 | >50 | 918 |
| MGRM-Chronic-B-002 | B | 0.1424 | 3.4389 | 453 |
| MGRM-Chronic-B-003 | B | 0.2575 | >50 | 1354 |
| MGRM-Chronic-B-004 | B | 0.0466 | 0.5326 | 755 |
| MGRM-Chronic-B-008 | B | 0.1661 | 8.7835 | 186 |
| MGRM-Chronic-B-010 | B | 0.7440 | 0.0044 | 342 |
| MGRM-Chronic-B-011 | B | 0.4972 | >50 | 765 |
| MGRM-Chronic-B-012 | B | >50 | 0.1997 | 123 |
| MGRM-Chronic-B-017 | B | 0.1287 | 0.6878 | 841 |
| MGRM-Chronic-B-018 | B | 0.1642 | 0.2161 | 557 |
| MGRM-Chronic-B-020 | B | 1.2617 | >50 | <100 |
| MGRM-Chronic-B-023 | B | 0.1392 | 0.0266 | 157 |
| MGRM-Chronic-B-024 | B | 2.5174 | 0.2224 | <100 |
| PVO.4 | B | 0.4542 | 24.7517 | 444 |
| QH0692.42 | B | 1.9042 | >50 | 205 |
| SC422661.8 | B | 0.1097 | 1.4772 | 600 |
| SF162 | B | 0.0281 | >50 | 1333 |
| THR0.18 | B | >50 | 26.3785 | <100 |
| TRJ04551.58 | B | 0.0282 | 0.8577 | 502 |
| TRO.11 | B | 0.1211 | 16.8652 | 985 |
| VLGCB3 | B | 0.0446 | 0.0222 | 1030 |

Figure 15C

| | | | | |
|---|---|---|---|---|
| 93IN905 | C | 0.3322 | 0.0345 | 914 |
| 93MW959 | C | >50 | 0.0539 | 345 |
| 97ZA012 | C | 0.0406 | 3.3999 | 1600 |
| 98IN022 | C | 5.6925 | 0.0031 | 336 |
| MGRM-C-001 | C | >50 | >50 | <100 |
| MGRM-C-002 | C | >50 | >50 | 508 |
| MGRM-C-004 | C | 0.8992 | 2.0106 | 113 |
| MGRM-C-005 | C | 23.8979 | 8.7420 | <100 |
| MGRM-C-006 | C | >50 | 0.4269 | <100 |
| MGRM-C-007 | C | >50 | 0.0637 | 220 |
| MGRM-C-008 | C | 0.7905 | >50 | 109 |
| MGRM-C-009 | C | 1.0421 | >50 | 118 |
| MGRM-C-010 | C | 0.2986 | >50 | 220 |
| MGRM-C-012 | C | 0.0253 | 0.6100 | 402 |
| MGRM-C-013 | C | >50 | >50 | <100 |
| MGRM-C-014 | C | 21.1904 | 1.0994 | 189 |
| MGRM-C-015 | C | 0.9829 | 0.4271 | 137 |
| MGRM-C-017 | C | 0.3825 | 2.6881 | 298 |
| MGRM-C-019 | C | 9.6316 | 0.0053 | <100 |
| MGRM-C-020 | C | 0.1120 | >50 | 107 |
| MGRM-C-022 | C | 18.2830 | 0.3457 | <100 |
| MGRM-C-023 | C | 0.1278 | 0.6139 | 435 |
| MGRM-C-024 | C | >50 | 0.2265 | <100 |
| MGRM-C-025 | C | >50 | 0.1483 | <100 |
| MGRM-C-026 | C | 0.3029 | 0.0596 | 1799 |
| MGRM-C-027 | C | 2.7624 | 5.3577 | 533 |
| MGRM-C-028 | C | 0.1489 | 0.0667 | 208 |
| 98CN009 | CRF07_BC | 0.1248 | 0.3709 | 929 |
| 98CN006 | CRF08_BC | 1.3196 | >50 | 115 |
| 92UG001 | D | 0.5529 | >50 | 347 |
| 92UG005 | D | 0.4398 | >50 | 196 |
| 92UG024 | D | 0.2014 | 1.8614 | 437 |
| 92UG046 | D | 22.3618 | 1.8610 | 249 |
| 94UG114 | D | 0.4611 | 40.6083 | 756 |
| MGRM-D-001 | D | >50 | >50 | <100 |
| MGRM-D-002 | D | 0.3221 | 0.0205 | 232 |
| MGRM-D-003 | D | >50 | 0.0326 | 171 |
| MGRM-D-004 | D | 43.1998 | 0.0604 | <100 |
| MGRM-D-005 | D | >50 | 1.8016 | <100 |

Figure 15D

| | | | | |
|---|---|---|---|---|
| MGRM-D-008 | D | 3.5638 | 11.4537 | 104 |
| MGRM-D-011 | D | 0.0251 | 0.0707 | 1064 |
| MGRM-D-012 | D | 0.1248 | 16.1817 | 313 |
| MGRM-D-013 | D | 0.0878 | 0.2102 | 462 |
| MGRM-D-014 | D | 0.1944 | 0.0232 | 398 |
| MGRM-D-016 | D | 0.2013 | 0.0979 | 198 |
| MGRM-D-018 | D | 17.5284 | 0.0250 | <100 |
| MGRM-D-019 | D | 0.3503 | 0.0375 | 475 |
| MGRM-D-020 | D | 0.0974 | 1.6647 | 207 |
| MGRM-D-021 | D | >50 | >50 | <100 |
| MGRM-D-022 | D | >50 | >50 | <100 |
| MGRM-D-024 | D | >50 | 0.0384 | <100 |
| MGRM-D-026 | D | 1.7611 | 23.6635 | 313 |
| MGRM-D-028 | D | 1.0079 | 20.2338 | <100 |
| MGRM-D-029 | D | 1.5567 | >50 | <100 |
| MGRM-F1-004 | F | 0.5799 | 0.1752 | 235 |
| MGRM-F1-006 | F | >50 | 7.2494 | <100 |
| MGRM-F1-008 | F | 1.0312 | >50 | 227 |
| MGRM-F1-010 | F | 0.1836 | 0.0120 | 370 |
| MGRM-F1-012 | F | 0.2497 | 0.0232 | 297 |
| MGRM-F1-013 | F | 0.0840 | 1.2533 | 834 |
| MGRM-F1-014 | F | 0.0196 | 0.0199 | 407 |
| MGRM-F1-015 | F | 0.1789 | >50 | 217 |
| MGRM-F1-016 | F | 0.2678 | 0.5175 | <100 |
| MGRM-F1-017 | F | 2.3826 | >50 | 122 |
| MGRM-F1-018 | F | 0.0269 | 0.0189 | 1252 |
| MGRM-F1-020 | F | 5.9865 | 6.3957 | <100 |
| MGRM-F1-021 | F | 0.0313 | >50 | 968 |
| MGRM-F1-022 | F | 0.0718 | 0.0275 | 1024 |
| MGRM-F1-023 | F | 0.1711 | >50 | 547 |
| MGRM-G-001 | G | >50 | 0.1663 | 336 |
| MGRM-G-004 | G | >50 | >50 | <100 |
| MGRM-G-006 | G | 0.0834 | 1.9826 | 709 |
| MGRM-G-009 | G | 0.0433 | 10.7039 | 421 |
| MGRM-G-011 | G | 0.7802 | 0.3352 | 853 |
| MGRM-G-013 | G | 0.1684 | >50 | 303 |
| MGRM-G-014 | G | 0.0559 | 16.4784 | 1404 |
| MGRM-G-015 | G | 0.3333 | 6.5988 | <100 |
| MGRM-G-016 | G | 0.0188 | 1.3634 | 960 |
| MGRM-G-017 | G | 0.0645 | 0.1035 | 1685 |

Figure 15E

| | | | | |
|---|---|---|---|---|
| MGRM-G-019 | G | 0.0267 | 14.5587 | 751 |
| MGRM-G-024 | G | 0.0332 | 0.1633 | 829 |
| MGRM-G-025 | G | 1.6079 | >50 | <100 |
| MGRM-G-027 | G | 0.1251 | 0.0065 | 190 |
| MGRM-G-028 | G | 0.3524 | 0.8910 | 387 |
| NL43 | | 0.0434 | >50 | 1589 |
| NL43 | | 0.0451 | 34.6465 | 1628 |
| NL43 | | 0.0309 | 11.1569 | 1630 |
| NL43 | | 0.0240 | 19.2334 | 1928 |
| NL43 | | 0.0310 | 9.7351 | 2083 |
| NL43 | | 0.0304 | 7.9936 | 1663 |
| NL43 | | 0.0269 | 3.3719 | 2137 |
| NL43 | | 0.0284 | 4.6467 | 1836 |
| NL43 | | 0.0335 | 18.7168 | 2079 |
| NL43 | | 0.0278 | 12.6701 | 1927 |
| JRCSF | | 0.0782 | 0.0027 | 632 |
| JRCSF | | 0.0806 | 0.0035 | 689 |
| JRCSF | | 0.0634 | 0.0030 | 592 |
| JRCSF | | 0.0658 | 0.0030 | 468 |
| JRCSF | | 0.0542 | 0.0030 | 577 |
| JRCSF | | 0.0520 | 0.0031 | 541 |
| JRCSF | | 0.0574 | 0.0025 | 671 |
| JRCSF | | 0.0479 | 0.0028 | 704 |
| JRCSF | | 0.0464 | 0.0028 | 782 |
| JRCSF | | 0.0764 | 0.0018 | 680 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |
| aMLV | | >50 | >50 | <100 |

Figure 15F

| | | IC$_{50}$ values (µg/ml) | | |
|---|---|---|---|---|
| | | VRC01 IgG | PGV04 | PG9 IgG |
| Tier 1 clade B (n=7) | HXB2 | 0.034 | 0.025 | 1.62 |
| | MN.3 | 0.022 | >50 | >50 |
| | SF162 | 0.139 | 0.024 | >50 |
| | ADA | 0.379 | 0.179 | 0.128 |
| | BaL.01 | 0.055 | 0.034 | 0.033 |
| | BaL.26 | 0.048 | 0.148 | 0.019 |
| | SS1196.1 | 0.170 | 0.189 | 0.074 |
| Tier 1 clade C | MW965.26 | 0.056 | 0.032 | 2.17 |
| Clade A (n=24) | RW020.2 | 0.224 | 0.165 | 0.052 |
| | UG037.8 | 0.079 | 0.109 | 0.020 |
| | DJ263.8 | 0.080 | 0.80285 | 0.218 |
| | KER2018.11 | 0.652 | 1.08 | 0.010 |
| | Q259.w6 | 0.170 | 0.028 | 1.17 |
| | Q769.h5 | 0.084 | 0.024 | 0.009 |
| | Q168.a2 | 0.115 | 0.032 | 0.045 |
| | Q23.17 | 0.085 | 0.084 | 0.005 |
| | Q259.17 | 0.066 | >50 | 0.041 |
| | Q461.e2 | 0.492 | 0.237 | 1.47 |
| | Q842.d12 | 0.030 | 0.017 | 0.019 |
| | BB201.B42 | 0.223 | 0.081 | 0.011 |
| | MB201.A1 | 0.165 | 0.049 | 0.054 |
| | MB201.B10 | 0.132 | 0.042 | 0.052 |
| | BB539.2B13 | 0.069 | 0.398 | 0.063 |
| | MB539.2D1 | 0.060 | 0.499 | 0.035 |
| | MB539.2B7 | 0.531 | 0.462 | 0.094 |
| | BI369.9A | 0.142 | 0.039 | 0.023 |
| | MI369.A5 | 0.107 | 0.046 | 0.035 |
| | BS208.B1 | 0.019 | 0.014 | 0.016 |
| | MS208.A1 | 0.101 | 0.055 | 0.032 |
| | MS208.A3 | 0.050 | 0.022 | 0.025 |

Figure 15G

|  | KER2008.12 | 0.379 | 0.236 | 0.017 |
|---|---|---|---|---|
|  | KNH1209.18 | 0.087 | 0.0579 | 0.167 |
| Tier 2 clade B (n=26) | JRCSF.JB | 0.093 | 0.034 | 0.002 |
|  | JRFL | 0.031 | 0.063 | >50 |
|  | YU2 | 0.126 | 0.084 | 1.73 |
|  | 89.6 | 0.511 | 0.061 | >50 |
|  | 6101.10 | 0.111 | 0.090 | >50 |
|  | 7165.18 | ▓ | >50 | >50 |
|  | 6535.3 | 0.539 | 0.687 | 0.222 |
|  | QH0692.42 | 1.5 | 1.34 | >50 |
|  | SC422661.8 | 0.076 | 0.038 | 0.325 |
|  | PVO.4 | 0.216 | 0.235 | 8.7 |
|  | TRO.11 | 0.207 | 0.131 | >50 |
|  | AC10.0.29 | 2.2 | ▓ | 0.012 |
|  | RHPA4259.7 | 0.060 | 0.038 | 10 |
|  | THRO4156.18 | 2.25 | >50 | ▓ |
|  | REJO4541.67 | 0.062 | 0.019 | 0.001 |
|  | TRJO4551.58 | 0.083 | 0.069 | 1.85 |
|  | WITO4160.33 | 0.148 | 0.080 | 0.005 |
|  | CAAN5342.A2 | 0.824 | 1.13 | ▓ |
|  | BL01.DG | >50 | >50 | >50 |
|  | BR07.DG | 1.24 | 0.789 | >50 |
|  | HT593.1 | 0.334 | 0.177 | 0.214 |
|  | R2 | 0.198 | 0.291 | >50 |
|  | BG1168.01 | 0.276 | 0.509 | >50 |
|  | QH0515.01 | 0.386 | 0.115 | >50 |
|  | 5768.04 | 0.166 | 0.042 | 0.031 |
|  | 3988.25 | 0.220 | 0.295 | 0.016 |
| Tier 2 clade C (n=34) | Du123.6 | ▓ | >50 | 0.047 |
|  | Du151.2 | 3.16 | 0.059 | 0.012 |
|  | Du156.12 | 0.089 | 0.034 | 0.035 |
|  | Du172.17 | >50 | 0.314 | 0.240 |

Figure 15H

|  | | | | |
|---|---|---|---|---|
|  | Du422.1 | >50 | >50 | 0.178 |
|  | ZM197M.PB7 | 0.36 | 1.14 | 0.287 |
|  | ZM214M.PL15 | 0.44 | 0.249 | >50 |
|  | ZM233M.PB6 | 1.99 | 7.67 | 0.001 |
|  | ZM249M.PL1 | 0.048 | 0.051 | 0.023 |
|  | ZM53M.PB12 | 1.31 | 1.51 | 0.092 |
|  | ZM109F.PB4 | 0.128 | 0.047 | 0.235 |
|  | ZM135M.PL10a | 0.346 |  | >50 |
|  | CAP45.2.00.G3 | 2.29 | >50 | 0.003 |
|  | CAP210.2.00.E8 | >50 | >50 | 0.08 |
|  | CAP244.2.00.D3 | 0.428 | 0.301 | 0.082 |
|  | ZA012.29 | 0.305 | 0.130 | 4.59 |
|  | BR025.9 | 0.115 | 2.77 | 0.018 |
|  | TV1.29 | >50 | >50 | 0.007 |
|  | ZM215.8 | 0.095 | 0.075 | 0.025 |
|  | ZM106.9 | 0.489 | 0.206 | 4.59 |
|  | ZM55.28a | 0.340 | 0.390 | 4.60 |
|  | ZM53.21 | 1.16 | 1.15 | 0.019 |
|  | ZM55.4a | 0.450 | 0.457 | 4.19 |
|  | ZM106.10 | 0.566 | 0.1252 | 0.097 |
|  | ZM109.32 | 0.091 | 0.055 | 0.099 |
|  | ZM135.8a | 0.374 | >50 | >50 |
|  | ZM146.7 | 0.333 | 0.403 | 0.181 |
|  | ZM176.66 | 0.055 | 0.140 | 0.011 |
|  | ZM181.6 | 1.12 |  | 0.005 |
|  | SO18.18 | 0.069 | 0.067 | 0.031 |
|  | 286.36 | 0.188 | 0.090 | 0.084 |
|  | 288.38 | 0.992 | 0.390 | 0.610 |
|  | TZA125.17 | >50 | >50 | 0.115 |
|  | TZBD.02 | 0.109 | 0.067 | 0.211 |
| Clade D | UG024.2 | 0.156 | 0.199 | 3.23 |
|  | 57128.02 | >50 | >50 | 0.136 |

Figure 15I

| clade E | TH966.8 | 0.334 | 0.068 | 0.020 |
|---|---|---|---|---|
| | TH976.17 | 0.087 | 0.046 | >50 |
| | M02138 | 0.348 | 0.219 | 0.189 |
| Non-HIV | SIVmac251.30 | >50 | >50 | >50 |
| | MuLV | >50 | >50 | >50 |
| HIV-2 | 7312A.V434M | >50 | | |
| | 7312A.V434M+sCD4 | >50 | | |
| | 7312A.C1.Y720S | >50 | | |
| | 7312A.Y720S | >50 | | |

Figure 17 A-B
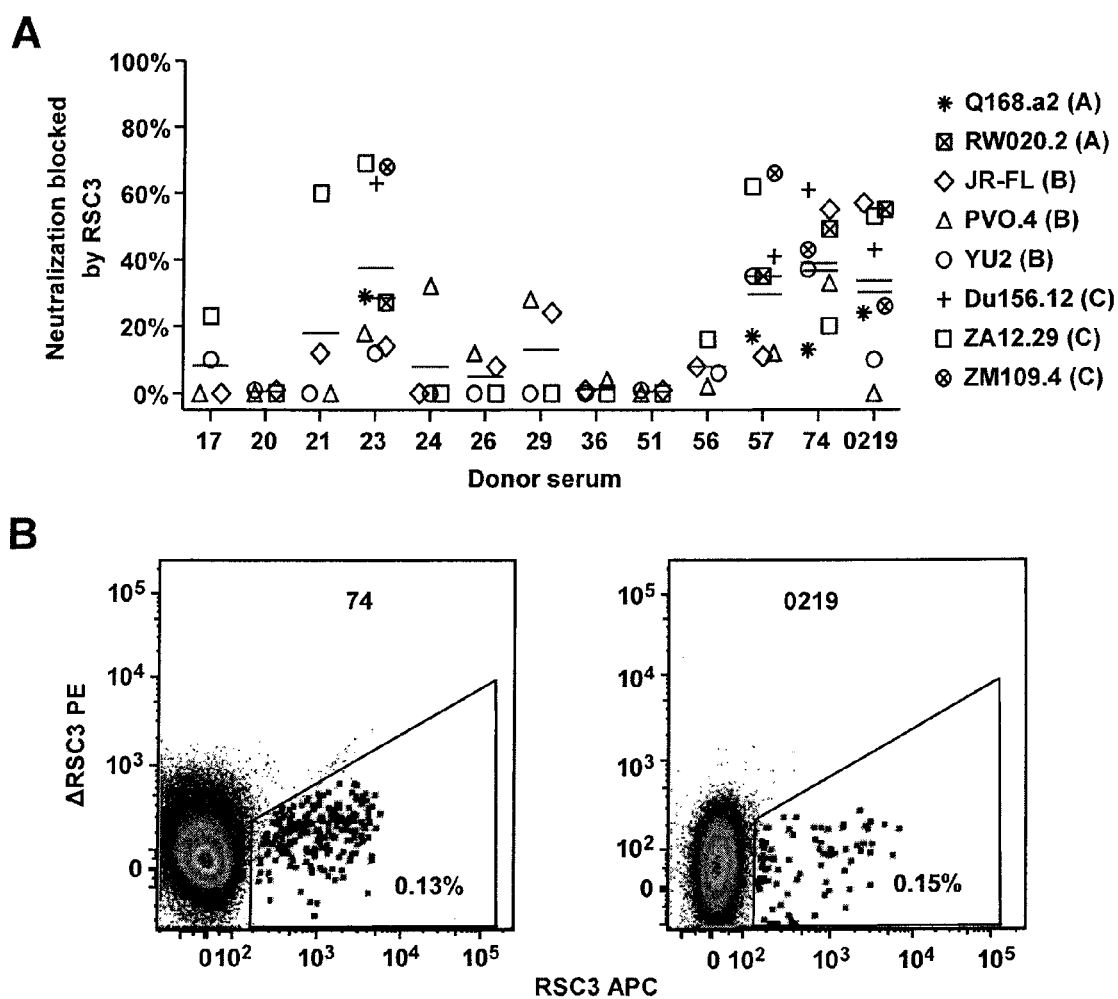

Figure 17C

```
Heavy chain   ------FR1------              CDR1            ----FR2----              CDR2              -----FR3-----                              CDR3              ----FR4----
IGHV1-02*02   QVQLVQSGAEVKKPGASVKVSCKASGYTFTG.........YYMHWVRQAPGQGLEWMGWINPNSGGTNY.AQKFQGRVTMTR........DTSISTAYMELSRLRSDDTAVYYCAR
VRC01         QVQLVQSGGQMKKPGESMRISCRASGYEFID.........CTLNWIRLAPGKRPEWMGWLKPRGGAVNY.ARPLQGRVTMTR........DVYSDTAFLELRSLITVDDTAVYFCTRGKNCDYNWDF..EHWGRGTPVIVSS
VRC02         QVQLVQSGGQMKKPGESMRISCQASGYEFID.........CTLNWIRLAPGRRPEWMGWLKPRGGAVNY.ARPLQGRVTMTR........DVYSDTAFLELRSLITADDTAVYYCTRGKNCDYNWDF..EHWGRGTPVTVSS
VRC03         QVQLVQSGAVIKTPGSSVKISCRASGYNFRD.........YSIHWVRLIPDKGFEWIGWIKPLWGAVSY.ARQLQGRVSMTRQLSQDPDDPWGVAYMEFSGLITPADTAEYTCVRRGSCDYCGDFFWQYWGQGTVVVSS
VRC-PG04      QVQLVQSGSGVKKPGASVRVSCWTSEDIFER.........TELIHWVRQAPGQGLEWIGWVKIVTGAVNFGSPDFRQRVSLTR........DRDLFTAHMDIRGLTQGDTATYFCARQKFVTGGQGWYEFDLMWGRGTLIVVSS
VRC-PG04b     QVQLVQSGSGVKKPGASVRVSCWTSEDIFER.........TELIHWVRQAPGQGLEWIGWVKIVTGAVNFGSPNFRHRVSLTR........DRDLFTAHMDIRGLTQGDTATYFCARQKFERGGQGWYFDLMWGRGTLIVVSS
VRC-CH30      QVQLVQSGAAVRKPGASVTVSCKFAEDDDYSPHWVNPAPEHYIHFLRQAPGQQLEWLAWMNPTNGAVNY.AWQLHGRLTATR........DGSMTTAFLEVRSLRSDDTAVYYCARAQ.KRGRSEWAYAHWGQGTPVAVSS
VRC-CH31      QVQLVQSGAAVRKPGASVTVSCKFAEDDDYSPWVNPAPEHFIHFLRQAPGQQLEWLAWMNPTNGAVNY.AWYLNGRVTATR........DRSMTTAFLEVKSLRSDDTAVYYCARAQ.KRGRSEWAYAHWGQGTPVVVSS
VRC-CH32      QVQLVQSGAAVRKPGASVTVSCKFAEDDDFSPHWVNPAPEHYIHFLRQAPGQQLEWLAWMKPTNGAVNY.AWOLQGRVTVTR........DRSQTTAFLEVKNLRSDDTAVYYCARAQ.KRGRSEWAYAHWGQGTPVISA
VRC-CH33      QVQLVQSGAAVRKPGASISVSCKFADADDYSPHWMNPAPEHYIHFLRQAPGQQLEWLAWMNPTNGAVNY.AWYLNGRVTATR........DRSMTTAFLEVRSLRSDDTAVYYCARAQ.KRARSEWAYAHWGQGTPVVVSS
VRC-CH34      QVQLVQSGAAVRKPGASVTVSCKFAEDDDWSPHWVNPAPEHYIHFLRQAPGQQLEWLAWMNPTNGAVNY.AWQLNGRLTATR........DTSMTTAFLEVKSLRSDDTAVYYCARAQ.KRGRSEWAYAHWGQGTPVVVSS Light chain   ------FR1------              CDR1            ----FR2----              CDR2              -----FR3-----                              CDR3              ----FR4----
IGKV3-11*01   EIVLTQSPATLSLSPGERATLSCRASQSVS  SYLAWYQQKPGQAPRLLIYDASNRATGIPARFSGSGSGRDFTLTISSLEPEDFAVYYCQQ
VRC01         EIVLTQSPGTLSLSPGETAIISCRTSQYGS  ..LAWYQQRPGQAPRLVIYSGSTRAAGIPDRFSGSRWGPDYNLTISNLESGDFGVYYCQQYEFFGQGTKVQVDIK
VRC02         EIVLTQSPGTLSLSPGETAIISCRTSQYGS  ..LAWYQQRPGQAPRLVIYSGSTRAAGIPDRFSGSRWGPDYNLTIRNLESGDFGLYYCQQYEFFGQGTKVQVDIK
IGKV3-20*01   EIVLTQSPGTLSLSPGERATLSCRASQSVSSYLAWYQQKPGQAPRLLIYGASSRATGIPDRFSGSGSGTDFTLTISRLEPEDFAVYYCQQ
VRC03         EIVLTQSPGILSLSPGETATLFCKASQGGNA..MTWYQKRRGQVPRLLIYDTSRRASGVPDRFVGSSGTDFFLTINKLDREDFAVYYCQQFEFFGLGSE..LEVH
VRC-PG04      EIVLTQSPGTLSLSPGETASLSCTAASYGH..MTWYQKKPGQPPKLLIFATSKRASGIPDRFSGSOFGKQYTLTITRMEPEDFARXYCCQLEFFGQGTR..LEIR
VRC-PG04b     EIVLTQSPGTLSLSPGETASLSCTAASYGH..MTWYQKKPGQPPKLLIFATSKRASGIPDRFSGSOFGKQYTLTITRMEPEDFAGYYCQQVEFFGQGTR..LEIR
IGKV1-33*01   DIQMTQSPSSLSASVGDRVTITCQASQDISNY  LNWYQQKPGKAPKLLIYDASNLETGVPSRFSGSGSGTDFTFTISSLQPEDIATYYCQQ
VRC-CH30      DIQMTQSPSSLSASLGDRVTITCQASRGIGKD  LNWYQQKPGKAPKLLVSDASILEGGVPSRFSGSGFHQNFSLTISSLQPEDVATYFCQQYETFGQGTK..VDIK
VRC-CH31      DIQMTQSPSSLSASLGDRVTITCQASRGIGKD  LNWYQQKPGKAGKAPKLLVSDASILEGGVPSRFSGSGFHQNFSLTISSLQAEDVATYFCQQYETFGQGTK..VDIK
VRC-CH32      DIQMTQSPSSLSASLGDRVTITCQASRGIGKD  LNWYQQKPGRAPLLVSDASILEGGVPTRFSGSGFHQNFSLTISSLQAEDVATYFCQQYETFGQGTK..VDIK
VRC-CH33      DIQMTQSPSSLSASLGDRVTITCQASRGIGKD  LNWYQQKRGRAPRLLVSDASVLEGGVPSRFSGSGFHQNFSLTISTLQPEDVATYFCQQYETFGQGTK..VDIK
VRC-CH34      DIQMTQSPSSLSASLGDRVTITCQASRGIGKD  LNWYQQKAGKAGKAPKLLVSDASILEGGVPSRFSGSGFHQNFSLTISSLQPEDVATYFCQQYETFGQGTK..VDIK
```

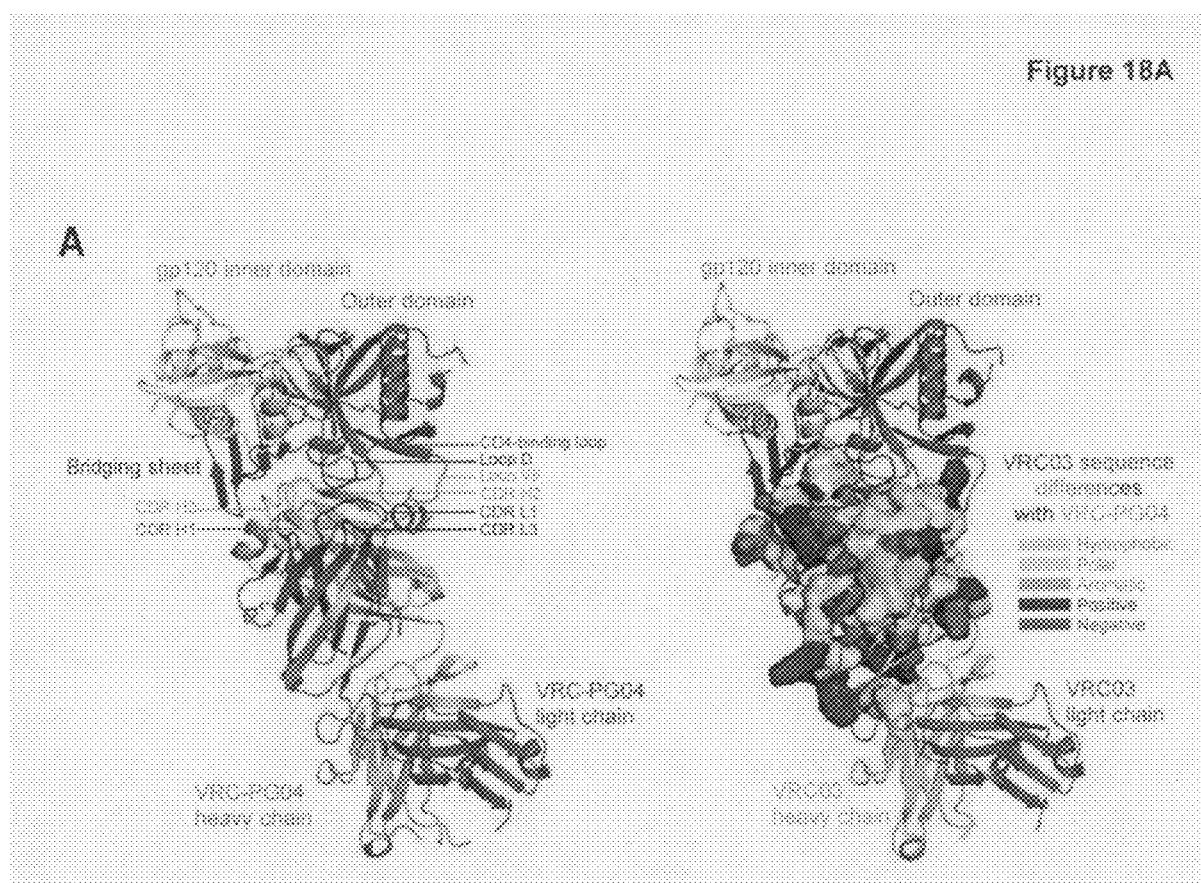

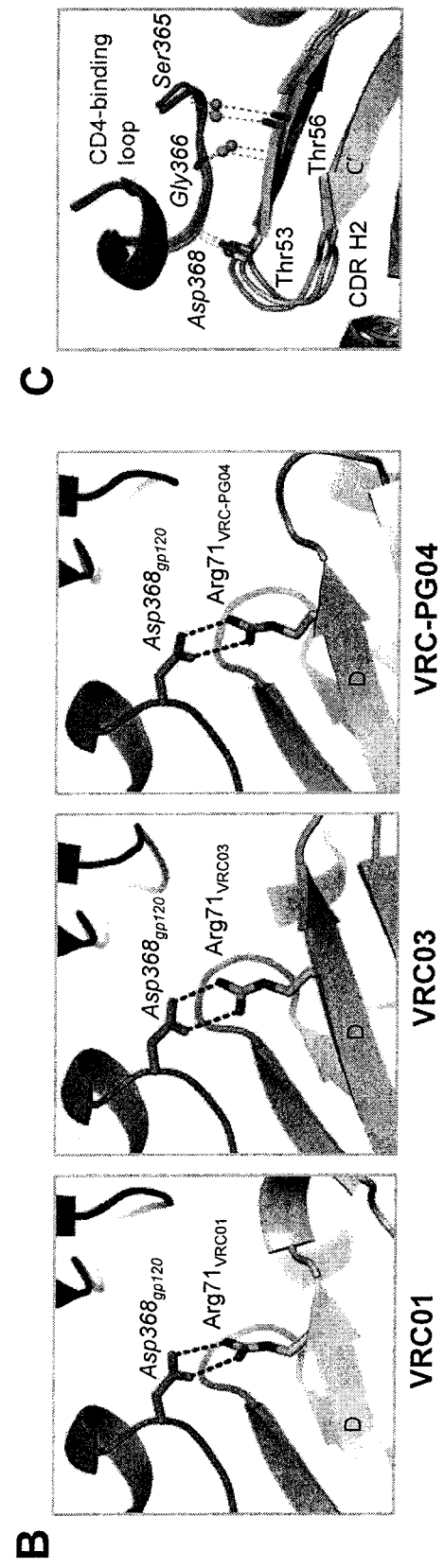
Figure 18 B-C

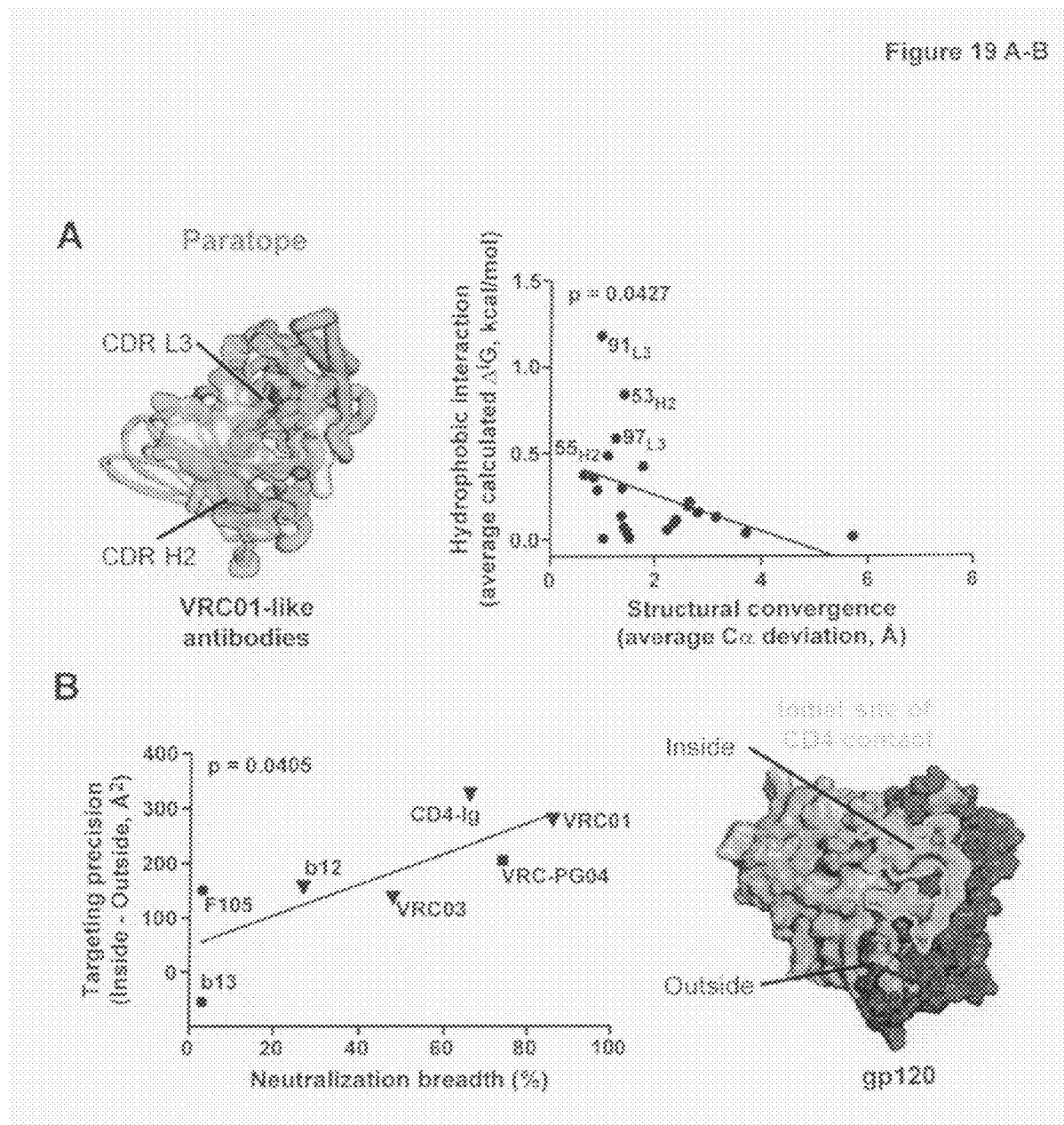
Figure 19 A-B

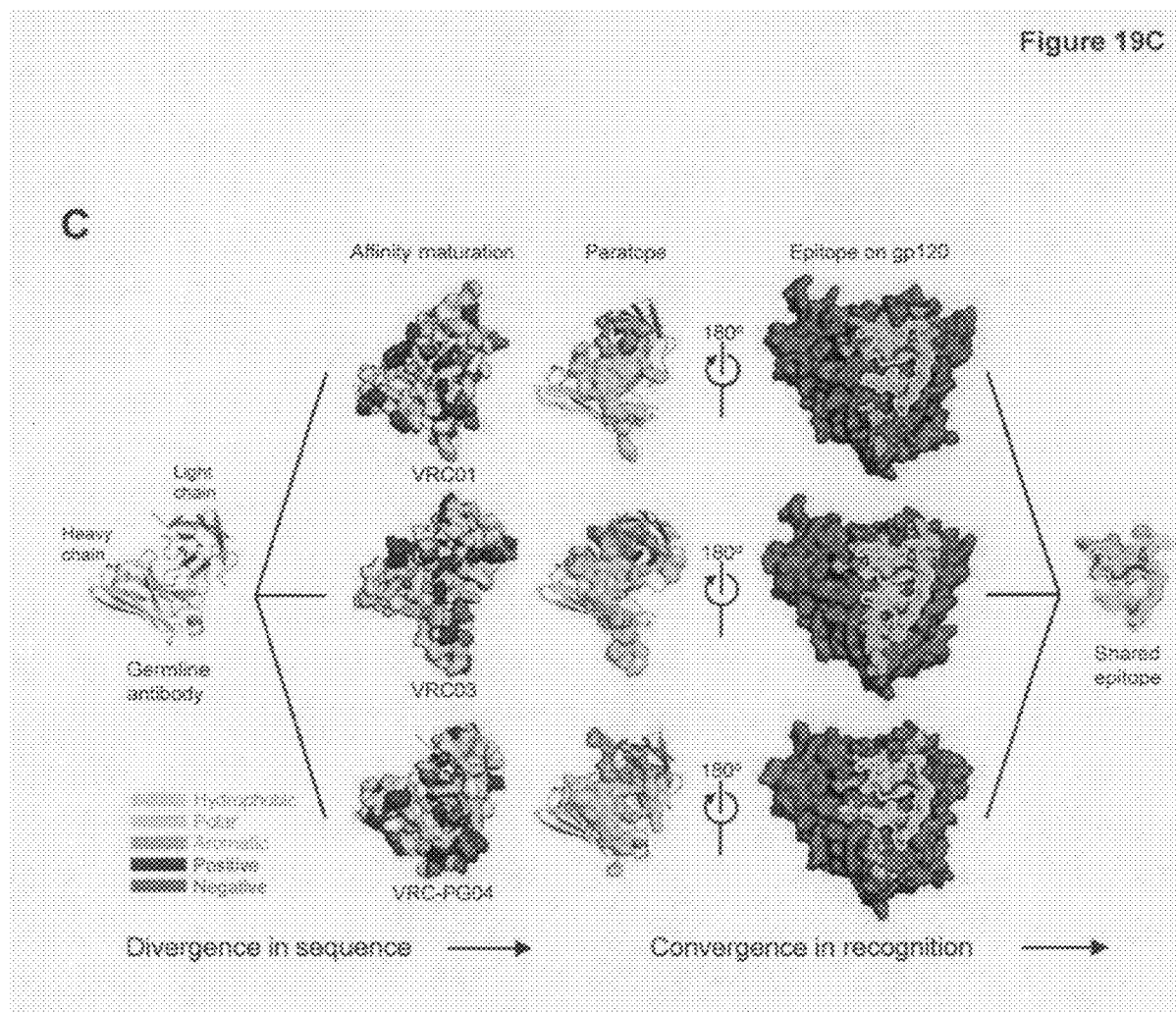

Figure 20 C-D
C Light-chain antibodyome
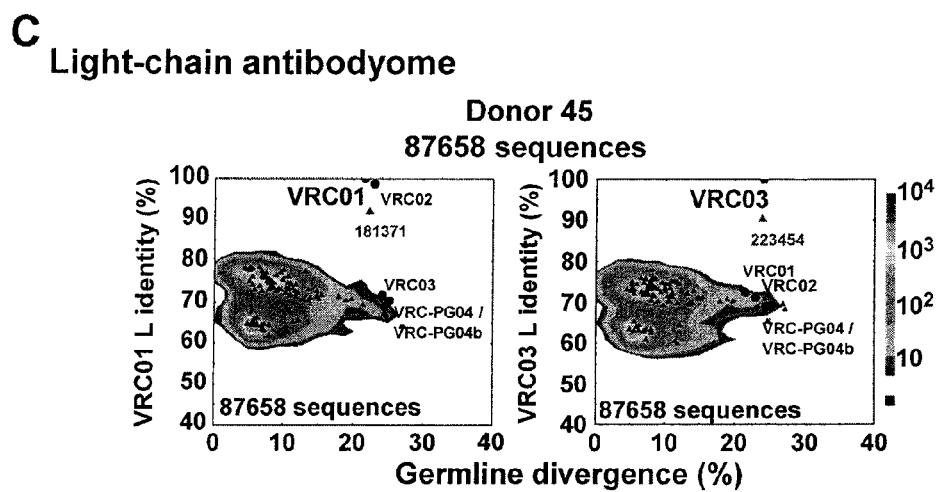
D Light-chain neutralization
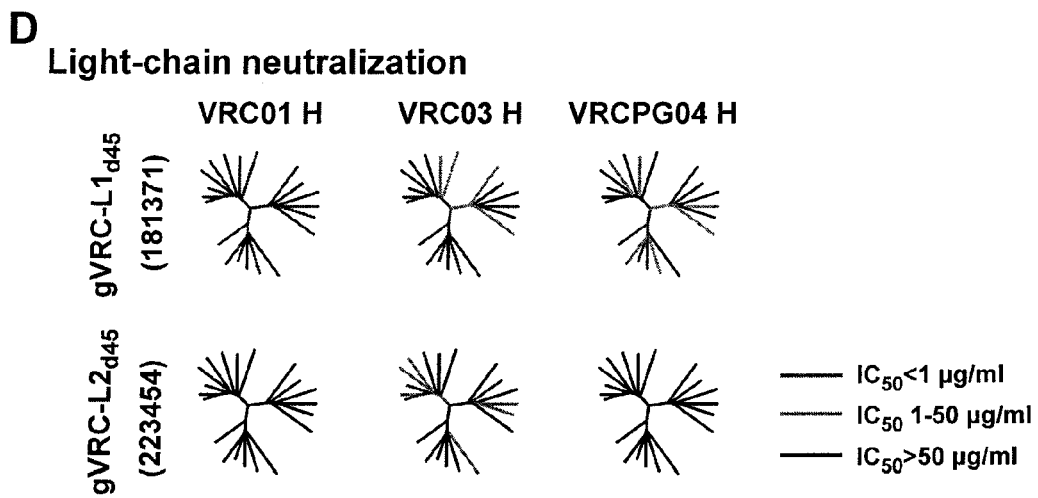

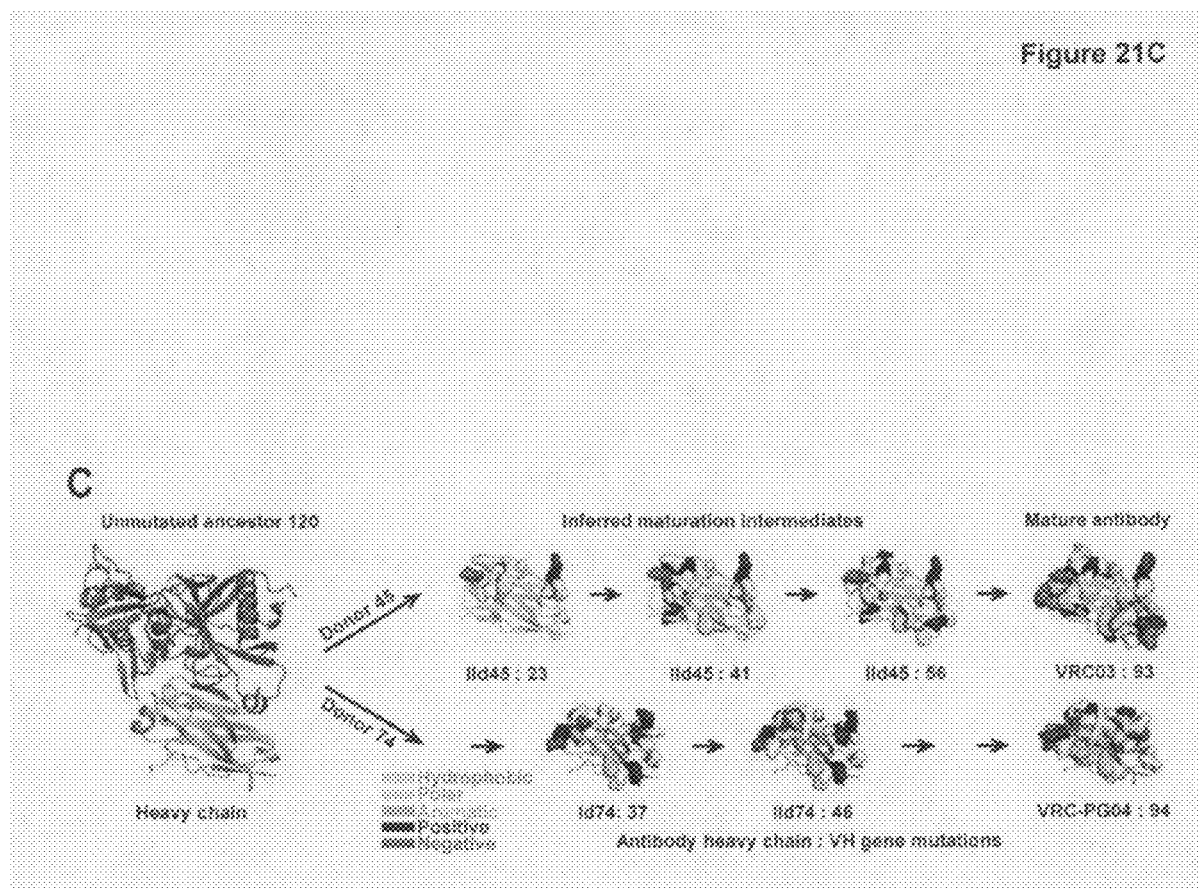

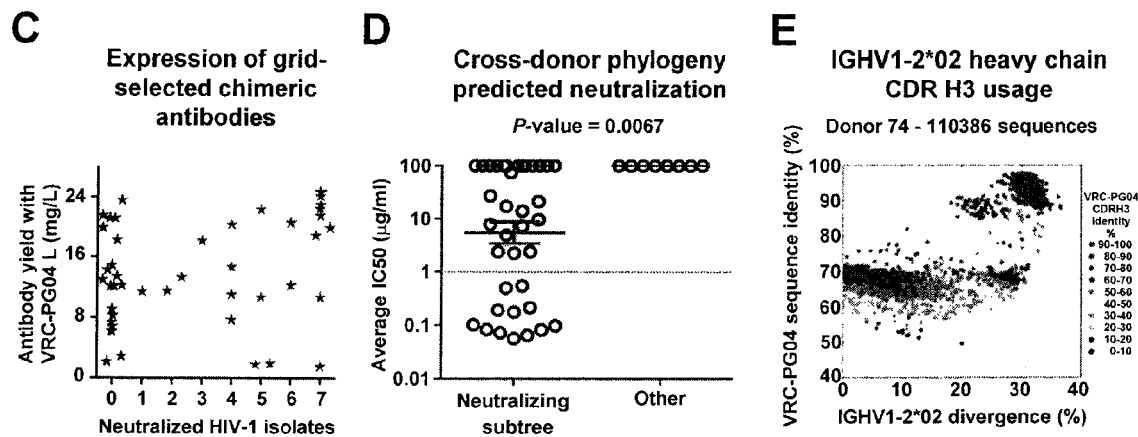
Figure 22 C-E

SEQUENCE LISTING

```
<160> NUMBER OF SEQ ID NOS: 40

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: This sequence may encompass 12-18 nucleotides

<400> SEQUENCE: 1
tttttttttt tttttttt                                                 18

<210> SEQ ID NO 2
<211> LENGTH: 119
<212> TYPE: PRT
<213> ORGANISM: Homo sapiens

<400> SEQUENCE: 2
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Val Trp Ala Glu Tyr Phe Gln His Trp Gly Gln Gly
            100                 105                 110

Thr Leu Val Thr Val Ser Ser
        115

<210> SEQ ID NO 3
<211> LENGTH: 121
<212> TYPE: PRT
<213> ORGANISM: Unknown
<220> FEATURE:
<223> OTHER INFORMATION: Description of Unknown: VRC01
      peptide

<400> SEQUENCE: 3

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
        50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 4
<211> LENGTH: 121
<212> TYPE: PRT
<213> ORGANISM: Unknown
<220> FEATURE:
<223> OTHER INFORMATION: Description of Unknown: VRC02
      peptide

<400> SEQUENCE: 4

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
                20                  25                  30

Thr Leu Asn Trp Val Arg Leu Ala Pro Gly Arg Arg Pro Glu Trp Met
            35                  40                  45

```
Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Thr Ala Val Tyr Tyr Cys
                85                  90                  95

Thr Arg Gly Lys Asn Cys Asp Tyr Asn Trp Asp Phe Glu His Trp Gly
                100                 105                 110

Arg Gly Thr Pro Val Thr Val Ser Ser
        115                 120

<210> SEQ ID NO 5
<211> LENGTH: 130
<212> TYPE: PRT
<213> ORGANISM: Unknown
<220> FEATURE:
<223> OTHER INFORMATION: Description of Unknown: VRC03
      peptide

<400> SEQUENCE: 5

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
                20                  25                  30

Ser Ile His Trp Val Arg Leu Ile Pro Asp Lys Gly Phe Glu Trp Ile
            35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
                100                 105                 110

Gly Asp Phe Pro Trp Gln Tyr Trp Gly Gln Gly Thr Val Val Val Val
            115                 120                 125

Ser Ser
    130

<210> SEQ ID NO 6
<211> LENGTH: 125
<212> TYPE: PRT
<213> ORGANISM: Homo sapiens

<400> SEQUENCE: 6

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
                20                  25                  30

Glu Leu Ile His Trp Val Arg Gln Ala Pro Gly Gln Gly Leu Glu Trp
            35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95
```

```
Phe Cys Ala Arg Gln Lys Phe Tyr Thr Gly Gly Gln Gly Trp Tyr Phe
                100                 105                 110

Asp Leu Trp Gly Arg Gly Thr Leu Ile Val Val Ser Ser
            115                 120                 125

<210> SEQ ID NO 7
<211> LENGTH: 98
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 8
<211> LENGTH: 126
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Asn Arg Asp
            20                  25                  30

Trp Met Thr Trp Val Arg Gln Ala Pro Gly Lys Gly Leu Glu Trp Val
        35                  40                  45

Ala Asn Ile Asn Met Asp Gly Asp Lys Lys Asp Tyr Val Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Arg Ala Gly Asp Thr Ala Val Tyr Tyr Cys
                85                  90                  95

Ala Arg Ile Arg Gln Val Ser Lys Tyr Leu Gln Trp Tyr Pro Gly Val
                100                 105                 110

Phe Glu Met Trp Gly Gln Gly Thr Met Val Thr Val Ser Ser
            115                 120                 125

<210> SEQ ID NO 9
<211> LENGTH: 107
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Arg Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Tyr
                 85                  90                  95

Thr Phe Gly Gln Gly Thr Lys Leu Glu Ile Lys
                100                 105
```

<210> SEQ ID NO 10
<211> LENGTH: 103
<212> TYPE: PRT
<213> ORGANISM: Unknown
<220> FEATURE:
<223> OTHER INFORMATION: Description of Unknown: VRC01
      peptide

<400> SEQUENCE: 10

```
Glu Ile Val Leu Thr Gln Ser Pro Gly Thr Leu Ser Leu Ser Pro Gly
 1               5                  10                  15

Glu Thr Ala Ile Ile Ser Cys Arg Thr Ser Gln Tyr Gly Ser Leu Ala
                 20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
 50                  55                  60

Trp Gly Pro Asp Tyr Asn Leu Thr Ile Ser Asn Leu Glu Ser Gly Asp
 65                  70                  75                  80

Phe Gly Val Tyr Tyr Cys Gln Gln Tyr Glu Phe Phe Gly Gln Gly Thr
                 85                  90                  95

Lys Val Gln Val Asp Ile Lys
                100
```

<210> SEQ ID NO 11
<211> LENGTH: 103
<212> TYPE: PRT
<213> ORGANISM: Unknown
<220> FEATURE:
<223> OTHER INFORMATION: Description of Unknown: VRC02
      peptide

<400> SEQUENCE: 11

```
Glu Ile Val Leu Thr Gln Ser Pro Gly Thr Leu Ser Leu Ser Pro Gly
 1               5                  10                  15

Glu Thr Ala Ile Ile Ser Cys Arg Thr Ser Gln Tyr Gly Ser Leu Ala
                 20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
 50                  55                  60

Trp Gly Pro Asp Tyr Asn Leu Thr Ile Arg Asn Leu Glu Ser Gly Asp
 65                  70                  75                  80

Phe Gly Leu Tyr Tyr Cys Gln Gln Tyr Glu Phe Phe Gly Gln Gly Thr
                 85                  90                  95

Lys Val Gln Val Asp Ile Lys
                100
```

<210> SEQ ID NO 12
<211> LENGTH: 96
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 13
<211> LENGTH: 102
<212> TYPE: PRT
<213> ORGANISM: Unknown
<220> FEATURE:
<223> OTHER INFORMATION: Description of Unknown: VRC03
      peptide

<400> SEQUENCE: 13

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His
            100

<210> SEQ ID NO 14
<211> LENGTH: 101
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg
            100

<210> SEQ ID NO 15
<211> LENGTH: 97
<212> TYPE: PRT
<213> ORGANISM: Homo sapiens

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr

<210> SEQ ID NO 16
<211> LENGTH: 112
<212> TYPE: PRT
<213> ORGANISM: Homo sapiens

<400> SEQUENCE: 16

Asp Ile Val Met Thr Gln Ser Pro Asp Ser Leu Ala Val Ser Leu Gly
1               5                   10                  15

Glu Arg Ala Thr Ile His Cys Lys Ser Ser Gln Ser Val Leu Tyr Arg
            20                  25                  30

Pro Asn Asn Arg Asn Tyr Val Ala Trp Tyr Gln Gln Lys Pro Gly Gln
        35                  40                  45

Pro Pro Arg Leu Leu Ile His Trp Ala Ser Phe Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Phe Leu Tyr Ser Phe Gly Gly Gly Thr Lys Leu Glu Ile Asn
            100                 105                 110

<210> SEQ ID NO 17
<211> LENGTH: 98
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 18
<211> LENGTH: 121
<212> TYPE: PRT
<213> ORGANISM: Unknown
<220> FEATURE:
<223> OTHER INFORMATION: Description of Unknown: VRC01
      peptide

<400> SEQUENCE: 18

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 19
<211> LENGTH: 121
<212> TYPE: PRT
<213> ORGANISM: Unknown
<220> FEATURE:
<223> OTHER INFORMATION: Description of Unknown: VRC02
      peptide

<400> SEQUENCE: 19

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120

<210> SEQ ID NO 20
<211> LENGTH: 130
<212> TYPE: PRT
<213> ORGANISM: Unknown
<220> FEATURE:
<223> OTHER INFORMATION: Description of Unknown: VRC03
      peptide

<400> SEQUENCE: 20

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
        115                 120                 125

Ser Ser
    130

<210> SEQ ID NO 21
<211> LENGTH: 125
<212> TYPE: PRT
<213> ORGANISM: Homo sapiens

<400> SEQUENCE: 21

Gln Val Gln Leu Val Gln Ser Gly Ser Gly Val Lys Lys Pro Gly Ala
1               5                   10                  15

Ser Val Arg Val Ser Cys Trp Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 22
<211> LENGTH: 125

-continued

```
<212> TYPE: PRT
<213> ORGANISM: Homo sapiens

<400> SEQUENCE: 22

Gln Val Gln Leu Val Gln Ser Gly Ser Gly Val Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 23
<211> LENGTH: 131
<212> TYPE: PRT
<213> ORGANISM: Homo sapiens

<400> SEQUENCE: 23

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu His Gly Arg Leu Thr Ala Thr
65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Ala
        115                 120                 125

Val Ser Ser
    130

<210> SEQ ID NO 24
<211> LENGTH: 131
<212> TYPE: PRT
<213> ORGANISM: Homo sapiens

<400> SEQUENCE: 24

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
```

```
                35                  40                  45

Ala Pro Gly Gln Gln Leu Glu Trp Leu Ala Trp Met Asn Pro Thr Asn
 50                  55                  60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Lys Ser Leu Arg
                 85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
            115                 120                 125

Val Ser Ser
130

<210> SEQ ID NO 25
<211> LENGTH: 131
<212> TYPE: PRT
<213> ORGANISM: Homo sapiens

<400> SEQUENCE: 25

Gln Val Gln Leu Val Gln Ser Gly Ala Ala Val Arg Lys Pro Gly Ala
 1               5                  10                  15

Ser Val Thr Val Ser Cys Lys Phe Ala Glu Asp Asp Phe Ser Pro
                 20                  25                  30

His Trp Val Asn Pro Ala Pro Glu His Tyr Ile His Phe Leu Arg Gln
                 35                  40                  45

Ala Pro Gly Gln Gln Leu Glu Trp Leu Ala Trp Met Lys Pro Thr Asn
 50                  55                  60

Gly Ala Val Asn Tyr Ala Trp Gln Leu Gln Gly Arg Val Thr Val Thr
 65                  70                  75                  80

Arg Asp Arg Ser Gln Thr Thr Ala Phe Leu Glu Val Lys Asn Leu Arg
                 85                  90                  95

Ser Asp Asp Thr Ala Val Tyr Tyr Cys Ala Arg Ala Gln Lys Arg Gly
                100                 105                 110

Arg Ser Glu Trp Ala Tyr Ala His Trp Gly Gln Gly Thr Pro Val Val
            115                 120                 125

Ile Ser Ala
130

<210> SEQ ID NO 26
<211> LENGTH: 131
<212> TYPE: PRT
<213> ORGANISM: Homo sapiens

<400> SEQUENCE: 26

Gln Val Gln Leu Val Gln Ser Gly Ala Ala Val Arg Lys Pro Gly Ala
 1               5                  10                  15

Ser Ile Ser Val Ser Cys Lys Phe Ala Asp Ala Asp Tyr Ser Pro
                 20                  25                  30

His Trp Met Asn Pro Ala Pro Glu His Tyr Ile His Phe Leu Arg Gln
                 35                  40                  45

Ala Pro Gly Gln Gln Leu Glu Trp Leu Ala Trp Met Asn Pro Thr Asn
 50                  55                  60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Arg Ser Leu Arg
```

```
                85                  90                  95

Ser Asp Asp Thr Ala Val Tyr Tyr Cys Ala Arg Ala Gln Lys Arg Ala
            100                 105                 110

Arg Ser Glu Trp Ala Tyr Ala His Trp Gly Gln Gly Thr Pro Val Val
        115                 120                 125

Val Ser Ser
    130

<210> SEQ ID NO 27
<211> LENGTH: 131
<212> TYPE: PRT
<213> ORGANISM: Homo sapiens

<400> SEQUENCE: 27

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Trp Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu Asn Gly Arg Leu Thr Ala Thr
65                  70                  75                  80

Arg Asp Thr Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 28
<211> LENGTH: 90
<212> TYPE: PRT
<213> ORGANISM: Homo sapiens

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Gln Gln
                85                  90

<210> SEQ ID NO 29
<211> LENGTH: 103
<212> TYPE: PRT
<213> ORGANISM: Unknown
<220> FEATURE:
<223> OTHER INFORMATION: Description of Unknown: VRC01
```

```
                            peptide

<400> SEQUENCE: 29

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
            100

<210> SEQ ID NO 30
<211> LENGTH: 103
<212> TYPE: PRT
<213> ORGANISM: Unknown
<220> FEATURE:
<223> OTHER INFORMATION: Description of Unknown: VRC02
      peptide

<400> SEQUENCE: 30

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys
            100

<210> SEQ ID NO 31
<211> LENGTH: 91
<212> TYPE: PRT
<213> ORGANISM: Homo sapiens

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln
            85                  90

<210> SEQ ID NO 32
<211> LENGTH: 102
<212> TYPE: PRT
<213> ORGANISM: Unknown
<220> FEATURE:
<223> OTHER INFORMATION: Description of Unknown: VRC03
      peptide

<400> SEQUENCE: 32

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Gly Leu Gly
                85                  90                  95

Ser Glu Leu Glu Val His
            100

<210> SEQ ID NO 33
<211> LENGTH: 101
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
    50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg
            100

<210> SEQ ID NO 34
<211> LENGTH: 101
<212> TYPE: PRT
<213> ORGANISM: Homo sapiens

<400> SEQUENCE: 34

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
            35                  40                  45

Thr Ser Lys Arg Ala Ser Gly Ile Pro Asp Arg Phe Ser Gly Ser Gln
 50                  55                  60

Phe Gly Lys Gln Tyr Thr Leu Thr Ile Thr Arg Met Glu Pro Glu Asp
 65                  70                  75                  80

Phe Ala Gly Tyr Tyr Cys Gln Gln Val Glu Phe Phe Gly Gln Gly Thr
                 85                  90                  95

Arg Leu Glu Ile Arg
            100

<210> SEQ ID NO 35
<211> LENGTH: 90
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln
                 85                  90

<210> SEQ ID NO 36
<211> LENGTH: 103
<212> TYPE: PRT
<213> ORGANISM: Homo sapiens

<400> SEQUENCE: 36

Asp Ile Gln Met Thr Gln Ser Pro Ser Ser Leu Ser Ala Ser Leu Gly
 1               5                  10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Lys Ala Pro Lys Leu Leu Val
            35                  40                  45

Ser Asp Ala Ser Ile Leu Glu Gly Gly Val Pro Ser Arg Phe Ser Gly
 50                  55                  60

Ser Gly Phe His Gln Asn Phe Ser Leu Thr Ile Ser Ser Leu Gln Pro
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 37
<211> LENGTH: 103
<212> TYPE: PRT
<213> ORGANISM: Homo sapiens

<400> SEQUENCE: 37

Asp Ile Gln Met Thr Gln Ser Pro Ser Ser Leu Ser Ala Ser Leu Gly
 1               5                  10                  15

```
                1               5                   10                  15
        Asp Arg Val Thr Ile Thr Cys Gln Ala Ser Arg Gly Ile Gly Lys Asp
                        20                  25                  30

Leu Asn Trp Tyr Gln Gln Lys Ala Gly Lys Ala Pro Lys Leu Leu Val
                        35                  40                  45

Ser Asp Ala Ser Thr Leu Glu Gly Gly Val Pro Ser Arg Phe Ser Gly
                50                  55                  60

Ser Gly Phe His Gln Asn Phe Ser Leu Thr Ile Ser Ser Leu Gln Ala
        65                      70                  75                  80

Glu Asp Val Ala Thr Tyr Phe Cys Gln Gln Tyr Glu Thr Phe Gly Gln
                        85                  90                  95

Gly Thr Lys Val Asp Ile Lys
                        100

<210> SEQ ID NO 38
<211> LENGTH: 103
<212> TYPE: PRT
<213> ORGANISM: Homo sapiens

<400> SEQUENCE: 38

Asp Ile Gln Met Thr Gln Ser Pro Ser Ser Leu Ser Ala Ser Leu Gly
        1               5                   10                  15

Asp Arg Val Thr Ile Thr Cys Gln Ala Ser Arg Gly Ile Gly Lys Asp
                        20                  25                  30

Leu Asn Trp Tyr Gln Gln Lys Pro Gly Arg Ala Pro Lys Leu Leu Val
                        35                  40                  45

Ser Asp Ala Ser Ile Leu Glu Gly Gly Val Pro Thr Arg Phe Ser Gly
                50                  55                  60

Ser Gly Phe His Gln Asn Phe Ser Leu Thr Ile Ser Ser Leu Gln Ala
        65                      70                  75                  80

Glu Asp Val Ala Thr Tyr Phe Cys Gln Gln Tyr Glu Thr Phe Gly Gln
                        85                  90                  95

Gly Thr Lys Val Asp Ile Lys
                        100

<210> SEQ ID NO 39
<211> LENGTH: 103
<212> TYPE: PRT
<213> ORGANISM: Homo sapiens

<400> SEQUENCE: 39

Asp Ile Gln Met Thr Gln Ser Pro Ser Ser Leu Ser Ala Ser Leu Gly
        1               5                   10                  15

Asp Arg Val Thr Ile Thr Cys Gln Ala Ser Arg Gly Ile Gly Lys Asp
                        20                  25                  30

Leu Asn Trp Tyr Gln Gln Lys Arg Gly Arg Ala Pro Arg Leu Leu Val
                        35                  40                  45

Ser Asp Ala Ser Val Leu Glu Gly Gly Val Pro Ser Arg Phe Ser Gly
                50                  55                  60

Ser Gly Phe His Gln Asn Phe Ser Leu Thr Ile Ser Thr Leu Gln Pro
        65                      70                  75                  80

Glu Asp Val Ala Thr Tyr Phe Cys Gln Gln Tyr Glu Thr Phe Gly Gln
                        85                  90                  95

Gly Thr Lys Val Asp Ile Lys
                        100
```

```
<210> SEQ ID NO 40
<211> LENGTH: 103
<212> TYPE: PRT
<213> ORGANISM: Homo sapiens

<400> SEQUENCE: 40

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100
```

US 9,382,311 B2

HIV-1 BROADLY NEUTRALIZING ANTIBODIES

RELATED APPLICATIONS AND INCORPORATION BY REFERENCE

This application is a continuation-in-part application of international patent application Serial No. PCT/US2011/052933 filed Sep. 23, 2011, which published as PCT Publication No. WO 2012/040562 on Mar. 29, 2012, which claims priority to U.S. provisional patent application Ser. No. 61/386,211 filed Sep. 24, 2010 and U.S. provisional patent application Ser. No. 61/515,528 filed Aug. 5, 2011.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Jan. 12, 2012, is named 49094992.txt and is 40,911 bytes in size.

FIELD OF THE INVENTION

This application relates to human neutralizing monoclonal antibodies specific for HIV-1, such as broad and potent neutralizing monoclonal antibodies specific for HIV-1 and their manufacture and use. Broad neutralization suggests that the antibodies can neutralize HIV-1 isolates from different individuals. Such antibodies are useful in pharmaceutical compositions for the prevention and treatment of HIV, and for the diagnosis and monitoring of HIV infection and for design of HIV vaccine immunogens.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virallyencoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5370):1884-8). For fusion with its target cells, HIV-1 uses a trimeric Env complex containing gp120 and gp41 subunits (Burton et al., Nat Immunol. 2004 March; 5(3):233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens.

Recently using a sensitive high-throughput micro-neutralization screening of supernatants from approximately 30,000 IgG+ memory B cells from a HIV-1 clade A-infected African donor, two new broadly neutralizing antibodies PG9 and PG16 that are broad and exceptionally potent neutralizing antibodies were identified (Walker L, Phogat S, et al. Science. 2009; 326:285-9. Epub 2009 Sep. 3). These antibodies recognize a new conserved, yet accessible, vaccine target (consisting of conserved elements on the variable loops 2 and 3) on the Env and show preferential binding to HIV Env trimer (model of PG9 and 16 epitopes on HIV-1 trimer.). When tested for binding, these antibodies did not show binding to many empirically designed soluble (Env gp140) HIV Env trimers thought to be mimics of the native HIV-1 Env spike, suggesting that either these Env designs are incorrect or they are fixed in a form not recognized by PG9 and PG16.

Other broadly neutralizing monoclonal antibodies that bind the CD4-binding site have also been identified (Wu et al, Science 329; 856 (2010) and Zhou et al., Science. 2010 Aug. 13; 329(5993):811-7. Epub 2010 Jul. 8).

Citation or identification of any document in this application is not an admission that such document is available as prior art to the present invention.

SUMMARY OF THE INVENTION

The present invention is based, in part, on novel monoclonal antibodies identified from modified HIV-1 envelope (Env) structures, in particular, Env structures with resurfaced stabilized cores (RSC) containing antigenically resurfaced glycoproteins specific for a structurally conserved site of CD4 receptor binding.

The present invention relates to an isolated or non-naturally occurring human monoclonal antibody, wherein the monoclonal antibody may neutralize a HIV-1 virus in vitro. The monoclonal antibody may be selected from the group consisting of VRC-PG-04 or VRC-PG-05.

The invention also encompasses antibodies that have a heavy chain with three CDRs which may comprise an amino acid sequence selected from the group consisting of the amino acid sequences of VRC-PG-04 or VRC-PG-05 of FIG. 8, and a light chain with three CDRs that include an amino acid sequence selected from the group consisting of the amino acid sequences of VRC-PG-04 or VRC-PG-05 of FIG. 8.

The invention further encompasses compositions that may comprise the isolated or non-naturally occurring anti-HIV antibodies of the present invention. The invention also relates to nucleic acid molecules that may encode the anti-HIV antibodies of the present invention, or a fragment thereof, vectors that may comprise the nucleic acid molecules that may encode the anti-HIV antibodies of the present invention, or a fragment thereof, and cells that may comprise vectors that may comprise the nucleic acid molecules that may encode the anti-HIV antibodies of the present invention, or a fragment thereof.

The present invention also relates to methods of immunizing or reducing the effect of an HIV infection or an HIV-related disease which may comprise identifying a patient in need of such treatment, and administering to said patient a therapeutically effective amount of at least one antibody of the present invention. The method may additionally comprise the administration of a second therapeutic agent. The second therapeutic agent may be an anti-viral agent.

The present invention also relates to methods of immunizing or reducing the effect of an HIV infection or an HIV-related disease which may comprise identifying a patient in need of such treatment and administering to said patient a therapeutically effective amount of: a first antibody of the present invention, or fragment thereof, specific for a first epitope which binds to said first antibody and a second antibody of the present invention, or fragment thereof, specific for a second epitope which binds to said second antibody.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 8A-B depicts sequence alignments of VRC-PG antibodies (SEQ ID NOS 2-16, respectively, in order of appearance).

FIGS. 9A-B depict antigen binding properties of PGV04. (A) PGV04 binding to RSC3 (solid lines) and ΔRSC3 (dashed lines), and (B) JRFL gp120 as determined by ELISA. Antigens were coated directly on ELISA plates. OD, optical density (absorbance at 405 nm) VRC01, VRC03, b12, and 2G12 were used as controls for binding to the antigens.

FIGS. 10A-D depict mapping the PGV04 binding epitope. (A) Competition ELISAs of PGV04 with the CD4bs mAbs b12 and VRC01, CD4-IgG; (B) CD4i mAbs 17b and X5; and (C) the glycan binding mAb 2G12 and V3-loop binding mAb F425. JRFL gp120 was coated on ELISA plates and serial dilutions of the mAbs indicated at the top of the graph was added for 30 min at RT. The biotinylated mAbs listed in the legend were then added for 1 hr at RT at EC50 constant concentration. (D) Reverse competition ELISA with serial dilutions of PGV04 binding to JRFL gp120 coated ELISA plates and then the addition of a constant EC50 concentration of the biotinylated mAbs listed in the legend. All experiments were performed in duplicate, and data is one representative experiment with SEM plotted.

FIGS. 11A-C depict neutralization activity of PGV04 on a 162- and on a 97-virus panel. (A) Potency of neutralization. Boxes are color coded as follows: orange, median potency between 0.2 and 2.0 μg/ml; and red, median potency <0.2 μg/ml. CRF07_BC, CRF08_BC, and AC viruses were not included in the clade analysis, but are counted toward the total number of neutralized viruses in the 162-virus panel because there was only one virus tested for each of these clades. Clade D and E viruses were not included in the clade analysis, but are counted toward the total number of neutralized viruses in the 97-virus panel because there was only 2 and 3 viruses respectively tested for these clades. (B) Breath of neutralization. Boxes are colored as follows: orange, 61-90% of viruses neutralized; red, 91-100% of viruses neutralized. As in (A), CRF07_BC, CRF08_BC, AC, D and E viruses were not included in the clade analysis, but are counted toward the total number of neutralized viruses for the respective panel. (C) Dependence of serum $NT_{50}$ on PGV04. Spearman correlation was performed comparing the mAb $IC_{50}$ and the donor serum $NT_{50}$ for the 162 viruses tested. The Spearman's rank correlation coefficient was calculated as −0.71 and the correlation was significant with a P-value <0.0001. $IC_{50}$s and $NT_{50}$s of viruses that did not neutralize were entered at the limit of the assay as 50 μg/ml for the mAb or 100 (1/dilution) for the serum.

FIGS. 12A-D depict induction of the co-receptor binding site on gp120 and cell surface expressed trimers. Saturating amounts of the mAbs listed in the legend were added to either JRFL or YU2 gp120 coated ELISA plates. After 30 min incubation at RT, a dilution curve of biotinylated (A) 17b or (b) X5 was added for 1 hr at RT. Binding was detected with a streptavidin-AP and absorbance was read at 405 nm. The ability of PGV04 to induce the co-receptor binding site on cell surface trimers was measured (C). Saturating amounts of the mAbs listed in the legend were added to 293T cells expressing HIV envelope on their surface for 30 min. Either biotinylated 17b or control (D) mAb 2G12 were added to the cells. A streptavidin mAb conjugated to PE was used for detection and binding was measured using flow cytometry.

FIGS. 13A-G depict MAb Neutralization and binding to JR-CSF gp120 containing single alanine substitutions. (A) PGV04 neutralization of JR-CSF pseudoviruses containing single alanine substitutions in the gp120 protein. Entry into TZM-bl cells was measured using a luminometer in relative light units (RLU). Neutralization potency relative to WT was calculated using the following equation: (IC50_WT)/(IC50_mutant)*100. (B) PGV04 binding to JR-CSF gp120 isolated from pseudovirus and containing single alanine substitutions. Amino acid numbering is based on the sequence of HIV-1HXB2. Boxes are color-coded as follows: blue, 0-5% neutralization relative wild-type; green, 6-40% neutralization relative to wild-type; and yellow, 250-1,000% neutralization relative to wild-type.

FIGS. 14A-B depict ability of PGV04 to bind Endo-H and Endo-F-treated BaL gp120. The mAb binding to (A) mock treated gp120 or (B) Endo-H and Endo-F treated gp120.

FIGS. 15A-I depict (A) Neutralization activity of mAbs against a cross-clade 162-pseudovirus panel. (B) Neutralization activity of mAbs against a cross-clade 97-pseudovirus panel.

FIGS. 17A-D depicts dentification and characterization of mAbs from HIV-1-infected donors 74 and 0219. (A) RSC3 analysis of serum. Twelve sera from the IAVI Protocol G cohort (donors 17-74) and one serum from the CHAVI 001 cohort (donor 0219) were analyzed for RSC3 reduction in serum neutralization on HIV-1 strains JR-FL, PVO.4, YU2 and ZA12.29. Blue bars show the mean serum reduction in neutralization IC50 resulting from RSC3 versus ΔRSC3 competition. Sera with greatest reduction were further analyzed on HIV-1 strains Q168.a2, RW020.2, Du156.12 and ZM109.4. Red bars show the mean reduction on eight viruses. (B) Flow cytometric identification RSC3-reactive IgG+ B cells from donors 74 and 0219. Gating and percentage of IgG+ B cells of interest (RSC3+ΔRSC3−) are indicated, with 40 and 26 sorted single B cells from donors 74 and 0219 respectively. (C) Protein sequences of heavy and light chain variable regions of mAbs VRC-PG04 and VRC≈-PG04b, isolated from donor 74, and mAbs VRC-CH30-34 isolated from donor 0219. Sequences are aligned to the putative germline ancestral genes and to previously identified broadly neutralizing antibodies VRC01, VRC02 and VRC03. Framework regions (FR) and complementarity-determining regions (CDRs) are based on Kabat nomenclature (E. A. Kabat, T. T. Wu, K. S. Gottesman, C. Foeller, Sequences of Proteins of Immunological Interest. 5th Edition (1991)). FIG. 17C discloses SEQ ID NOS 17-40, respectively, in order of appearance. (D) Neutralization dendrograms. VRC-PG04 and VRC-CH31 were tested against genetically diverse Env-pseudoviruses representing the major HIV-1 clades. Neighbor-joining trees display the protein distance of gp160 sequences from 178 HIV-1 isolates tested against VRC-PG04 and a subset (80 isolates) tested against VRC-CH31. A scale bar denotes 1% distance in amino acid sequence. Tree branches are colored by the neutralization potencies of VRC-PG04 and VRC-CH31 against each particular virus.

FIGS. 18A-C depict a structure of antibodies VRC-PG04 and VRC03 in complex with HIV-1 gp120. (A) Overall structures. The liganded complex for the Fab of antibody VRC-PG04 from donor 74 and the HIV-1 gp120 envelope glycoprotein from isolate 93TH057 is depicted with polypeptide backbones in ribbon representation in the left image. The complex of Fab VRC03 from donor 45 is depicted in the right image, with surfaces of all variable domain residues that differ between VRC03 and VRC-PG04 colored according to their chemical characteristics. (B and C) Interaction close-ups. Critical interactions are shown between the CD4-binding loop of gp120 (purple) and the CDR H2 region of the broadly neutralizing mAbs, VRC03 and VRC-PG04 (reported here) and VRC01 (reported previously (T. Zhou et al., Structural basis for broad and potent neutralization of HIV-1 by antibody VRC01. *Science* 329, 811-817 (2010))), with hydrogen bonds depicted as dotted lines. The 1.9 and 2.1 Å resolution structures of VRC03 and VRC-PG04, respectively, were sufficient to define interfacial waters shown in (C), which were unclear in the 2.9 Å structure of VRC01. The orientation shown in (C) is ~180° rotated about the vertical axis from the orientation shown in (B).

FIGS. 19A-C depict focused evolution of VRC01-like antibodies. (A) Antibody convergence. The gp120 portions of liganded complexes with VRC01, VRC03 and VRC-PG04 were superimposed to determine the average antibody per-residue Cα deviation, and the per-residue hydrophobic interaction ($\Delta^i G$) was calculated (E. Krissinel, K. Henrick, Inference of macromolecular assemblies from crystalline state. *J Mol Biol* 372, 774-797 (2007)). These two quantities were found to correlate (P-value=0.0427), with antibody residues containing strong hydrophobic interactions (e.g., at positions 53 and 55 in the heavy chain, and 91 and 97 in the light chain, VRC-PG04-relative numbering) displaying high structural conservation. This correlation is visualized on VRC-PG04 in the left image, where the ribbon thickness is proportional to the corresponding per-residue Cα deviation and the paratope surface is colored according to hydrophobicity, from white (low) to red (high); notably, red surface patches map to thin ribbons. (B) Epitope convergence. The HIV-1 gp120 surface involved with CD4 binding contains conformationally invariant regions (e.g. associated with the outer domain) and conformationally variable regions (e.g. associated with the bridging sheet). Applicants previously hypothesized that the conformationally invariant outer domain-contact for CD4 represents a site of vulnerability (T. Zhou et al., Structural basis for broad and potent neutralization of HIV-1 by antibody VRC01. *Science* 329, 811-817 (2010)). Applicants analyzed the precision of CD4-binding-site ligand recognition (vertical axis) versus the IC80 neutralization breadth (horizontal axis) and observed significant correlation ($R^2$=0.6, P-value=0.040). (C) Divergences in sequence and convergences in recognition. The development of VRC01-like antibodies involves a heavy chain derived from the IGHV1-2*02 allele and selected light chain Vκ alleles. The far left image depicts ribbon representation model of a putative germline antibody. Somatic hypermutation during the process of affinity maturation leads to a divergence in sequence, yet results in the convergent recognition of similar epitopes. Intersection of the epitope surfaces recognized by VRC01, VRC03 and VRC-PG04 (far right image), reveals a remarkable similarity to the site of vulnerability. The primary divergence of this intersection from the hypothesized site of vulnerability occurs in the region of HIV-1 gp120 recognized by the light chain of the VRC01-like antibodies. While the separate epitopes on gp120 do show differences in recognition surface, these primarily involve the bridging sheet region, which is likely to adopt a different conformation in the functional viral spike prior to engagement of CD4.

FIGS. 20A-E depict deep sequencing of expressed heavy and light chains from donors 45 and 74. (A) Heavy and light chain complementation. The neutralization profiles of VRC01 and VRC03 (donor 45), VRC-PG04 (donor 74), and VRCCH31 (donor 0219) and their heavy and light chain chimeric swaps are depicted with 20-isolate neutralization dendrograms. Explicit neutralization IC50s are provided in table S13. (B) The repertoire of heavy chain sequences from donor 45 (2008 sample) and donor 74 (2008 sample). Heavy chain sequences are plotted as a function of sequence identity to the heavy chain of VRC01 (left), VRC03 (middle) and VRC-PG04 (right) and of sequence divergence from putative genomic $V_H$-alleles: upper row plots show sequences of putative IGHV1-2*02 allelic origin; lower row plots show sequences from other allelic origins. Color coding indicates the number of sequences. (C) Repertoire of expressed light chain sequences from donor 45 (2001 sample). Light chain sequences are plotted as a function of sequence identify to VRC01 (left) and VRC03 (right) light chains, and of sequence divergence from putative genomic V-gene alleles. Sequences with 2-residue deletions in the CDR L1 region (which is observed in VRC01 and VRC03) are shown as black dots. Two light chain sequences, with 92.0% identify to VRC01 (sequence ID 181371) and with 90.3% identify to VRC03 (sequence ID 223454) are highlighted with red triangles. (D) Functional assessment of light chain sequences identified by deep sequencing. The neutralization profiles of sequence 181371 reconstituted with the VRC01 heavy chain (named gVRC-L1$_{d45}$) and of sequence 223454 reconstituted with the VRC03 heavy chain (named gVRC-L2$_{d45}$) are depicted with 20-isolate neutralization dendrograms; explicit neutralization IC$_{50}$s are shown provided in table S22. (E) Functional assessment of heavy chain sequences identified by deep sequencing. Heavy chain sequences from donors 45 and 74 were synthesized and expressed with either the light chain of VRC01 or VRC03 (for donor 45) or the light chain of VRC-PG04 (for donor 74) and evaluated for neutralization. Neutralizing sequences are shown as red stars and are labeled. gVRC-H(n)$_{d74}$ refers to the heavy chains with confirmed neutralization when reconstituted with the light chain of VRC-PG04, with controls. Applicants also assessed 454-derived sequences for structural compatibility with the VRC01, VRC03, and VRC-PG04 gp120-complex crystal structures using a threading algorithm which assessed structural compatibility using the DFIRE statistical potential (H. Zhou, Y. Zhou, Distance-scaled, finite ideal-gas reference state improves structure-derived potentials of mean force for structure selection and stability prediction. *Protein Sci* 11, 2714-2726 (2002)). None of the ten sequences with optimal DFIRE scores, nor those with high germline divergence of non-IGHV1-2*02 genomic origin displayed neutralization when reconstituted with the VRC01 light chain (FIG. 4E). Thus, sequence similarity, IGHV1-2*02 origin, and divergence all correlate with neutralization potential, but other factors such as predicted structural compatibility failed to identify VRC01-like antibodies FIGS. 21A-C depict maturational similarities of VRC01-like antibodies in different donors revealed by cross-donor phylogenetic analysis. (A) Maximum-likelihood trees of heavy chain sequences of the IGHV1-2*02 origin from donor 45 (left) and donor 74 (right). The subset of sequences shown was selected based on the germline divergence as described in SOM. The donor 45 tree is rooted by the putative reverted unmutated ancestor of the heavy chain of VRC01, and also includes specific neutralizing sequences from donor 74 and 0219 (shown in red). Similarly the donor 74 tree is rooted in the putative reverted unmutated ancestor of the heavy chain of VRC-PG04, and sequences donor 45 and 0219 are included in the cross-donor phylogenetic analysis. Bars representing 0.1 changes per nucleotide site are shown. Insets show J chain assignments for all sequences within the neutralizing subtree identified by an iterative neighbor-joining tree analysis as described in SOM. (B) Phylogenetically inferred maturation intermediates. Backbone ribbon representations are shown for HIV-1 gp120 (red) and the heavy chain variable domains (green). Critical intermediates inferred from the phylogenetic tree in (A) are labeled $I_{d45}$, $II_{d45}$, $III_{d45}$, $I_{d74}$ and $II_{d74}$. The number of $V_H$-gene mutations is provided (e.g. for the 23 mutations associated with the first intermediation of donor 45, "$I_{d45}$: 23"), and the location of these is highlighted in the surface representation and colored according to their chemistry.

FIGS. 22A-E depict an analysis of the heavy chain antibodyome of donor 74 and identification of heavy chains with HIV-1 neutralizing activity. Identity/divergence-grid analysis, cross-donor phylogenetic analysis, and CDR H3 analysis were coupled to functional characterization of selected heavy chain sequences. This provides a means for identification of novel heavy chains with HIV-1 neutralizing activity. (A) Identity/divergence-grid analysis. The location of the 63 synthesized IGHV1-2*02 heavy chains from donor 74 is shown, including neutralizing (red stars) and non-neutralizing (black stars) sequences. (B) Cross-donor phylogenetic analysis and CDR H3 lineage analysis. A maximum-likelihood tree of the 70 synthesized heavy chain sequences (including 7 non-IGHV1-2*02 sequences) is rooted at the putative reverted unmutated ancestor of VRC-PG04. The probe-identified VRC-PG and VRC-CH antibodies are shown in red text along with the 24 genomically identified heavy chain sequences, gVRC-H(1-24)$_{d74}$, which were found to neutralize HIV-1 when reconstituted with the light chain of VRC-PG04. Grid locations and CDR H3 classes are specified for neutralizing and non-neutralizing sequences. Within each CDR H3 class, all sequences with identical CDR H3s are highlighted in orange in the far right grids (with the number of total sequences corresponding to each CDR H3 class shown). (C) Expression levels of selected heavy chains reconstituted with the light chain of VRC-PG04 versus breadth of neutralization. (D) Neutralization potency of reconstituted cross-donor phylogeny-predicted antibodies on seven HIV-1 isolates. (E) CDR H3 analysis of donor 74 heavy chain sequences. For each of the 110,386 sequences derived from the IGHV1-2*02 allele, the CDR H3 was determined and its percent identity to that of the VRC-PG04 heavy chain was color coded as shown, and graphed. The sequences with high CDR H3 identity to VRC-PG04 reside in regions of high overall heavy chain sequence identity, even for sequences with a low divergence from IGHV1-2*02.

DETAILED DESCRIPTION

Figure 1:
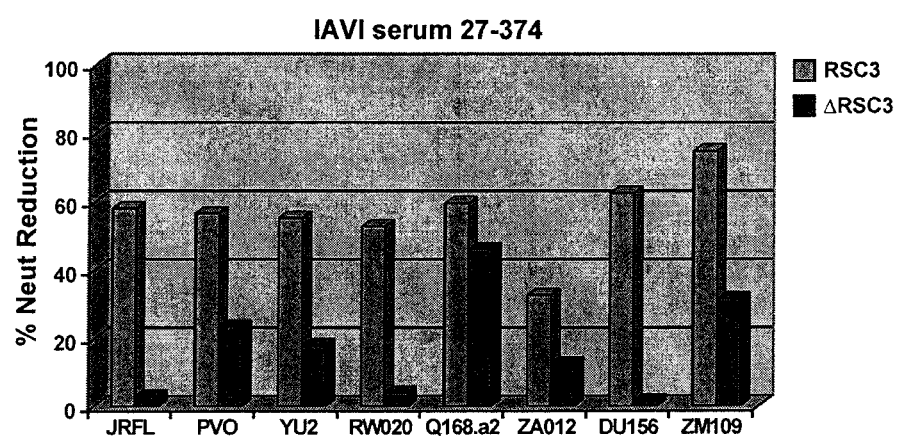
FIG. 1 depicts protein competition that shows that serum 27-374 has CD4bs directed neutralizing antibodies.

The present invention provides a novel method for isolating novel broad and potent neutralizing monoclonal antibodies against HIV. In particular, the search began with an IAVI-sponsored clinical study called Protocol G, a global hunt for new broadly neutralizing antibodies against HIV. Blood samples were collected from more than 1,800 HIV-positive people across the world. The method involves selection of a PBMC donor with high neutralization titer of antibodies in the plasma. B cells are screened for neutralization activity prior to rescue of antibodies. A process that more accurately predicted whether a given sample contained broadly neutralizing antibodies was developed and the samples were scored in terms of how many types of HIV they neutralized, and the top 10% were separated for further study. Novel neutralizing antibodies are obtained by emphasizing neutralization as the initial screen (see, e.g., Walker L, Phogat S, et al. Science. 2009; 326:285-9. Epub 2009 Sep. 3).

In an advantageous embodiment, the recombinant rescue of the monoclonal antibodies involves use of antigen-specific B-cell sorting as described by Wu et al (Science 329; 856 (2010)). To isolate CD4bs-directed mAbs, Applicants used a recently described method of antigen-specific memory B-cell sorting (Scheid et al., Nature 458, 636 (2009)), together with single cell PCR, to amplify IgG heavy and light chain genes from the cDNA of individual B cells (Scheid et al., Nature 458, 636 (2009), Wrammert et al., Nature 453, 667 (2008)). RSC3 and ΔRSC3 were expressed with a tagged amino acid sequence that allows biotin labeling (Wu et al., Science 329; 856 (2010)). The two proteins could thus be distinguished by FACS analysis after labeling with streptavidin (SA) conjugated to the fluorochromes allophycocyanin (SA-APC) or phycoerythrin (SA-PE), respectively. Peripheral blood mononuclear cells (PBMC) were incubated with RSC3 SA-APC and ΔRSC3 SA-PE, and single antigen-specific memory B cells were sorted into wells of a microtiter plate after selecting for memory B cells (CD19+, CD20+, IgG+) that bound to the RSC3 but not ΔRSC3 probe. RSC3-specific memory B cells were sorted and the matching heavy and light chain genes were successfully amplified from 12 cells. After cloning into IgG1 expression vectors that reconstituted the heavy and light chain constant regions, the full IgG mAbs were expressed.

In another embodiment, the recombinant rescue of the monoclonal antibodies involves use of a B cell culture system as described in Weitcamp J-H et al., J. Immunol. 171:4680-4688 (2003). Any other method for rescue of single B cells clones known in the art also may be employed such as EBV immortalization of B cells (Traggiai E., et al., Nat. Med. 10(8):871-875 (2004)), electrofusion (Buchacher, A., et al., 1994. AIDS Res. Hum. Retroviruses 10:359-369), and B cell hybridoma (Karpas A. et al., Proc. Natl. Acad. Sci. USA 98:1799-1804 (2001).

In some embodiments, monoclonal antibodies were rescued from the B cell cultures using variable chain gene-specific RT-PCR, and transfectant with combinations of H and L chain clones were screened again for neutralization and HIV antigen binding activities. mAbs with neutralization properties were selected for further characterization.

The antibodies of the present invention were identified according to these methods are disclosed by Wu et al, Science 329; 856 (2010). These antibodies were isolated from a human sample obtained through IAVI's Protocol G, and are referred to as VRC-PG-04 or VRC-PG-05—these antibodies neutralize HIV in vitro.

The invention is based on novel monoclonal antibodies and antibody fragments that neutralize HIV infection. In some embodiments, these monoclonal antibodies and antibody fragments have a particularly high potency in neutralizing HIV infection in vitro across multiple clades. Such antibodies are desirable, as only low concentrations are required in order to neutralize a given amount of virus. This facilitates higher levels of protection while administering lower amounts of antibody. Human monoclonal antibodies that secrete such antibodies are also included within the scope of the invention.

The invention also relates to various methods and uses involving the antibodies of the invention and the epitopes to which they bind.

The invention provides novel monoclonal or recombinant antibodies having particularly high potency in neutralizing HIV. The invention also provides fragments of these recombinant or monoclonal antibodies, particularly fragments that retain the antigen-binding activity of the antibodies, for example which retain at least one complementarity determining region (CDR) specific for HIV proteins. In this specification, by "high potency in neutralizing HIV" is meant that an antibody molecule of the invention neutralizes HIV in a standard assay at a concentration lower than antibodies known in the art.

The antibody molecule of the present invention may have concentrations of less than about 1 μg/ml, between about 1-10 μg/ml or greater than about 10 μg/ml to achieve 50% or 80% neutralization. In an exemplary embodiment, the antibody molecule of the present invention may have the concentrations of Table 4 which represent the monoclonal antibody concentration required to achieve 50% (Table 4A) or 80% (Table 4B) neutralization.

In another embodiment, the antibody molecule of the present invention may neutralize at a concentration of 0.16 μg/ml or lower (i.e. 0.15, 0.125, 0.1, 0.075, 0.05, 0.025, 0.02, 0.016, 0.015, 0.0125, 0.01, 0.0075, 0.005, 0.004 or lower), preferably 0.016 μg/ml or lower (an antibody concentration of 10-8 or lower, preferably 10-9 M or lower, preferably 10-10 M or lower, i.e. 10-11 M, 10-12 M, 10-13 M or lower). This means that only very low concentrations of antibody are required for 50% neutralization of a clinical isolate of HIV in vitro. Potency can be measured using a standard neutralization assay as described in the art.

The antibodies of the invention are able to neutralize HIV. Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

These antibodies can be used as prophylactic or therapeutic agents upon appropriate formulation, or as a diagnostic tool.

A "neutralizing antibody" is one that can neutralize the ability of that pathogen to initiate and/or perpetuate an infection in a host and/or in target cells in vitro. The invention provides a neutralizing monoclonal human antibody, wherein the antibody recognizes an antigen from HIV.

Preferably an antibody according to the invention is a novel monoclonal antibody referred to herein as VRC-PG-04 or VRC-PG-05. These antibodies were initially isolated from human samples obtained from IAVI's Protocol G. These antibodies have been shown to neutralize HIV in vitro.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The position of the CDR amino acids are defined according to the IMGT numbering system as: CDR1—IMGT positions 27 to 38, CDR2—IMGT positions 56 to 65 and CDR3—IMGT positions 105 to 117. (Lefranc, M P. et al. 2003 IMGT unique numbering for immunoglobulin and T cell receptor variable domains and Ig superfamily V-like domains. Dev Comp Immunol. 27(1):55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

The amino acid sequences of the CDR3 regions of the light and heavy chains of the antibodies are shown in FIG. 8.

As used herein, a neutralizing antibody may inhibit the entry of HIV-1 virus with a neutralization index >1.5 or >2.0. Broad and potent neutralizing antibodies may neutralize greater than about 50% of HIV-1 viruses (from diverse clades and different strains within a clade) in a neutralization assay.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J. Virol. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

The neutralization index may be expressed as the ratio of normalized relative luminescence units (RLU) of the test viral strain to that of a control virus derived from the same test B cell culture supernatant. The cut-off values used to distinguish neutralizing hits may be determined by the neutralization index of a large number of "negative control wells" containing B cell culture supernatants derived from healthy donors. Such a method was successful for the isolation and characterization of PG9 and PG16.

The method of U.S. Pat. No. 7,386,232 may also be utilized for the screening of broad neutralizing antibodies. An envelope-enzyme fusion protein may be constructed by attaching an enzyme to the C-terminal end of an envelope protein. Virus particles which may comprise the fusion protein and wild type and/or soluble envelope glycoprotein may be generated and used to infect target cells in the presence of a patients' sera. Activities of enzyme measured in such infected cells are measures of virus binding and entry to the target cells that are mediated by the wild type viral envelope protein. Examples of enzymes that can be used to generate the fusion protein include, but are not limited to, luciferase, bacterial or placental alkaline phosphatase, β-galactosidase, and fluorescent proteins such as Green fluorescent protein or toxins. The assay, in general, can also be carried out in 96-well plate. Decreased enzyme activities in the presence of the sera indicate that there are neutralizing antibodies in the sera.

In an advantageous embodiment, VRC-PG-04 and VRC-PG-05 were isolated using antigen specific B-cell sorting and PCR amplification of heavy and light chain genes as described by Wu et al (Science 329; 856 (2010)). Epitope specific protein probes (RSC3) and knock out mutant (delta RSC3) were utilized as described by Wu et al (Science 329; 856 (2010)).

In another embodiment to isolate CD4bs-directed mAbs, a method of antigen-specific memory B-cell sorting (Wu et al (Science 329; 856 (2010))), together with single cell PCR, to amplify IgG heavy and light chain genes from the cDNA of individual B cells (J. F. Scheid et al., Broad diversity of neutralizing antibodies isolated from memory B cells in HIV-infected individuals. Nature 458, 636 (2009) and J. Wrammert et al., Nature 453, 667 (2008)) is preferred. Mutant Env probes are expressed with a tagged amino acid sequence that allows biotin labeling to distinguish them by FACS analysis after labeling with streptavidin (SA) conjugated to the fluorochromes allophycocyanin (SA-APC) or phycoerythrin (SA-PE), respectively. Peripheral blood mononuclear cells (PBMC) from a donor are incubated with the labeled mutant Env probes, and single antigen-specific memory B cells were sorted into wells of a microtiter plate after selecting for memory B cells (CD19+, CD20+, IgG+) that bind to the reference probe. The reference-probe-specific memory B cells are sorted and the matching heavy and light chain genes are amplified. After cloning into IgG1 expression vectors that reconstitute the heavy and light chain constant regions, the full IgG mAbs are expressed.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen which may comprise such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection.

Compounds which have a chemical structure selected using the invention, wherein said compounds are neutralizing antibody binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')2, the fragment of the antibody that can be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

An "antibody fragment" may comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antibodies of the present invention may be used in vitro (such as using cell-free expression systems) and/or in cultured cells grown in vitro in order to produce the encoded HIV-antibodies which may then be used for various applications such as in the production of proteinaceous vaccines. For such applications, any vector that allows expression of the antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antibodies of the invention can be expressed.

For example, when the aim is to express the antibodies of the invention in vitro, or in cultured cells, or in any prokaryotic or eukaryotic system for the purpose of producing the protein(s) encoded by that antibody, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies under the identified circumstances.

In an advantageous embodiment, IgG1 expression vectors may be utilized to reconstitute heavy and light chain constant regions if heavy and light chain genes of the antibodies of the present invention are cloned.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if the aim is to express the HIV-1 antigens in cells in order to produce and isolate the expressed proteins, such as from cells grown in culture. For expressing the antibodies in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies can be carried out in any suitable type of host cells, such as bacterial cells, yeast, insect cells, and mammalian cells. The antibodies of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. In preferred embodiments the subject is a human, for example a human that is infected with, or is at risk of infection with, HIV-1.

The term "pharmaceutical composition" is used herein to define a solid or liquid composition in a form, concentration and level of purity suitable for administration to a patient (e.g. a human patient) upon which administration it can elicit the desired physiological changes. The terms "immunogenic composition" and "immunological composition" and "immunogenic or immunological composition" cover any composition that elicits an immune response against the targeted pathogen, HIV. Terms such as "vaccinal composition" and "vaccine" and "vaccine composition" cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response which can, but need not, be a protective immune response. An immunogenic or immunological composition can be used in the treatment of individuals infected with the pathogen, e.g., to stimulate an immune response against the pathogen, such as by stimulating antibodies against the pathogen. Thus, an immunogenic or immunological composition can be a pharmaceutical composition. Furthermore, when the text speaks of "immunogen, antigen or epitope", an immunogen can be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc, of an antibody that binds to the compound or an immunogen, antigen or epitope that binds to the antibody; for instance, an anti-HIV antibody or an HIV immunogen, antigen or epitope.

For such in vivo applications the nucleotide sequences, antibodies of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies of the invention to a subject, such as a human, such that the antibodies are then expressed in the subject to elicit an immune response.

The present invention also relates to methods of immunizing or reducing the effect of an HIV infection or an HIV related disease which may comprise identifying a patient in need of such treatment, and administering to said patient a therapeutically effective amount of at least one antibody of the present invention. The method may additionally comprise the administration of a second therapeutic agent. The second therapeutic agent may be an anti-viral agent. The anti-viral agent may be Abacavir, Aciclovir, Adefovir, Amantadine, Amprenavir, Ampligen, Aplaviroc, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon (e.g., type I, II or III), Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Vicriviroc, Zalcitabine, Zanamivir (Relenza) or Zidovudine or a combination thereof.

The present invention also relates to methods of immunizing or reducing the effect of an HIV infection or an HIV related disease which may comprise identifying a patient in need of such treatment and administering to said patient a therapeutically effective amount of: a first antibody of the present invention, or fragment thereof, specific for a first epitope which binds to said first antibody and a second antibody of the present invention, or fragment thereof, specific for a second epitope which binds to said second antibody. In one embodiment, the first antibody may be VRC-PG-04 or VRC-PG-05. In another embodiment, the second antibody may be VRC-PG-04 or VRC-PG-05. In yet another embodiment, the second antibody may be VRC01, VRC02, VRC03, VRCCH30, VRCCH31, VRCCH32, VRCCH33 or VRCCH34.

Identifying a patient in need of treatment for an HIV infection or an HIV related disease is known to one of skill in the art. A patient in need of treatment for an HIV infection or an HIV related disease may also be identified by detecting HIV. In particular, HIV may be detected by an HIV test such as an antibody test (e.g., ELISA or western blot) for HIV and/or a nucleic acid test (e.g., RT-PCR). Generally, infection with HIV-1 is associated with a progressive decrease of the $CD4^+$ T cell count and an increase in the level of HIV in the blood. The stage of infection may be determined by measuring the patient's $CD4^-$ T cell count and viral load.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof; buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylenepolyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO4)2$, $AlNa(SO4)2$, $AlNH(SO4)2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057, 540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689, 338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention in the immunogenic composition of the invention can be readily determined by those of skill in the art. For example, the dosage of the antibodies can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably which may comprise an adenovirus vector containing DNA encoding one or more of the antibodies of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration)

of administration, as well as dosages can be determined taking into consideration such factors as the age, sex, weight, species and condition of the particular subject, and the route of administration.

The immunogenic compositions of the invention can be administered alone, or can be co-administered, or sequentially administered, with other therapeutic agents, thereby providing multivalent or "cocktail" or combination compositions of the invention and methods of employing them. The therapeutic agent can be an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

The invention will now be further described by way of the following non-limiting examples.

EXAMPLES

Example 1

Use of RSC3 and RSC3 Mutant Probes to Isolate Two New Neutralizing Monoclonal Antibodies from IAVI Protocol G Donor PBMC The Protocol G serum and PBMC analysis was performed as follows. A set of 12 broadly neutralizing sera was first analyzed by resurfaces stabilized core (RSC3) ELISA for evidence of CD4 binding site (CD4bs) directed antibodies. Positive sera was further analyzed in competition neutralization assay using RSC3 to block serum neutralization. This demonstrated that sera have neutralizing antibodies (NAbs) to the CD4bs. Four out of twelve (4/12) sera had evidence of CD4bs directed neutralization; one was chosen for mAb isolation (VRC code was IAVI#2, corresponding to IAVI sample #27-374).

Monoclonal antibody isolation method was performed as follows. The method used was essentially the same as described in Wu et al, Science 329; 856 (2010). PBMC were incubated with RSC3 and ΔRSC3 to find B-cells reactive with RSC3 and not ΔRSC3; Single B-cells sorted into 96 well plates. Antibody heavy and light chain variable region genes amplified by PCR and cloned into expression vectors (one for heavy and one for light) and full IgG expressed.

FIG. 1 depicts protein competition that shows that serum 27-374 has CD4bs directed neutralizing antibodies. Neutralization by IAVI serum 27-374 against a panel of viruses shown on x-axis. Bars show the % reduction in neutralization for each virus when the RSC3 protein is added as a competitor. The ΔRSC3 is a knock out mutant. Data show that ~50% of the serum neutralization against each virus could be blocked by RSC3—indicating the presence of CD4bs directed neutralizing antibodies.

Figure 2:
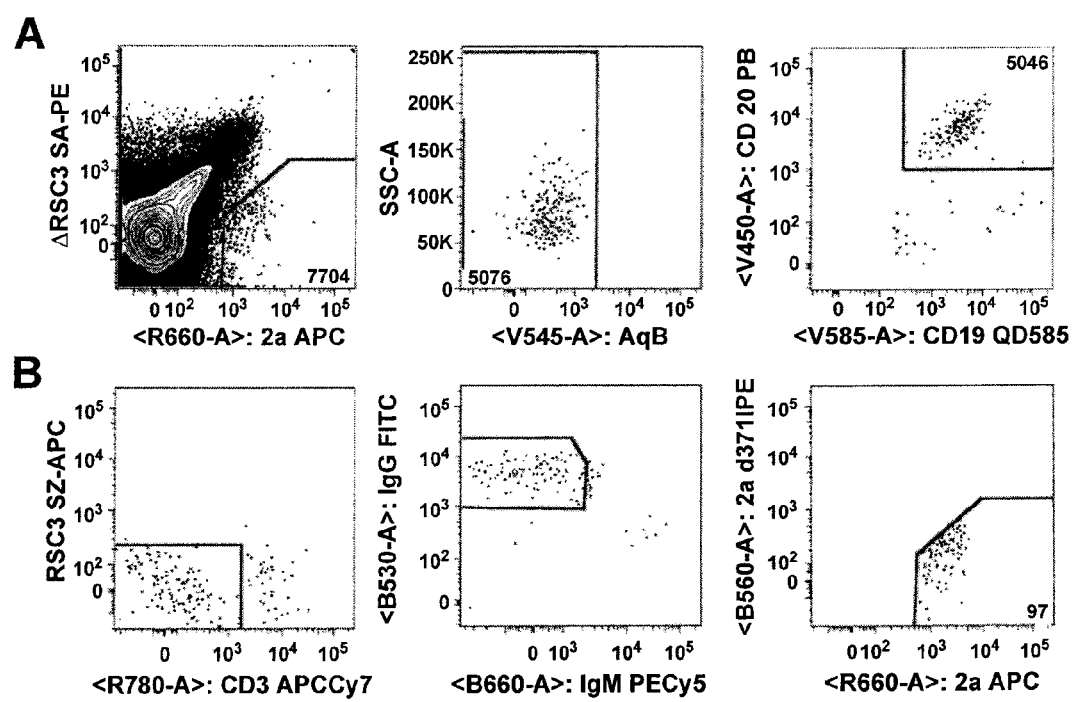
FIGS. 2A-B depict single cell sort for RSC3 reactive B-cells.

FIG. 2 depicts single cell sort for RSC3 reactive B-cells, in particular a sort profile from donor PBMC: 27-374. Schema for isolating the specific B-cells that produced VRC-PG-04 and VRC-PG-05. Donor PBMC were incubated with wild type form of cloak-2a protein and the Δ371 mutant protein. The RSC3 protein is highly specific for anti-CD4-binding site antibodies; the mutant does not bind such antibodies. Both proteins are biotin labeled and then labeled with different color fluorochromes. Flow cytometry was performed to isolate memory B-cells and to further identify B-cells that bind RSC3, and not the A 371 mutant (0.075% of memory B-cells). These B-cells were deposited as a single cell per well, into 96-well plates.

Figure 3:
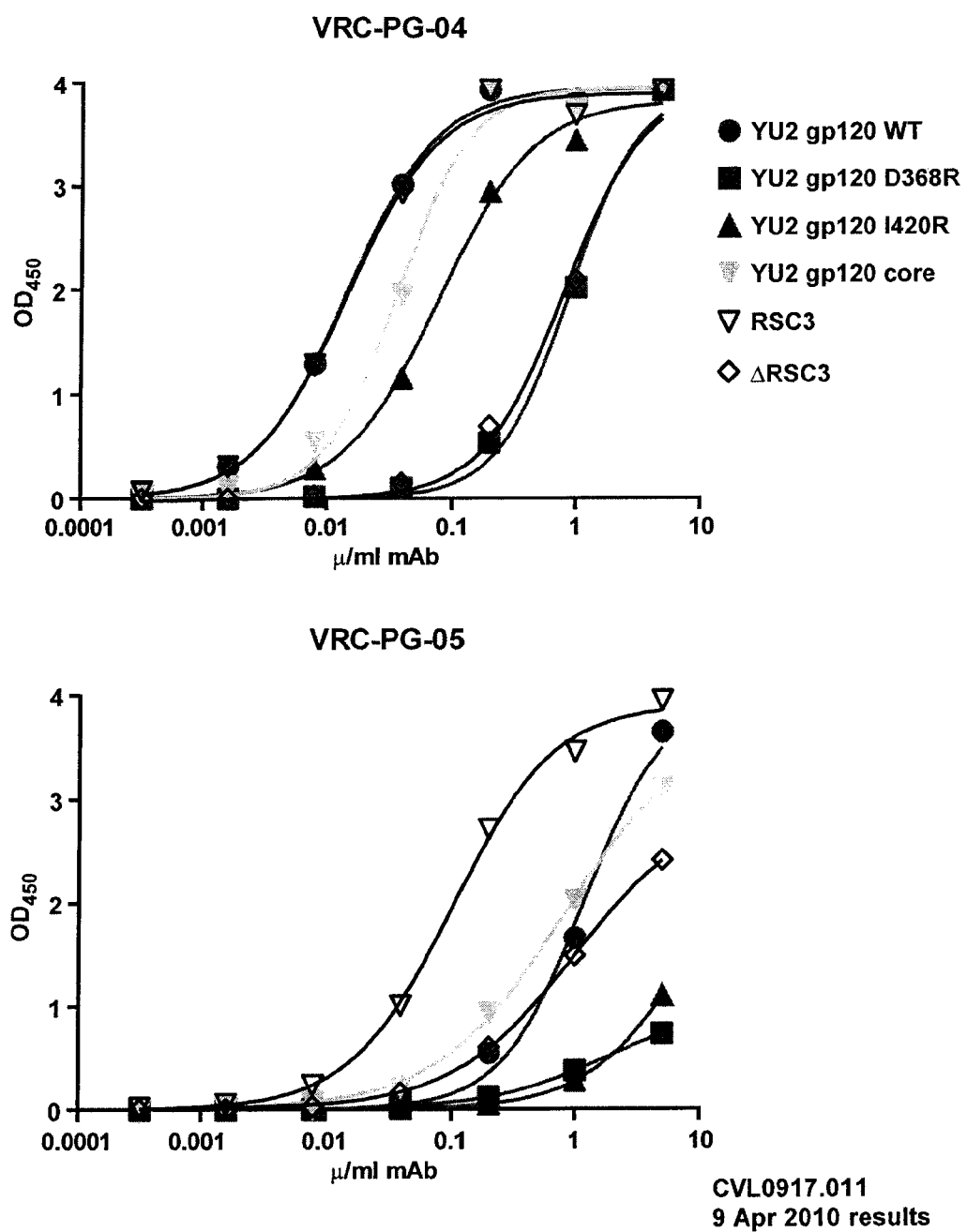
FIG. 3 depicts ELISA Binding of VRC-PG-04 and VRC-PG-05 to several mutant versions of YU2 gp120 and to the resurfaced stabilized core (RSC3) proteins and its knock out mutant ΔRSC3.

FIG. 3 depicts ELISA Binding of VRC-PG-04 and VRC-PG-05 to several mutant versions of YU2 gp120 and to the resurfaced stabilized core (RSC3) proteins and its knock out mutant ΔRSC3. ELISA data showed that VRC-PG04 binds well to gp120 and to RSC3, with reduced binding to the CD4bs knock out mutants of those two proteins. Therefore, it is likely directed to the CD4bs of gp120. VRC-PG-05 bound better to RSC3 than to gp120, thus its epitope appears to be distinct from VRC-PG-04.

Figure 4:
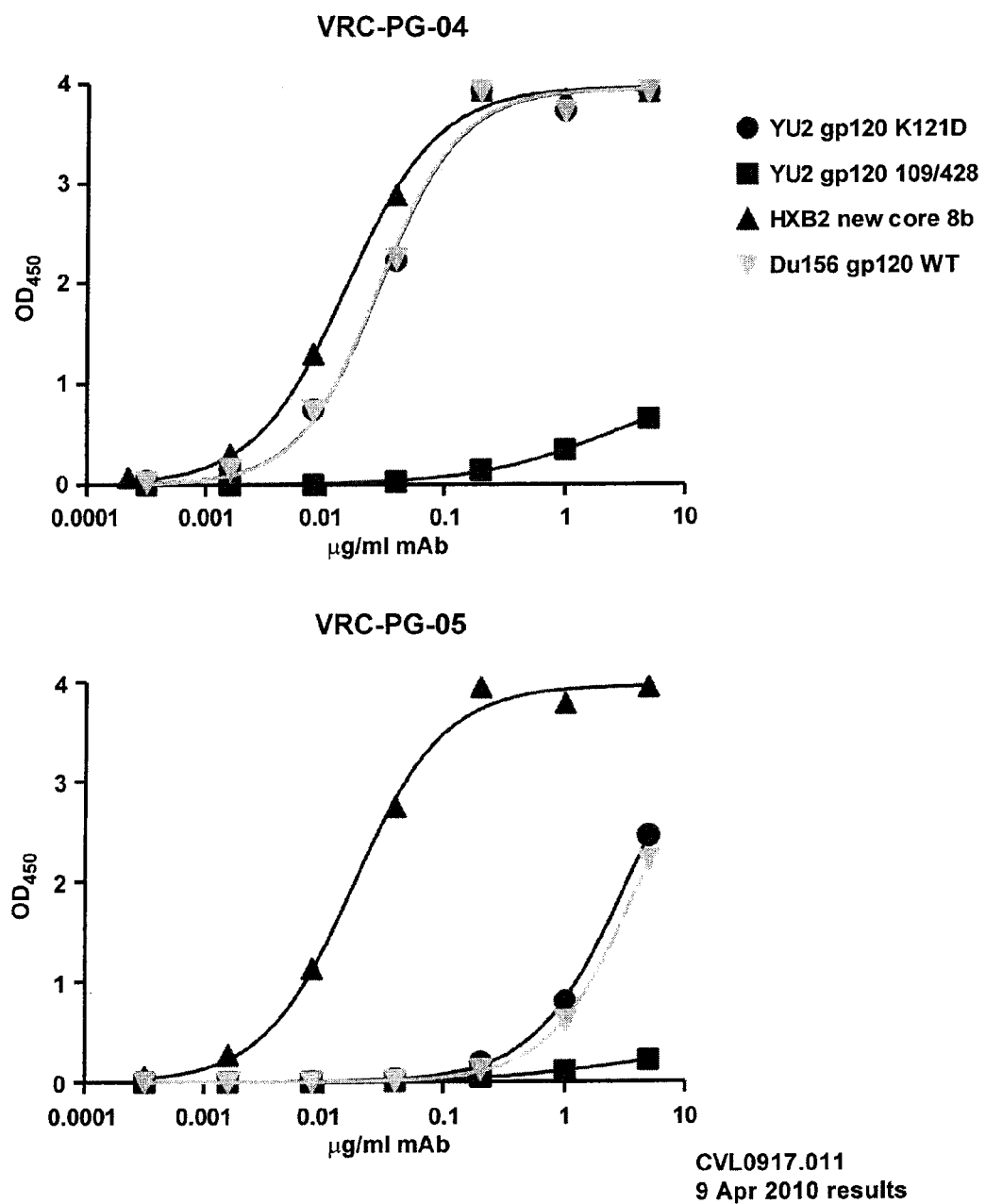
FIG. 4 depicts binding of VRC-PG-04 and VRC-PG-05 to YU2 gp120-based proteins, HXB2 new core 8b and Du156 gp120 WT by ELISA.

FIG. 4 depicts binding of VRC-PG-04 and VRC-PG-05 to YU2 gp120-based proteins, HXB2 new core 8b and Du156 gp120 WT by ELISA. VRC-PG-05 binds well to the HXB2 gp120 new core (right graph) indicating that its epitope lies within the core of gp120, but is different from. VRC-PG-04 which binds strongly to the clade C Du156 gp120 whereas VRC-PG-05 binds only weakly.

Figure 5:
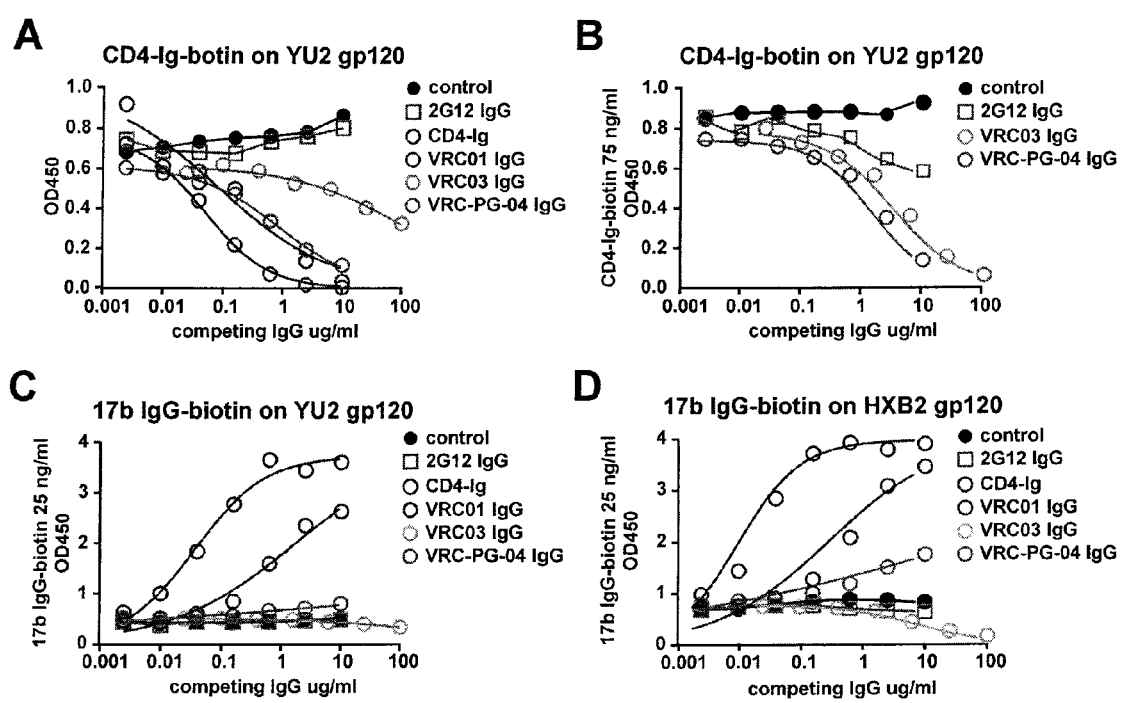
FIGS. 5A-D depict competition ELISA demonstrating that VRC-PG-04 is directed against CD4bs.

FIG. 5 depicts competition ELISA demonstrating that VRC-PG-04 is directed against CD4bs. Data are competition ELISAs on either YU2 gp120 (left graphs) or HxB2 gp120 (right graphs). Top graphs show binding of CD4-Ig in the presence of several other IgG mAbs. Bottom graphs show binding of 17b in the presence of other mAbs. The previously published VRC01 and VRC03 mAbs are included (Wu et al, Science 329; 856 (2010)). VRC-PG-04 cross competes with CD4-Ig and with VRC01—showing it is likely directed to the CD4bs of gp120. Bottom graphs show that VRC-PG-04 does not potentiate 17b binding on YU2 gp120, though it mildly potentiates 17b binding to HxB2 gp120.

Figure 6:
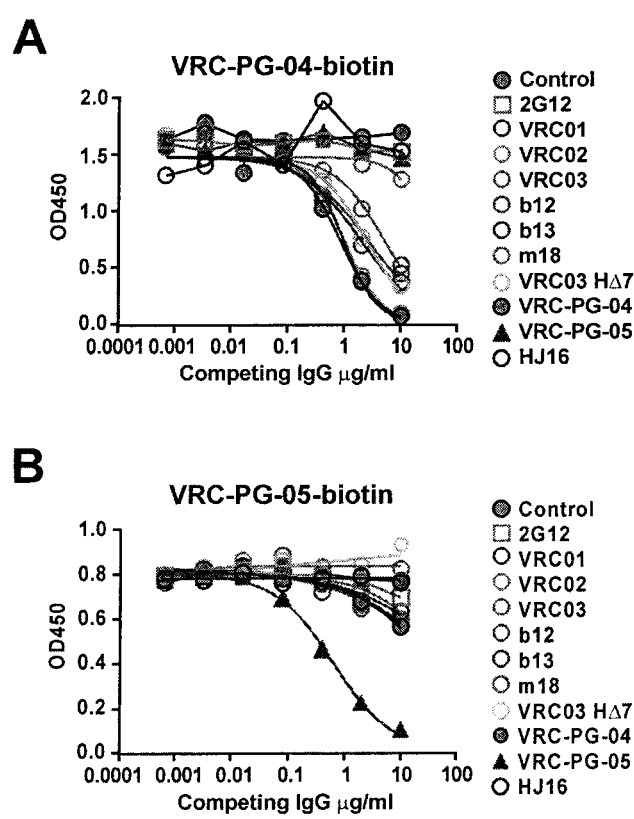
FIGS. 6A-B depict competition ELISA demonstrating that VRC-PG-04, but not VRC-PG-05, is cross competed by CD4bs antibodies ELISAs done with RSC3 on plate.

FIG. 6 depicts competition ELISA demonstrating that VRC-PG-04, but not VRC-PG-05, is cross competed by CD4bs antibodies ELISAs done with RSC3 on plate. Competition ELISA with RSC3 protein on plate. Top graph shows that VRC-PG-04 is cross blocked by other mAbs directed to the CD4bs. In contrast, VRC-PG-05 is not cross blocked by mAbs directed to the CD4bs, indicating it is directed against a different epitope on the core protein of gp120. The previously published VRC01, VRC02 and VRC03 mAbs (Wu et al, Science 329; 856 (2010)) are included for comparison.

Figure 7:
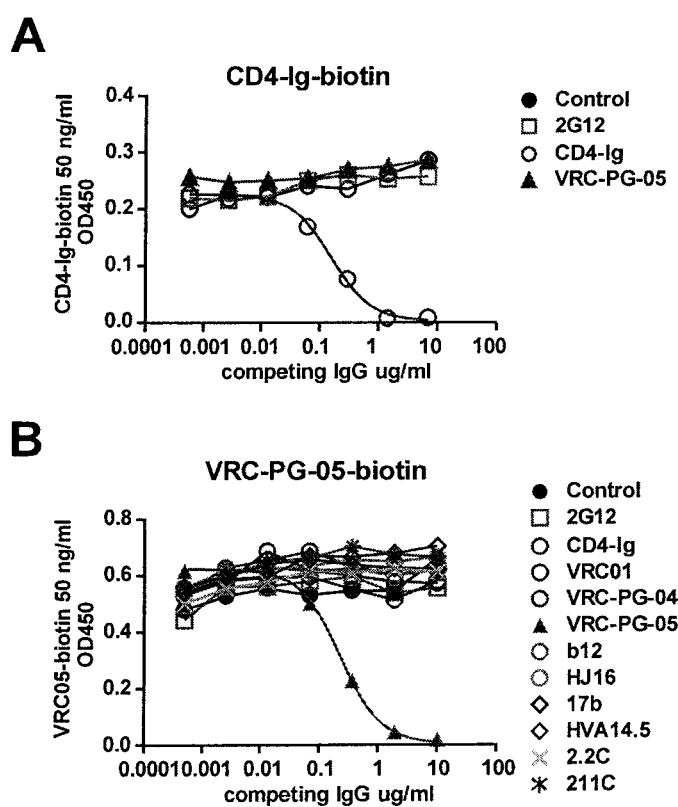
FIGS. 7A-B depict competition ELISA using clade B AC10.29 gp1120 on plate and that VRC-PG-05 does not cross-block CD4bs mAbs.

FIG. 7 depicts competition ELISA using clade B AC10.29 gp1120 on plate and that VRC-PG-05 does not cross-block CD4bs mAbs. Competition ELISA with strain AC10.29 gp120 protein on plate. The top graph shows that CD4-Ig is cross blocked by itself, but not by VRC-PG-05. The bottom graph shows the VRC-PG-05 is cross blocked by itself, but not by any of the other mAbs tested. Thus, VRC-PG-05 binds to a unique epitope on gp120. The previously published VRC01, VRC02 and VRC03 mAbs (Wu et al, Science 329; 856 (2010)) are included for comparison.

Table 1 depicts a gene family analysis of VRC-PG-04 and VRC-PG-05 compared to mAbs b12, VRC01, VRC02 and VRC03. The previously published VRC01, VRC02 and VRC03 mAbs (Wu et al, Science 329; 856 (2010)) are included for comparison. The table shows the inferred germline V, D and J genes for the heavy chain and the V and J genes for the kappa light chain. VRC-PG-04 and VRC-PG-05 are heavily mutated from germline.

TABLE 1

Repertoire and mutation analysis of VRC mAbs.

Heavy Chain

| | IGHV | IGHD | IGHJ | CDR3 length (amino acids) | VH mutation frequency (nucleotides) |
|---|---|---|---|---|---|
| VRC01 | 1-02*02 | 3-16*01 (or *02) | 1*01 | 14 | 91/288 (32%) |
| VRC02 | 1-02*02 | 3-16*01 (or *02) | 1*01 | 14 | 92/288 (32%) |
| VRC03 | 1-02*02 | IGHD3 family | 1*01 | 16 | 85/288 (30%) |
| b12 | 1-03*01 | 3-10*02 | 6*03 | 20 | 39/288 (13%) |
| VRC-PG-04 | 1-02*02 | 2-8*02 | 2*01 | 16 | 84/288 (29%) |
| VRC-PG-05 | 3-7*01 | 3-3*01 | 3*02 | 19 | 27/288 (9%) |

Light Chain

| | IGKV | IGKJ | CDR3 length (amino acids) | VL mutation frequency (nucleotides) |
|---|---|---|---|---|
| VRC01 | 3-11*01 | 2*01 | 5 | 45/264 (17%) |
| VRC02 | 3-11*01 | 2*01 | 5 | 49/264 (19%) |
| VRC03 | 3-20*01 | 2*01 | 5 | 53/267 (20%) |
| b12 | 3-20*01 | 2*01 | 9 | 35/267 (13%) |
| VRC-PG-04 | 3-20*01 | 5*01 | 5 | 51/267 (19%) |
| VRC-PG-05 | 4-1*01 | 2*03 | 8 | 21/297 (7%) |

FIG. 8 depicts sequence alignments of VRC-PG-04 and VRC-PG-05 compared to their inferred germline sequence. The previously published VRC01, VRC02 and VRC03 mAbs (Wu et al, Science 329; 856 (2010)) are included for comparison.

Example 2

VRC-PG-04 Isolation

A novel monoclonal antibody, VRC-PG-04, was isolated from an HIV+ donor using an antigenically resurfaced, stabilized gp120 glycoprotein probe that was specific for the CD4 binding site. VRC-PG-04 competed with CD4-IgG for binding to gp120, demonstrating that VRC-PG-04 is directed against the CD4bs. This antibody is potent and broadly neutralizing, having a mean IC50 of 0.172 µg/ml and being able to neutralize a wide range of pseudovirus entry into TZM-bl cells, including pseudovirus from clade A—87% (n=24), B—96% (n=26), and C—79% (n=34).

To further characterize the Ab, neutralization of entry assays were carried out using a panel of JRCSF gp120 single alanine mutants incorporated into pseudovirus. Applicants found that neutralization of entry by VRC-PG-04 was knocked out (as defined by having less than 10% neutralization potency compared to wildtype) by a single mutation in aa D279 (see Neutralization Potency chart). Applicants next determined which residues were important for Ab binding to gp120. Applicants found binding of VRC-PG-04 to several gp120 glycoproteins isolated from pseudovirus bearing mutant JRSCF gp120s was drastically decreased as measured by ELISA. In particular, these residues were found in V1N2 stem (N197), C2 (N276, D279, N280), C3 (I371), and C4 (T450, R456). In Applicants' preliminary screen, there seem to be less residues involved in knocking out binding (as defined by having less than 10% apparent affinity to gp120 compared to wildtype) of VRC-PG-04 to gp120 when compared to the number of residues involved in knocking out binding to gp120 of b12 or CD4 (see Table 2, binding chart).

TABLE 2

Binding chart

| Domain | Mutant | Apparent Affinity | | | |
|---|---|---|---|---|---|
| | | pub b12 | pub CD4 | 2G12 | VRC-PG-04 |
| | E87A | 7 | 114 | | 53 |
| | M95A | 75 | 59 | | 41 |
| C1 | K97A | 134 | 50 | | 98 |
| | E102A | 63 | 47 | | 50 |
| | W112A | 2 | 67 | | 76 |
| | D113A | 1 | 9 | 169 | 70 |
| | V120A | | | | 79 |
| | K121A | 4 | 3 | | 130 |
| C1 | L122A | 27 | 62 | | 96 |
| (V1/V2-stem) | T123A | 233 | 42 | | 113 |
| | L125A | 383 | 23 | | 93 |
| | V127A | 62 | 26 | | 22 |
| | N156A | | | | 72 |
| | N160K | | | | 390 |
| | T162A | | | | 83 |
| | I165A | 20 | 57 | | 139 |
| | R166A | 52 | 44 | | 97 |
| | D167A | | | | 97 |
| | K168A | | | | 34 |
| | K171A | 118 | 26 | | 78 |
| | E172A | 143 | 93 | | 74 |
| V2 | F176A | 2 | 19 | 400 | 104 |
| | Y177A | | | | 87 |
| | L179A | | | | 138 |
| | D180A | 1 | 31 | | 52 |
| | V182A | | | | 54 |
| | I184A | 0.6 | 27 | | 27 |
| | D185A | 6 | 62 | | 55 |
| | T190A | 21 | 187 | | 42 |
| | K194S | | | | 22 |
| | N197A | 25 | 3 | 318 | 10 |
| C2 | T198A | 0.1 | 42 | | 49 |
| (V1/V2-stem) | S199A | 123 | 4 | | 78 |
| | T202A | 220 | 62 | | 58 |
| | K207A | 2 | 5 | 100 | 31 |
| | F210A | 77 | 37 | | 85 |
| | I213A | 20 | 31 | 114 | 28 |
| | R252A | 17 | 47 | | 111 |
| | S256A | 13 | 47 | 108 | 37 |
| | T257A | 28 | 21 | 133 | 51 |

TABLE 2-continued

Binding chart

| Domain | Mutant | Apparent Affinity | | |
|---|---|---|---|---|
| | | pub b12 | pub CD4 | 2G12 |
| C2 | N262A | 6 | 5 | 17 |
| | R273A | 0.9 | 40 | 78 |
| | N276A | 225 | 27 | 169 |
| | D279A | 27 | 33 | 1 |
| | N280A | 75 | 44 | 0 |
| | K282A | 32 | 78 | 23 |
| | T283A | 55 | 53 | 85 |
| | N295A | | | 34 |
| | T297S | | | 115 |
| V3 (base) | P299A | | | 115 |
| | N301A | | | 43 |
| | N302A | | | 40 |
| V3 (stem) | R304A | | | 38 |
| | K305A | | | 51 |
| | S306A | | | 93 |
| | R456A | 6 | 53 | 8 |
| | D457A | 5 | 2 | |
| | G458A | 300 | 2 | |
| | G459A | 54 | 37 | 61 |
| | N461A | 4 | 160 | 285 |
| | E462A | 21 | 32 | 178 |
| | S463A | 50 | 53 | 324 |
| V5 | I467A | 63 | 3 | |
| | R469A | 1.4 | 8 | |
| | P470A | 1.3 | 13 | 100 |
| | G471A | 37 | 89 | 137 |
| | G472A | 22 | 2 | 100 |
| | G473A | 998 | 2 | |
| | D474A | 91 | 22 | |
| C5 | M475A | 130 | 64 | |
| | R476A | 25 | 40 | 133 | 81 |
| | D477A | 2 | 187 | | 44 |
| | W479A | 1.3 | 19 | 40 | 95 |
| | R480A | 37 | 73 | | |
| | Delta V1 | 35 | 44 | 133 | |
| V1-V3 | Delta V1/2 | 30 | 12 | 114 | |
| | Delta V3 | 30 | 41 | | | apparent affinity relative to WT = (apparent affinity for WT/apparent affinity for mutant) * 100
note:
graph adapted from Pantophlet et al., 2003.

TABLE 3

Neutralization Potency chart.
The previously published VRC01 and VRC03 mAbs
(Wu et al., Science 329; 856 (2010)) are included for comparison.

| gp120 domain | mutation | Neutralization potency relative to WT (%) | | | |
|---|---|---|---|---|---|
| | | CD4 | b12 | VRC01 | VRC03 |
| | | | | | VRC-PG-04 |
| C1 | E87A | 46 | 29 | 63 | 106 | 118 |
| | M95A | 17 | 48 | 56 | 79 | 107 |
| | K97A | 184 | 117 | 62 | 108 | 130 |
| | E102A | 60 | 83 | 98 | 112 | 146 |
| | W112A | 100 | 119 | 78 | 111 | 118 |
| C1 (V1/V2 stem) | V120A | 161 | 80 | 60 | 101 | 84 |
| | K121A | 28 | 30 | 24 | 69 | 78 |
| | L122A | 474 | 96 | 66 | 51 | 106 |
| | T123A | | | | | 121 |
| | L125A | 9532 | 1549 | 222 | 29 | 89 |
| | N156A | | 2345 | 68 | 30 | 454 |
| | N160K | 99 | 173 | 296 | 173 | 176 |

TABLE 3-continued

Neutralization Potency chart.
The previously published VRC01 and VRC03 mAbs
(Wu et al., Science 329; 856 (2010)) are included for comparison.

| gp120 domain | mutation | Neutralization potency relative to WT (%) | | | |
|---|---|---|---|---|---|
| | | CD4 | b12 | VRC01 | VRC03 | PGV04 |
| V2 | T162A | 318 | 107 | 190 | 21 | 177 |
| | I165A | 434 | 41 | 42 | 10 | 61 |
| | R166A | 22 | 41 | 42 | 31 | 51 |
| | D167A | 702 | 121 | 99 | 23 | 81 |
| | K168A | 106 | 80 | 50 | 50 | 67 |
| | K171A | 52 | 58 | 60 | 132 | 149 |
| | E172A | 259 | 55 | 161 | 34 | 59 |
| | Y177A | | 2416 | 89 | 1 | 135 |
| | L179A | 1526 | 19 | 13 | 25 | 88 |
| | V182A | 128 | 45 | 60 | 76 | 68 |
| | I184A | 806 | 172 | 129 | 94 | 155 |
| | D185A | 96 | 4 | 34 | 88 | 120 |
| | T190A | 8 | 165 | 119 | 120 | 82 |
| C2 (V1/V2 stem) | K194S | 1502 | 4100 | 1538 | 906 | 236 |
| | T198A | 218 | 5 | 40 | 22 | 95 |
| | S199A | 2903 | 5973 | 724 | 145 | 707 |
| | T202A | 3831 | 569 | 30 | 3 | 61 |
| C2 | F210A | 845 | 384 | 163 | 62 | 101 |
| | I213A | 102 | 178 | 174 | 186 | 185 |
| | R252A | 21 | 98 | 68 | ND | 86 |
| | S256A | 112 | 83 | 73 | 136 | 152 |
| | T257A | 5 | 107 | 253 | 86 | 148 |
| | N262A | 63 | 443 | 223 | 12 | 105 |
| | R273A | 132 | 109 | 48 | 72 | 120 |
| | N276A | 29 | 134 | 341 | 536 | 18 |
| | D279A | 2 | 92 | 3 | 0.5 | 0.4 |
| | K282A | 5 | 78 | 363 | 99 | 81 |
| | T283A | 5 | 717 | 346 | 99 | 225 |
| V3 (base) | N295A | 46 | 85 | 56 | 97 | 97 |
| | T297S | 17 | 47 | 50 | 137 | 179 |
| | P299A | | 4882 | 80 | 0.50 | 115 |
| | N301A | 8163 | 1396 | 239 | 22 | 507 |
| V3 (stem) | N302A | 28 | 75 | 43 | 110 | 120 |
| | R304A | 4497 | 125 | 32 | 0.5 | 43 |
| | K305A | | 3466 | 70 | 0.5 | 54 |
| | | | | | | PGV04 |
| V3 (tip) | S306A | 246 | 94 | 76 | 7 | 130 |
| | I307A | | 7399 | 119 | 1 | 20 |
| | H308A | 505 | 76 | 66 | 4 | 99 |
| | I309A | | 3493 | 82 | 1 | 31 |
| | P313A | 3 | 13 | 130 | 55 | 111 |
| | R315A | 393 | 67 | 45 | 14 | 92 |
| | F317A | | 4709 | 116 | 1 | 37 |
| | Y318A | | 4846 | 109 | 1 | 27 |
| | T319A | 316 | 54 | 56 | 34 | 102 |
| | T320A | | 1240 | 56 | 2 | 64 |
| V3 (base) | E322A | 293 | 76 | 110 | 26 | 83 |
| | D325A | 444 | 154 | 53 | 26 | 112 |
| | N332A | 118 | 143 | 119 | 73 | 120 |
| C3 | Q337A | 20 | 56 | 43 | 53 | 172 |
| | K343A | 34 | 65 | 45 | 92 | 117 |
| | R350A | 21 | 76 | 60 | 38 | 106 |
| | S365A | 32 | 70 | 114 | 85 | 155 |
| | P369A | 26 | 30 | 72 | 86 | 113 |
| | V372A | 12 | 12 | 74 | 20 | 125 |
| | M373A | 37 | 124 | 90 | 20 | 135 |
| | Y384A | | | | | 69 |
| | N386A | 50 | 392 | 212 | 79 | 120 |
| | T388A | 110 | 482 | 196 | 15 | 160 |
| V4 | N392Q | 29 | 63 | 44 | 62 | 73 |
| | W395A | | | | | 95 |
| C4 | R419A | 596 | 30 | 120 | 17 | 111 |
| | I420A | 1015 | 344 | 16 | 1 | 21 |
| | K421A | | 1457 | 64 | 1 | 68 |
| | Q422A | 5369 | 657 | 47 | 14 | 98 |
| | I423A | | 3412 | 19 | 1 | 24 |

TABLE 3-continued

Neutralization Potency chart.
The previously published VRC01 and VRC03 mAbs
(Wu et al., Science 329; 856 (2010)) are included for comparison.

| gp120 domain | mutation | Neutralization potency relative to WT (%) | | | |
|---|---|---|---|---|---|
| | | CD4 | b12 | VRC01 | VRC03 |
| | I424A | | 2301 | 26 | 1 | 142 |
| | N425A | 22 | 98 | 61 | 34 | 148 |
| | V430A | | 4336 | 36 | 1 | 765 |
| | K432A | 147 | 61 | 55 | 30 | 101 |
| | Y435A | 3407 | 2034 | 31 | 1 | 73 |
| | I439A | 2854 | 656 | 162 | 1508 | 339 |
| | T450A | 31 | 126 | 84 | 115 | 135 |
| | T455A | 22 | 27 | 79 | ND | 142 |
| | R456A | 55 | 106 | 63 | 1 | 259 |
| | G459A | 722 | 69 | 149 | 1 | 239 |
| V5 | N461A | 97 | 90 | 363 | 496 | 321 |
| | E462A | 38 | 49 | 46 | 106 | 116 |
| | S463A | 54 | 109 | 536 | 296 | 461 |
| | G471A | 10 | 70 | 25 | 96 | 92 |
| C5 | D474A | 11 | 109 | 32 | 8 | 102 |
| | M475A | 61 | 59 | 68 | 55 | 140 |
| | R476A | 5 | 129 | 200 | 26 | 141 |
| | D477A | 10 | 158 | 68 | 10 | 107 |
| | W479A | 70 | 508 | 160 | 51 | 138 |
| | R480A | 53 | 150 | 200 | 51 | 113 | blue = 1-10%
green = 11-40%
yellow = 250-10,000%
red >10,000%

Example 3

Neutralization Data of VRC-PG-04 and VRC-PG-05

Neutralization performed with Env-pseudoviruses using TZM-bl target cells. The values in Table 4 represent mAb concentration required to achieve 50% (Table 4A) or 80% (Table 4B) neutralization.

All monoclonal antibodies tested are IgG. CD4-Ig is chimeric 5 bivalent IgG-CD4 construct. VRC01, VRC02 and VRC03, b12, PG9 and PG16 were previously published and are shown for comparison.

Note: Breadth and potency calculations excluded Tier 1 viruses from clades B and C. Potency was calculated using viruses that have an IC50 or IC80 value within the tested range.

| | | VRC01 | VRC02 | VRC03 | VRC-PG-04 | VRC-PG-05 | b12 | CD4-Ig | PG9 | PG16 |
|---|---|---|---|---|---|---|---|---|---|---|
| Tier 1 clade B (n = 7) | HXB2 | 0.034 | 0.042 | 0.048 | 0.025 | 13 | 0.007 | 0.005 | 1.62 | >50 |
| | MN.3 | 0.022 | 0.024 | 0.027 | >50 | >50 | 0.003 | 0.006 | >50 | >50 |
| | SF162 | 0.139 | 0.112 | 0.033 | 0.024 | 6.84 | 0.070 | 0.153 | >50 | >50 |
| | ADA | 0.379 | 0.391 | 0.113 | 0.179 | 4.33 | 0.131 | 0.051 | 0.128 | 0.012 |
| | BaL.01 | 0.055 | 0.053 | 20.1 | 0.034 | 0.258 | 0.093 | 0.030 | 0.033 | 0.993 |
| | BaL.26 | 0.048 | 0.046 | 10.4 | 0.148 | 0.253 | 0.051 | 0.047 | 0.019 | 0.131 |
| | SS1196.1 | 0.170 | 0.132 | 0.048 | 0.189 | >50 | 0.840 | 0.571 | 0.074 | 0.020 |
| Tier 1 clade C | MW965.26 | 0.056 | 0.057 | >50 | 0.032 | 5.07 | 0.19 | 0.039 | 2.17 | 0.476 |
| Clade A (n = 24) | RW020.2 | 0.224 | 0.123 | >50 | 0.165 | >50 | 10.1 | 11.7 | 0.052 | 0.037 |
| | UG037.8 | 0.079 | 0.082 | 12.1 | 0.109 | >50 | >50 | 0.134 | 0.020 | 0.010 |
| | DJ263.8 | 0.080 | 0.055 | >50 | 0.803 | >50 | 0.812 | 0.088 | 0.218 | 8.21 |
| | KER2018.11 | 0.652 | 0.516 | 0.389 | 1.08 | >50 | >50 | 3.34 | 0.010 | 0.004 |
| | Q259.w6 | 0.170 | 0.147 | 0.055 | 0.028 | 7.03 | >50 | 0.708 | 1.17 | 2.58 |
| | Q769.h5 | 0.084 | 0.047 | 0.034 | 0.024 | 0.010 | >50 | 1.28 | 0.009 | 0.009 |
| | Q168.a2 | 0.115 | 0.092 | 3.38 | 0.032 | 9.92 | >50 | 11.6 | 0.045 | 0.019 |
| | Q23.17 | 0.085 | 0.071 | 0.065 | 0.084 | >50 | >50 | 12.7 | 0.005 | 0.002 |
| | Q259.17 | 0.066 | 0.047 | 0.027 | >50 | >50 | >50 | 7.38 | 0.041 | 0.030 |
| | Q461.e2 | 0.492 | 0.463 | >50 | 0.237 | 39.3 | >50 | 25.4 | 1.47 | 2.74 |
| | Q842.d12 | 0.030 | 0.025 | >50 | 0.017 | 5.12 | >50 | >50 | 0.019 | 0.009 |
| | BB201.B42 | 0.223 | 0.164 | 7.93 | 0.081 | 23.6 | 0.358 | 14.1 | 0.011 | 0.002 |
| | MB201.A1 | 0.165 | 0.089 | >50 | 0.049 | 12.9 | >50 | >50 | 0.054 | 0.021 |
| | MB201.B10 | 0.132 | 0.095 | >50 | 0.042 | 9.24 | >50 | >50 | 0.052 | 0.020 |
| | BB539.2B13 | 0.069 | 0.059 | 8.58 | 0.398 | >50 | 0.624 | 1.700 | 0.063 | 0.012 |
| | MB539.2D1 | 0.060 | 0.046 | 17 | 0.499 | >50 | 0.476 | 12.1 | 0.035 | 0.009 |
| | MB539.2B7 | 0.531 | 0.383 | >50 | 0.462 | >50 | 11.6 | 7.91 | 0.094 | 0.032 |
| | BI369.9A | 0.142 | 0.101 | >50 | 0.039 | 9.35 | 28.9 | 10.5 | 0.023 | 0.010 |
| | MI369.A5 | 0.107 | 0.086 | >50 | 0.046 | 16.4 | 4.05 | 4.35 | 0.035 | 0.012 |
| | BS208.B1 | 0.019 | 0.014 | 0.297 | 0.014 | 5.77 | 0.042 | 0.246 | 0.016 | 0.003 |
| | MS208.A1 | 0.101 | 0.074 | >50 | 0.055 | 21.6 | 0.201 | 7.94 | 0.032 | 0.008 |
| | MS208.A3 | 0.050 | 0.037 | >50 | 0.022 | 8.29 | 0.505 | 3.51 | 0.025 | 0.006 |
| | KER2008.12 | 0.379 | 0.265 | 0.403 | 0.236 | >50 | >50 | 0.649 | 0.017 | 0.008 |
| | KNH1209.18 | 0.087 | 0.095 | 45 | 0.058 | 13.6 | 0.227 | 5.95 | 0.167 | 0.283 |
| Tier 2 clade B (n = 26) | JRCSF.JB | 0.093 | 0.099 | 0.093 | 0.034 | 35 | 0.096 | 0.186 | 0.002 | 0.001 |
| | JRFL | 0.031 | 0.024 | 0.009 | 0.063 | 3.09 | 0.022 | 0.247 | >50 | >50 |
| | YU2 | 0.126 | 0.115 | 0.037 | 0.084 | 35 | 2.18 | 0.102 | 1.73 | 0.114 |
| | 89.6 | 0.511 | 0.444 | 0.187 | 0.061 | 18.8 | 0.14 | 0.242 | >50 | >50 |
| | 6101.10 | 0.111 | 0.135 | 0.094 | 0.090 | 6.77 | >50 | 2.7 | >50 | >50 |

|  |  | VRC01 | VRC02 | VRC03 | VRC-PG-04 | VRC-PG-05 | b12 | CD4-Ig | PG9 | PG16 |
|---|---|---|---|---|---|---|---|---|---|---|
|  | 7165 | 16.3 | >50 | >50 | >50 | >50 | >50 | 2.85 | >50 | 0.426 |
|  | 6535 | 0.539 | 0.733 | 0.438 | 0.687 | >50 | 0.429 | 2.49 | 0.222 | >50 |
|  | QH0692.42 | 1.5 | 1.33 | 0.954 | 1.34 | >50 | 0.97 | 0.603 | >50 | >50 |
|  | SC422661.8 | 0.076 | 0.084 | 0.036 | 0.038 | 12.8 | 0.44 | 5.19 | 0.325 | 19.1 |
|  | PVC.4 | 0.216 | 0.168 | 0.328 | 0.235 | >50 | >50 | 20.1 | 8.7 | 12.0 |
|  | TRO.11 | 0.207 | 0.208 | 0.055 | 0.131 | >50 | >50 | >50 | >50 | 0.136 |
|  | AC10.0.29 | 2.2 | 2.48 | >50 | 17.9 | 0.017 | 1.8 | 10.7 | 0.012 | 0.007 |
|  | RHPA4259.7 | 0.060 | 0.086 | 1.13 | 0.038 | 9.6 | 0.12 | 1.09 | 10 | 0.334 |
|  | THRO4156.18 | 2.25 | 3.43 | >50 | >50 | >50 | 1.21 | 0.509 | 13.2 | 0.498 |
|  | REJO4541.67 | 0.062 | 0.056 | 0.059 | 0.019 | 1.64 | 5.92 | 1.22 | 0.001 | 0.004 |
|  | TRJO4551.58 | 0.083 | 0.115 | 0.043 | 0.069 | >50 | >50 | 22.1 | 1.85 | 2.7 |
|  | WITO4160.33 | 0.148 | 0.115 | >50 | 0.080 | >50 | 8.54 | 2.17 | 0.005 | 0.002 |
|  | CAAN5342.A2 | 0.824 | 0.899 | 8.32 | 1.13 | 0.005 | >50 | >50 | 14.4 | 25.0 |
|  | BL01.DG | >50 | >50 | >50 | >50 | >50 | 1.650 | 0.100 | >50 | >50 |
|  | BR07.DG | 1.24 | 0.948 | 3.38 | 0.789 | >50 | 0.096 | 0.046 | >50 | >50 |
|  | HT593.1 | 0.334 | 0.542 | 0.235 | 0.177 | 0.389 | 0.117 | 0.323 | 0.214 | 0.056 |
|  | R2 | 0.198 | 0.242 | 0.035 | 0.291 | >50 | 1.170 | 0.016 | >50 | >50 |
|  | BG1168.01 | 0.276 | 0.458 | >50 | 0.509 | >50 | >50 | 13.4 | >50 | >50 |
|  | QH0515.01 | 0.386 | 0.470 | 0.187 | 0.115 | >50 | 0.300 | 1.83 | >50 | >50 |
|  | 5768 | 0.166 | 0.275 | 0.382 | 0.042 | >50 | 0.249 | 0.756 | 0.031 | 0.008 |
|  | 3988 | 0.220 | 0.243 | 2.46 | 0.295 | 9.70 | 0.378 | 49.4 | 0.016 | 0.005 |
| Tier 2 clade C (n = 34) | Du123.6 | 18.2 | 16.1 | >50 | >50 | >50 | 1.82 | 0.142 | 0.047 | 0.016 |
|  | Du151.2 | 3.16 | 4.83 | 34.6 | 0.059 | 0.128 | 3.79 | 1.36 | 0.012 | 0.004 |
|  | Du156.12 | 0.089 | 0.091 | >50 | 0.034 | 7.58 | 0.656 | 14.5 | 0.035 | 0.002 |
|  | Du172.17 | >50 | >50 | >50 | 0.314 | 28.5 | 0.300 | 0.26 | 0.240 | 0.023 |
|  | Du422.1 | >50 | >50 | >50 | >50 | 3.7 | 0.464 | 11.5 | 0.178 | 0.042 |
|  | ZM197M.PB7 | 0.36 | 0.408 | 2.13 | 1.14 | >50 | >50 | 28.3 | 0.287 | 0.765 |
|  | ZM214M.PL15 | 0.44 | 0.75 | 18.8 | 0.249 | >50 | 13.6 | 26.6 | >50 | >50 |
|  | ZM233M.PB6 | 1.99 | 1.03 | >50 | 7.67 | >50 | >50 | 3.36 | 0.001 | 0.001 |
|  | ZM249M.PL1 | 0.048 | 0.062 | 8.59 | 0.051 | 12.7 | 3.81 | 11.1 | 0.023 | 0.007 |
|  | ZM53M.PB12 | 1.31 | 1.4 | 10.3 | 1.51 | 0.145 | 32.6 | 8.58 | 0.092 | 0.009 |
|  | ZM109F.PB4 | 0.128 | 0.127 | >50 | 0.047 | 0.151 | >50 | 0.028 | 0.235 | 9.8 |
|  | ZM135M.PL10a | 0.346 | 0.14 | >50 | 41 | >50 | >50 | 0.296 | >50 | >50 |
|  | CAP45.2.00.G3 | 2.29 | 5.68 | >50 | >50 | >50 | 0.37 | 2.11 | 0.003 | 0.002 |
|  | CAP210.2.00.E8 | >50 | >50 | >50 | >50 | >50 | 27 | 1.48 | 0.08 | 0.021 |
|  | CAP244.2.00.D3 | 0.428 | 0.688 | 47.1 | 0.301 | >50 | >50 | 2.56 | 0.082 | 0.014 |
|  | ZA012.29 | 0.305 | 0.176 | 9.21 | 0.130 | 15.2 | >50 | 5.39 | 4.59 | 0.414 |
|  | BR025.9 | 0.115 | 0.208 | >50 | 2.77 | >50 | >50 | 0.064 | 0.018 | 0.004 |
|  | TV1.29 | >50 | >50 | >50 | >50 | >50 | >50 | 0.405 | 0.007 | 0.005 |
|  | ZM215.8 | 0.095 | 0.149 | >50 | 0.075 | 41.9 | >50 | 1.16 | 0.025 | >50 |
|  | ZM106.9 | 0.489 | 0.378 | 0.150 | 0.206 | 38.4 | >50 | 5.39 | 4.59 | 0.414 |
|  | ZM55.28a | 0.340 | 0.326 | >50 | 0.390 | >50 | >50 | >50 | 4.60 | >50 |
|  | ZM53.21 | 1.16 | 1.25 | 3.46 | 1.15 | 0.121 | 9.54 | 1.56 | 0.019 | 0.003 |
|  | ZM55.4a | 0.450 | 0.411 | >50 | 0.457 | >50 | 32.6 | 2.7 | 4.19 | 0308 |
|  | ZM106.10 | 0.566 | 0.341 | 0.154 | 0.125 | 48.4 | >50 | 41.4 | 0.097 | 0.042 |
|  | ZM109.32 | 0.091 | 0.086 | >50 | 0.055 | 0.151 | >50 | 7.69 | 0.099 | 30 |
|  | ZM135.8a | 0.374 | 0.533 | >50 | >50 | >50 | >50 | 13.7 | >50 | >50 |
|  | ZM146.7 | 0.333 | 0.396 | 1.04 | 0.403 | >50 | 18 | 4.21 | 0.181 | 0.32 |
|  | ZM176.66 | 0.055 | 0.036 | 0.033 | 0.140 | >50 | >50 | 0.212 | 0.011 | 0.002 |
|  | ZM181.6 | 1.12 | 0.574 | >50 | 11.6 | >50 | >50 | 4.9 | 0.005 | 0.001 |
|  | SO18.18 | 0.069 | 0.071 | 0.083 | 0.067 | 19.8 | 13.9 | 9.86 | 0.031 | 0.004 |
|  | 286.4 | 0.188 | 0.193 | 1.77 | 0.090 | >50 | >50 | 0.701 | 7.3 | 0.084 | 0.012 |
|  | 288.4 | 0.992 | 0.749 | 0.342 | 0.390 | >50 | >50 | 0.459 | 0.610 | 0.083 |
|  | TZA125.17 | >50 | >50 | >50 | >50 | >50 | >50 | 0.125 | 0.115 | 0.012 |
|  | TZBD.02 | 0.109 | 0.074 | 1.27 | 0.067 | 4.1 | >50 | 0.895 | 0.211 | 0.013 |
| Clade D | UG024.2 | 0.156 | 0.103 | >50 | 0.199 | >50 | >50 | 0.009 | 3.23 | >50 |
|  | 57128 | >50 | >50 | >50 | >50 | >50 | 0.169 | 0.112 | 0.136 | 0.076 |
| clade E | TH966.8 | 0.334 | 0.288 | >50 | 0.068 | 4.90 | >50 | 0.397 | 0.020 | 0.003 |
|  | TH976.17 | 0.087 | 0.112 | >50 | 0.046 | 7.48 | >50 | 0.896 | >50 | >50 |
|  | M02138 | 0.348 | 0.450 | >50 | 0.219 | 0.046 | >50 | 0.297 | 0.189 | 0.020 |
| Non-HIV | SIVmac251.30 | >50 | >50 | >50 | >50 | >50 | >50 | 0.496 | >50 | >50 |
|  | MuLV | >50 | >50 | >50 | >50 | >50 | >50 | >50 | >50 | >50 |
| Breadth | total n = 89 | 82/89 (92%) | 81/89 (91%) | 49/89 (55%) | 77/89 (87%) | 44/89 (49%) | 47/89 (53%) | 82/89 (92%) | 74/89 (83%) | 72/89 (81%) |
|  | clade A n = 24 | 24/24 (100%) | 24/24 (100%) | 13/24 (54%) | 23/24 (96%) | 14/24 (58%) | 12/24 (50%) | 21/24 (88%) | 24/24 (100%) | 24/24 (100%) |
|  | clade B n = 26 | 25/26 (96%) | 24/26 (92%) | 20/26 (77%) | 23/26 (88%) | 12/26 (46%) | 19/26 (73%) | 24/26 (92%) | 15/26 (58%) | 16/26 (62%) |
|  | clade C n = 34 | 29/34 (85%) | 29/34 (85%) | 16/34 (47%) | 27/34 (79%) | 15/34 (44%) | 15/34 (44%) | 32/34 (94%) | 31/34 (91%) | 29/34 (85%) |
| Potency* | IC50 median | 0.203 | 0.168 | 0.389 | 0.125 | 8.765 | 0.701 | 2.170 | 0.053 | 0.014 |
|  | IC50 geometric mean | 0.243 | 0.218 | 0.617 | 0.172 | 3.576 | 1.105 | 1.652 | 0.084 | 0.034 |

TABLE 4B

| | | IC$_{80}$ values (µg/ml) | | | | | | | | |
|---|---|---|---|---|---|---|---|---|---|---|
| | | VRC01 | VRC02 | VRC03 | VRC-PG-04 | VRC-PG-05 | b12 | CD4-Ig | PG9 | PG16 |
| Tier 1 clade B (n = 7) | HXB2 | 0.111 | 0.143 | 0.165 | 0.113 | >50 | 0.016 | 0.010 | >50 | >50 |
| | MN.3 | 0.082 | 0.071 | 0.073 | >50 | >50 | 0.007 | 0.018 | >50 | >50 |
| | SF162 | 0.567 | 0.367 | 0.097 | 0.127 | >50 | 0.270 | 0.539 | >50 | >50 |
| | ADA | 1.49 | 1.25 | 0.315 | 0.700 | 47.5 | 0.656 | 0.209 | 5.18 | 0.060 |
| | BaL.01 | 0.214 | 0.178 | >50 | 0.252 | 1.48 | 0.32 | 0.113 | 1.08 | >50 |
| | BaL.26 | 0.176 | 0.151 | >50 | 2.74 | 1.61 | 0.155 | 0.145 | 0.112 | >50 |
| | SS1196.1 | 0.593 | 0.411 | 0.096 | 0.649 | >50 | 4.02 | 2.86 | 0.695 | 0.179 |
| Tier 1 clade C | MW965.26 | 0.167 | 0.173 | >50 | 0.096 | 19.3 | 6.9 | 0.356 | >50 | >50 |
| Clade A (n = 24) | RW020.2 | 0.883 | 0.492 | >50 | 0.581 | >50 | 33.5 | 46.1 | 0.269 | 0.385 |
| | UG037.8 | 0.313 | 0.263 | >50 | 0.280 | >50 | >50 | 0.721 | 0.074 | 0.031 |
| | DJ263.8 | 0.553 | 0.424 | >50 | >50 | >50 | >50 | 0.557 | 2.62 | >50 |
| | KER2018.11 | 2.3 | 1.9 | 1.25 | 3.62 | >50 | >50 | 15.9 | 0.033 | 0.011 |
| | Q259.w6 | 0.543 | 0.434 | 0.178 | 0.087 | 21.5 | >50 | 2.83 | >50 | >50 |
| | Q769.h5 | 0.289 | 0.204 | 0.140 | 0.093 | 0.016 | >50 | 5.74 | 0.033 | 0.067 |
| | Q168.a2 | 0.362 | 0.310 | 27.8 | 0.112 | 29.4 | >50 | >50 | 0.173 | 0.078 |
| | Q23.17 | 0.261 | 0.220 | 0.202 | 0.269 | >50 | >50 | >50 | 0.012 | 0.005 |
| | Q259.17 | 0.233 | 0.137 | 0.085 | >50 | >50 | >50 | 19.6 | 0.166 | 0.488 |
| | Q461.e2 | 1.61 | 1.44 | >50 | 0.758 | >50 | >50 | >5.0 | 10.9 | >50 |
| | Q842.d12 | 0.096 | 0.074 | >50 | 0.046 | 14.5 | >50 | >50 | 0.070 | 0.031 |
| | BB201.B42 | 0.894 | 0.675 | >50 | 0.298 | >50 | 2.47 | >50 | 0.030 | 0.008 |
| | MB201.A1 | 0.634 | 0.310 | >50 | 0.184 | >50 | >50 | >50 | 0.193 | 0.108 |
| | MB201.B10 | 0.538 | 0.374 | >50 | 0.132 | >50 | >50 | >50 | 0.218 | 0.125 |
| | BB539.2B13 | 0.286 | 0.224 | >50 | 28.6 | >50 | 3.84 | 8.62 | 0.232 | 0.046 |
| | MB539.2D1 | 0.480 | 0.277 | >50 | 9.61 | >50 | 3.72 | 29.6 | 0.122 | 0.030 |
| | MB539.2B7 | 1.44 | 1.06 | >50 | 1.35 | >50 | >50 | 45.9 | 0.292 | 0.272 |
| | BI369.9A | 0.558 | 0.403 | >50 | 0.132 | >50 | >50 | 38.5 | 0.086 | 0.045 |
| | MI369.A5 | 0.588 | 0.464 | >50 | 0.183 | >50 | 30.9 | 22.3 | 0.191 | 0.099 |
| | BS208.B1 | 0.078 | 0.050 | 2.58 | 0.049 | 17.2 | 0.224 | 20.8 | 0.046 | 0.012 |
| | MS208.A1 | 0.462 | 0.353 | >50 | 0.221 | >50 | 1.12 | 40.9 | 0.164 | 0.095 |
| | MS208.A3 | 0.192 | 0.133 | >50 | 0.092 | 28.6 | 4.65 | >50 | 0.086 | 0.020 |
| | KER2008.12 | 1.7 | 0.994 | 1.65 | 1.03 | >50 | >50 | 3.99 | 0.068 | 0.051 |
| | KNH1209.18 | 0.296 | 0.260 | >50 | 0.201 | >50 | 1.75 | >50 | 19.1 | >50 |
| Tier 2 clade B (n = 26) | JRCSF.JB | 0.544 | 0.475 | 0.517 | 0.178 | >50 | 0.874 | 1.65 | 0.007 | 0.006 |
| | JRFL | 0.093 | 0.075 | 0.025 | 0.287 | 11.8 | 0.075 | 0.967 | >50 | >50 |
| | YU2 | 0.372 | 0.359 | 0.115 | 0.240 | >50 | 7.79 | 0.314 | 13.4 | 1.27 |
| | 89.6 | 2.32 | 1.46 | 0.589 | 0.221 | >50 | 0.56 | 0.752 | >50 | >50 |
| | 6101.10 | 0.315 | 0.384 | 0.184 | 0.247 | 29.1 | >50 | 5.33 | >50 | >50 |
| | 7165 | >50 | >50 | >50 | >50 | >50 | >50 | 33 | >50 | 12.4 |
| | 6535 | 2.74 | 3.76 | 2.4 | 4.2 | >50 | 19.1 | 16.3 | 5.04 | >50 |
| | QH0692.42 | 4.83 | 4.18 | 2.05 | 4.41 | >50 | 2.67 | 2.63 | >50 | >50 |
| | SC422661.8 | 0.265 | 0.267 | 0.105 | 0.147 | >50 | 1.69 | >50 | >50 | >50 |
| | PVO.4 | 1.19 | 1.03 | 1.68 | 1.44 | >50 | >50 | >50 | >50 | >50 |
| | TRO.11 | 0.832 | 0.876 | 0.342 | 0.744 | >50 | >50 | >50 | >50 | >50 |
| | AC10.0.29 | 6.45 | 6.95 | >50 | >50 | 0.065 | 14.2 | >50 | 0.073 | 0.023 |
| | RHPA4259.7 | 0.185 | 0.243 | 6.58 | 0.134 | 32.2 | 0.39 | 13.9 | >50 | 3.49 |
| | THRO4156.18 | 23 | 21.7 | >50 | >50 | >50 | 4.64 | 2.5 | >50 | 50 |
| | REJO4541.67 | 0.251 | 0.24 | 0.196 | 0.050 | 28.4 | >50 | 11.5 | 0.01 | 0.030 |
| | TRJO4551.58 | 0.207 | 0.284 | 0.098 | 0.183 | >50 | >50 | >50 | 17.7 | >50 |
| | WITO4160.33 | 0.412 | 0.35 | >50 | 1.19 | >50 | 41.4 | 13.2 | 0.009 | 0.006 |
| | CAAN5342.A2 | 2.77 | 3.13 | 47.6 | 5.83 | 0.012 | >50 | >50 | >50 | >50 |
| | BL01.DG | >50 | >50 | >50 | >50 | >50 | >50 | 0.626 | >50 | >50 |
| | BR07.DG | 5.15 | 4.21 | 12.8 | 5.5 | >50 | 0.898 | 0.211 | >50 | >50 |
| | HT593.1 | 1.77 | 3.86 | 0.741 | 0.790 | 1.510 | 1.73 | 4.51 | 2.09 | 2.53 |
| | R2 | 0.931 | 1.21 | 0.126 | 1.490 | >50 | 9.30 | 0.063 | >50 | >50 |
| | BG1168.01 | 1.52 | 1.97 | >50 | 2.01 | >50 | >50 | >50 | >50 | >50 |
| | QH0515.01 | 2.94 | 2.48 | 0.668 | 1.650 | >50 | 7.23 | >50 | >50 | >50 |
| | 5768 | 0.829 | 0.854 | 0.995 | 0.280 | >50 | 14.5 | >50 | 1.28 | 0.580 |
| | 3988 | 1.220 | 0.881 | 12 | 1.12 | >50 | 4.14 | >50 | 0.062 | 0.022 |
| Tier 2 clade C (n = 34) | Du123.6 | >50 | >50 | >50 | >50 | >50 | 9.16 | 0.938 | 0.247 | 0.168 |
| | Du151.2 | 46.5 | >50 | >50 | 0.370 | 2.0 | >50 | 6 | 0.054 | 0.016 |
| | Du156.12 | 0.193 | 0.204 | >50 | 0.095 | 22.8 | 2.76 | >50 | 0.109 | 0.019 |
| | Du172.17 | >50 | >50 | >50 | 1.54 | >50 | 2.62 | 1.77 | 0.952 | 0.147 |
| | Du422.1 | >50 | >50 | >50 | >50 | >50 | 1.83 | >50 | 1.95 | 0.924 |
| | ZM197M.PB7 | 1.61 | 2.04 | 9.23 | 7.03 | >50 | >50 | >50 | 2.45 | >50 |
| | ZM214M.PL15 | 2.58 | 3.19 | >50 | 2.08 | >50 | 40.4 | >50 | >50 | >50 |
| | ZM233M.PB6 | 9.33 | 4.65 | >50 | >50 | >50 | >50 | 12.4 | 0.016 | 0.004 |
| | ZM249M.PL1 | 0.232 | 0.297 | >50 | 0.146 | 40.1 | 20.3 | >50 | 0.149 | 0.031 |
| | ZM53M.PB12 | 4.02 | 4.9 | 45.6 | 7.37 | 0.496 | >50 | 32.2 | 0.33 | 0.031 |
| | ZM109F.PB4 | 0.754 | 0.619 | >50 | 0.174 | 0.602 | >50 | >50 | 0.281 | 3.73 |
| | ZM135M.PL10a | 2.71 | 1.59 | >50 | >50 | >50 | >50 | 9.76 | >50 | >50 |
| | CAP45.2.00.G3 | >50 | >50 | >50 | >50 | >50 | 4.09 | >50 | 0.014 | 0.007 |
| | CAP210.2.00.E8 | >50 | >50 | >50 | >50 | >50 | >50 | 8.3 | 0.438 | 0.159 |
| | CAP244.2.00.D3 | 2.65 | 2.08 | >50 | 0.912 | >50 | >50 | 17.5 | 0.341 | 0.048 |
| | ZA012.29 | 1.02 | 0.654 | >50 | 0.433 | >50 | >50 | 45.7 | >50 | >50 |

TABLE 4B-continued

IC$_{80}$ values (μg/ml)

|  |  | VRC01 | VRC02 | VRC03 | VRC-PG-04 | VRC-PG-05 | b12 | CD4-Ig | PG9 | PG16 |
|---|---|---|---|---|---|---|---|---|---|---|
|  | BR025.9 | 0.555 | 1.1 | >50 | >50 | >50 | >50 | 3.59 | 0.089 | 0.019 |
|  | TV1.29 | >50 | >50 | >50 | >50 | >50 | >50 | 1.04 | 0.036 | 0.147 |
|  | ZM215.8 | 0.527 | 0.724 | >50 | 0.298 | >50 | >50 | >50 | 0.437 | >50 |
|  | ZM106.9 | 1.02 | 0.654 | >50 | 0.564 | >50 | >50 | >50 | 3.56 | >50 |
|  | ZM55.28a | 1.2 | 1.03 | >50 | 1.92 | >50 | >50 | >50 | >50 | >50 |
|  | ZM53.21 | 3.59 | 4.01 | 19.9 | 4.28 | 0.327 | >50 | 7.43 | 0.071 | 0.009 |
|  | ZM55.4a | 1.5 | 1.6 | >50 | 1.53 | >50 | >50 | 17.2 | 41.2 | 14.5 |
|  | ZM106.10 | 1.37 | 0.883 | 0.452 | 0.421 | >50 | >50 | >50 | 1.29 | 2.55 |
|  | ZM109.32 | 0.422 | 0.324 | >50 | 0.190 | 0.528 | >50 | >50 | 0.727 | >50 |
|  | ZM135.8a | 2.05 | 2.43 | >50 | >50 | >50 | >50 | >50 | >50 | >50 |
|  | ZM146.7 | 1.28 | 1.39 | 4.48 | 3.27 | >50 | >50 | >50 | 1.69 | 15.4 |
|  | ZM176.66 | 0.258 | 0.154 | 0.15 | 16 | >50 | >50 | 35.4 | 0.036 | 0.006 |
|  | ZM181.6 | 6.49 | 3.78 | >50 | >50 | >50 | >50 | 31.6 | 0.013 | 0.054 |
|  | SO18.18 | 0.178 | 0.19 | 0.324 | 0.173 | >50 | >50 | >50 | 0.106 | 0.057 |
|  | 286.4 | 0.839 | 0.868 | 18.4 | 0.836 | >50 | 2.69 | 39.1 | 0.390 | 0.043 |
|  | 288.4 | 4 | 2.56 | 1.21 | 1.2 | >50 | >50 | 2.05 | >50 | 22.5 |
|  | TZA125.17 | >50 | >50 | >50 | >50 | >50 | >50 | 39.5 | 0.666 | 0.269 |
|  | TZBD.02 | 0.328 | 0.225 | 22.1 | 0.246 | 48.6 | >50 | 5.74 | 1.08 | 0.101 |
| Clade D | UG024.2 | 0.674 | 0.619 | >50 | 0.783 | >50 | >50 | 0.025 | >50 | >50 |
|  | 57128 | >50 | >50 | >50 | >50 | >50 | 1.72 | 0.855 | 0.634 | 38.3 |
| clade E | TH966.8 | 1.43 | 1.16 | >50 | 0.437 | >50 | >50 | 3.17 | 0.089 | 0.015 |
|  | TH976.17 | 0.486 | 0.593 | >50 | 0.148 | >50 | >50 | 40.8 | >50 | >50 |
|  | M02138 | 1.57 | 1.99 | >50 | 1.21 | 0.157 | >50 | 2.78 | 1.02 | 0.553 |
| Non-HIV | SIVmac251.30 | >50 | >50 | >50 | >50 | >50 | >50 | 3.95 | >50 | >50 |
|  | MuLV | >50 | >50 | >50 | >50 | >50 | >50 | >50 | >50 | >50 |
| Breadth | total n = 89 | 79/89 (89%) | 78/89 (88%) | 39/89 (44%) | 71/89 (80%) | 22/89 (25%) | 35/89 (39%) | 56/89 (63%) | 64/89 (72%) | 58/89 (65%) |
|  | clade A n = 24 | 24/24 (100%) | 24/24 (100%) | 8/24 (33%) | 22/24 (92%) | 6/24 (25%) | 9/24 (38%) | 15/24 (63%) | 23/24 (96%) | 20/24 (83%) |
|  | clade B n = 26 | 24/26 (92%) | 24/26 (92%) | 20/26 (77%) | 22/26 (85%) | 7/26 (27%) | 17/26 (65%) | 16/26 (62%) | 10/26 (38%) | 11/26 (42%) |
|  | clade C n = 34 | 27/34 (79%) | 26/34 (76%) | 11/34 (32%) | 23/34 (68%) | 8/34 (24%) | 8/34 (24%) | 20/34 (59%) | 28/34 (82%) | 24/34 (71%) |
| Potency* | IC50 median | 0.832 | 0.665 | 0.868 | 0.433 | ##### | 3.720 | 6.715 | 0.192 | 0.056 |
|  | IC50 geometric mean | 0.882 | 0.739 | 1.118 | 0.576 | 2.934 | 3.575 | 5.177 | 0.256 | 0.112 |

Red: IC50 or IC80 <1 μg/ml
Yellow: IC50 or IC80 between 1 and 1.0 μg/ml
Green: IC50 or IC80 >10 μg/ml Example 4

Potent and Broad Neutralization by a CD4 Binding Site Monoclonal Antibody from an HIV-1 Donor Infected with a Clade A1/D Recombinant Virus Several neutralizing monoclonal antibodies (NAbs) of unprecedented breadth and potency, including PG9/16 and VRC01, have been isolated from HIV-1 positive donors. In this Example, Applicants characterize PGV04 (also known as VRC-PG04), a new NAb that has potency and breadth that rivals that of PG9/16 and VRC01. PGV04 was isolated by single, memory B cell sorting using a resurfaced core (RSC3) gp120 as bait. The antibody competed with CD4, b12 and VRC01 for binding to gp120, confirming it targets the CD4 binding site (CD4bs). When screened on a large panel of viruses, PGV04 was distinguished in its neutralizing profile from CD4, b12 and VRC01. In contrast to VRC01, PGV04 did not enhance 17b or X5 binding to their epitopes in the co-receptor region on the gp120 monomer, and none of the CD4bs monoclonal antibodies (mAbs) were able to induce the co-receptor site on the functional trimer. When the ability of PGV04 to neutralize pseudovirus containing single alanine substitutions was determined, differences in residue dependence between PGV04 and other CD4bs mAbs were revealed. In particular, D279A, I420A and I423A were found to abrogate PGV04 neutralization. The residues found to be important in PGV04 neutralization had varying effects on the ability of the antibody to bind gp120 monomer containing the same substitutions. Applicants conclude broad and potent CD4bs NAbs have subtle differences in the way they recognize and access the CD4bs on the viral spike.

A study (Protocol G) that screened 1,800 HIV-1 donors infected with viruses of different clades revealed that a significant fraction of donors developed broad and potent neutralizing serum responses in agreement with studies from several laboratories (Doria-Rose et al.; Gnanakaran et al.; Doria-Rose et al. 2009; Gray et al. 2009; Sather et al. 2009; Simek et al. 2009). The top 1% of Protocol G donors that exhibited the most broad and potent serum neutralizing responses were designated "elite neutralizers". Applicants have previously mapped the serum specificities in 19 Protocol G donors who ranked within the top 5% of donors screened and found the broad serum neutralization of most donors was associated with single or a small number of specificities (Walker et al. 2010). The isolation and characterization of broad and potent neutralizing antibodies from Protocol G donors is a high priority as the epitopes targeted by these antibodies will facilitate immunogen design.

There are currently four known regions on the viral spike that are targeted by potent, broadly neutralizing antibodies (bNAbs). The first is a conserved region on the primary entry receptor of the virus, the CD4bs. This region is recognized by the bNAbs b12, HJ16, and the recently isolated bNAbs, VRC01 and VRC03 (Corti et al.; Burton et al. 1991; Wu et al. 2010). Human bNAbs 2F5, 4E10 and Z13e1 recognize the membrane proximal external region (MPER) on the gp41 protein, another conserved region located at the stalk of the viral spike. This region is thought to be important in viral fusion (Ofek et al. 2004; Cardoso et al. 2005; Nelson et al. 2007). The third epitope is composed of a cluster of high mannose glycans on the spike, recognized by 2G12, the only known HIV-1 bNAb to bind solely to glycans (Trkola et al. 1995; Sanders et al. 2002; Scanlan et al. 2002; Calarese et al. 2003). Lastly, PG9 and PG16 recognize a conserved regions of the V1/V2 and V3 loops on gp120 (Walker et al. 2009).

The CD4bs is of particular interest as a conserved region whose accessibility, at least to CD4, must be maintained. The first potent bNAb to this region, b12, was isolated from a phage display library utilizing RNA from bone marrow lymphocytes of an HIV-1 seropositive individual (presumed clade B) (Barbas et al. 1992). The bNAb neutralizes 35% of a panel of 162 cross-clade viruses with a median $IC_{50}$ of approximately 3 mg/ml in a pseudovirus assay (Walker et al. 2009). However, b12 solely interacts with gp120 through its heavy chain (Zhou et al. 2007), and the inability to isolate further anti-CD4bs bNAbs led to doubts as to whether such Abs could be elicited through immunization. A breakthrough was achieved when a bNAb, HJ16, was isolated by immortalization of memory B cells from a clade C infected donor and shown to exhibit breadth similar to that of b12 (Corti et al.). More recently and most significantly, the mAbs VRC01 and VRC03 were isolated from a clade B-infected donor (Wu et al. 2010). VRC01 neutralized 91% of a panel of 190 pseudoviruses, making it, along with PG9 and PG16, the most broad and potent HIV-1 mAbs isolated to date.

In the present Example, Applicants characterized PGV04, a novel human CD4bs mAb originating from an elite neutralizer. The antibody was isolated from single memory B cells in peripheral blood mononuclear cells (PBMC) using the RSC3 protein as bait (Wu et al 2011). The RSC3 protein has the antigenic structure of the CD4bs preserved with 30% of the surface exposed residues substituted with simian immunodeficiency virus (SIV) homologs and other residues differing from the HIV-1 sequence. Applicants confirmed that PGV04 is a CD4bs-directed mAb with broad and potent neutralization capabilities that match those of PG9 and VRC01. Moreover, the neutralizing activity of PGV04 largely recapitulated the neutralization profile of the corresponding donor serum. PGV04 was distinguished from CD4, VRC01 and b12 in its ability to neutralize JR-CSF pseudovirus containing single alanine substitutions. Furthermore, in contrast to VRC01, PGV04 did not enhance binding of the CD4-induced (CD4i) Abs, 17b or X5, to their epitopes colocalized within the co-receptor binding site on monomeric gp120, and none of the CD4bs bNAbs induced the CD4i site on functional trimers. Applicants conclude from these findings that the region of gp120 that composes the CD4bs is able to induce broad and potent mAbs with varying footprints that translate into differences in their neutralizing profiles.

Antibodies and Antigens.

The following Abs and reagents were procured by the IAVI Neutralizing Antibody Consortium: 2G12 (Polymun Scientific, Vienna, Austria), X5 and 17b (Strategic Biosolutions), soluble CD4, CD4IgG, F425 (provided by Lisa Cavacini, Beth Israel Deaconess Medical Center), JR-CSF gp120 and BaL gp120 (provided byGuillaume Stewart-Jones, MRC Human Immunology Unit, Oxford), JR-FL gp120 (Progenics, Tarrytown, N.Y.) and YU2 gp120s (provided by Robert Doms, University of Pennsylvania). The RSC3 and ΔRSC3 proteins were kindly provided by Richard Wyatt (Scripps, La Jolla, Calif.).

Donor.

The donor from whom PGV04 was isolated was selected from the IAVI sponsored study, Protocol G (Simek et al. 2009). Protocol G enrollment was defined as male or female at least 18 years of age with documented HIV infection for at least three years, clinically asymptomatic at the time of enrollment, and not currently receiving antiretroviral therapy. High-throughput analytical screening algorithms were used to select individuals for mAb generation, and this volunteer was identified as an elite neutralizer based on broad and potent serum neutralizing activity against a cross-clade pseudovirus panel.

Binding ELISAS.

RSC3 and ΔRSC3 proteins were diluted in PBS and coated at 2.0 mg/ml and JR-FL gp120 was diluted in PBS and coated at 5.0 mg/ml, 50 ml/well on Costar (3690) 96-well polystyrene ELISA plates overnight at 4° C. The plates were washed 4× with PBS containing 0.05% tween, and blocked with 3% BSA in PBS for 1 hr at 37° C. Then, 5-fold serial dilutions of the mAbs, in 1% BSA in PBS, were added at a starting concentration of 10.0 mg/ml. The plates were incubated for 1 hr at 37° C. and then washed 4× before the secondary mAb, goat anti-human IgG Fc conjugated to alkaline phosphatase (Jackson) was added at 1:1000 dilution for 1 hr at 37° C. The wells were washed and the signal was detected by adding a 5.0 mg alkaline phosphatase substrate tablet (Sigma) in 5 ml alkaline phosphatase staining buffer (pH 9.8) according to the manufacturer's instructions. The optical density at 405 nm was read on a microplate reader (Molecular Devices).

For PGV04 binding to gp120 isolated from JR-CSF pseudovirus, pseudovirus was collected 3 days post-transfection, supernatants were spun down at 300×g for 5 minutes and virus was lysed with 1.0% NP-40 at RT for 30 minutes. ELISA plates were coated overnight at 4° C. with an anti-gp120 Ab D7324 (International Enzymes, Inc.) at a concentration of 5.0 mg/ml in PBS. Plates were washed 4× and lysed virus was added at 50 ml/well and incubated for 2 hrs at 37° C. Plates were washed 4× and blocked with 3% BSA in PBS for 1 hr at RT. PGV04 and 2G12 were added in 5-fold serial dilutions starting at 10.0 mg/ml. Plates were washed 4×, and goat anti-human IgG F(ab')$_2$ conjugated to alkaline phosphatase (Pierce) was added at a 1:1000 dilution. The remainder of the experiment was conducted as above.

For competition ELISAs, plates were coated with 5.0 mg/ml of JR-FL gp120 in PBS, 50 ml/well overnight at 4° C. Plates were washed 4×, blocked with 100 ml/well of 3% BSA for 1 hr at RT. Then, 5-fold serial dilutions of competitor Abs (50 ml/well) were added starting at 10.0-80.0 mg/nil depending on the mAb. The plates were incubated for 30 minutes at RT and 50 ml of biotinylated competitor mAb were next added to the solution in the well at a 50% effective final concentration ($EC_{50}$). The $EC_{50}$ is defined as the concentration at which 50% of the mAb is bound to the protein. The plate was incubated for 1 hr at RT and washed 4×. Streptavidin-AP was added, 50 ml/well, at a 1:1000 dilution for 1 hr at RT. The plates were washed 4× and the signal was detected using alkaline phosphatase substrate tablets diluted in phosphatase staining buffer as above.

Induction of the Co-Receptor Binding Site on gp120.

ELISA plates were coated, 50 ml/well, overnight at 4° C. with 5.0 mg/ml of JR-FL or YU2 gp120 protein diluted in PBS. The plates were washed 4×, and blocked with 3% BSA for 1 hr at RT. After removing blocking solution, 10.0 mg/ml of PGV04, CD4IgG, b12, 2G12, VRC01 or VRC03 were added for 30 minutes at RT. Then 5-fold serial dilutions of biotinylated X5 or 17b (50 ml/well) were added, starting at 50.0 mg/ml and 100.0 mg/ml respectively. The plate was washed 4× and 50 ml/well of streptavidin conjugated to AP was added at 1:1000 for 1 hr. The plate was washed and developed as above.

Flow Cytometry.

Saturating amounts of PGV04, b12, 2G12, sCD4, VRC01, VRC03 or 17b were added at 20.0 mg/ml, 50 ml/well to JR-FL transfected 293T cells seeded in 96-well V-bottom plates (Cellstar), and incubated for 30 minutes at 4° C. on a plate rotator. Then a 5-fold serial dilution of biotinylated 17b starting at 20.0 mg/ml was added, 50 ml/well, to each well containing the competitor mAb for 1 hr at 4° C. on a plate rotator. The plate was washed 2× and stained with 1:200 dilution of NeutrAvidin conjugated to R-phycoerythrin (PE) (Invitrogen). Binding was analyzed using flow cytometry, and binding curves were generated by plotting the mean fluorescence intensity of antigen binding as a function of antibody concentration. A FACSCalibur (BD Biosciences) was used for flow cytometric analysis and FlowJo software for data interpretation.

Neutralization Assays.

Neutralization assays by mAbs and patient sera were performed by Monogram Biosciences as previously described using a single round of replication pseudovirus and measuring entry into U87 cells expressing either CCR5 or CXCR4 by luciferase activity (Richman et al. 2003). Briefly, pseudoviruses were produced by co-transfection of HEK293 cells with a subgenomic plasmid, pHIV-1lucΔu3, that incorporates a firefly luciferase indicator gene and a second plasmid, pCXAS that expresses HIV-1 Env libraries or clones. Following transfection, pseudovirus was harvested 3-days later and used to infect U87 cells. The cells were lysed 48 hours post-infection and luciferase activity was read on a luminometer. Generation of pseudoviruses incorporating HIV-1 JR-CSF single-alanine substitutions is fully described elsewhere (Pantophlet et al. 2003). Neutralization activity of PGV04 against HIV-1 JR-CSF pseudovirus containing single alanine substitutions in the Env protein was measured using a TZM-bl assay as described (Li et al. 2005).

Statistics.

Statistical analyses were done with Prism 5.0 for Mac (GraphPad, La Jolla, Ca).

Characterization of PGV04 as a CD4bs mAb.

PGV04 was isolated from the PBMCs of a clade A infected African donor (Wu et al 2011). Briefly, antigen-specific memory B cells were sorted employing the RSC3 gp120 to specifically screen for mAbs that target the CD4bs. The ΔRSC3 gp120, in which an amino acid at position 371 was removed in order to abolish b12 binding, was used as a negative control in the sort. As expected, PGV04 binding to the RSC3 gp120 was strong and equivalent to that of VRC01, with both mAbs showing dramatically decreased binding to ΔRSC3, consistent with their identification as CD4bs mAbs (FIG. 9A). Similar to VRC01, PGV04 also bound with high affinity to JRFL gp120 (FIG. 9B).

Applicants next performed competition ELISAs to verify that PGV04 was directed against the CD4bs. Serial dilutions of mAbs b12, CD4-IgG, VRC01, 17b, X5, 2G12, or F425 were pre-bound to ELISA plates coated with JRFL gp120 followed by the addition of a constant $EC_{50}$ concentration of biotinylated competitor mAbs listed in the legend of each graph (FIGS. 10A-D). PGV04 competed with b12, CD4-IgG and VRC01 for binding to JRFL gp120 confirming that PGV04 targets the CD4bs (FIG. 10A). PGV04 and b12 exhibited some partial competition with the CD4i mAbs, 17b and X5 (FIG. 10B). However, PGV04 did not compete with 2G12, or the V3-loop directed mAb, F425/b4e8 (FIG. 10C). Competition experiments done in reverse, in which serial dilutions of PGV04 were bound to gp120 coated plates and the $EC_{50}$ concentrations of the competitor mAbs were subsequently added, gave similar results as expected for reversible binding interactions (FIG. 10D).

Breadth and Potency of Neutralization by PGV04.

Figure 11C:
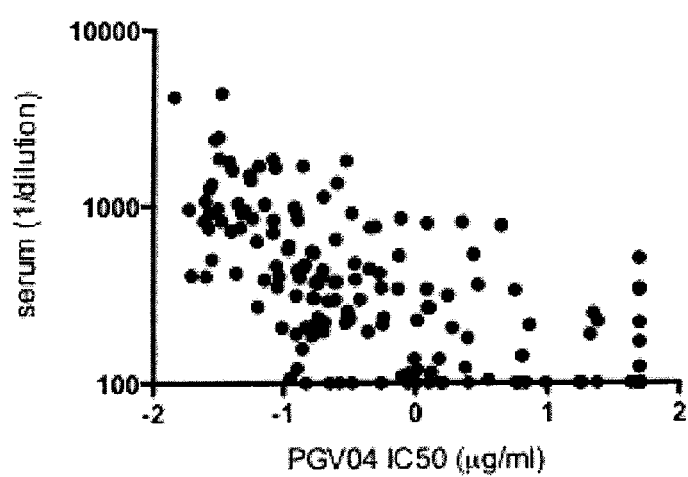

To determine the breath and potency of neutralization by PGV04, a multi-clade panel of 162 pseudoviruses was tested in a neutralization assay using U87 cells expressing either CCR5 or CXCR4 as the target cell line (FIGS. 11A-B). PGV04 neutralized 142 viruses out of the 162-virus panel with an $IC_{50}<50$ mg/ml and PG9 neutralized 122 viruses (FIG. 15A; FIG. 11A). The median $IC_{50}$ of viruses neutralized at an $IC_{50}<50$ mg/ml was comparable for PGV04 (0.20 mg/ml) and PG9 (0.27 mg/ml), indicating PGV04 and PG9 have similar potency. PGV04 neutralized 88% of the viruses in the panel while PG9 neuralized 75% of the viruses in the panel, and this difference is statistically significant (Fisher's exact test, P value=0.0063) indicating PGV04 is a broader mAb than PG9 (FIG. 11B). Of note, there were 7 viral isolates that both mAbs were unable to neutralize but these isolates are known to be neutralized by one of the other existing NAbs: PG16, b12, 4E10, 2G12 and 2F5 (Walker et al. 2009).

Figure 16:
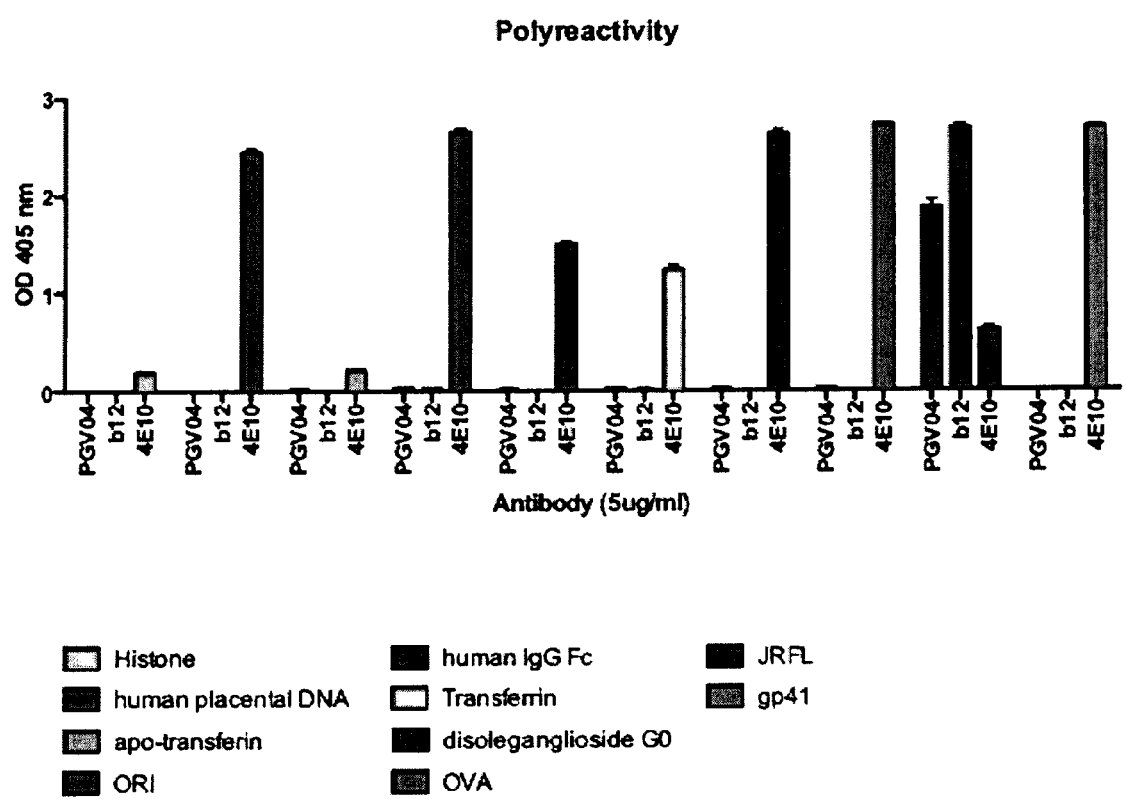
FIG. 16 depicts polyreactivity ELISA assay. PGV04 was tested for ELISA reactivity against a panel of antigens. The broad nAbs b12 and 4E10 were also included for comparison.

Next, Applicants compared the breath and potency of PGV04, PG9 and VRC01 on a second 97-pseudovirus panel that used TZM-bl cells as the target cell line (FIGS. 11A-B and FIG. 16). The results for the two virus panels were similar, although in the latter panel, the median $IC_{50}$ of the viruses that were neutralized at <50 mg/ml was lower for PG9 than for VRC01 and PGV04, and this difference was statistically significant (Mann-Whitney test, P-value <0.0001 and P-value=0.0137 respectively) indicating PG9 (0.06 mg/ml) is more potent on this panel than VRC01 (0.17 mg/ml) and PGV04 (0.12 mg/ml). PG9 neutralized 82% of viruses in the panel, PGV04 neutralized 87% and VRC01 neutralized 93% of viruses in the 97-virus panel. The difference between PG9 and VRC01 was statistically significant (Fisher's exact test, P value=0.0479), indicating VRC01 is a broader antibody than PG9.

The median $IC_{50}$ for the viruses neutralized with an $IC_{50}<50$ mg/ml was slightly lower for PGV04 (0.12 mg/ml) than VRC01 (0.17 mg/ml, Mann-Whitney test, P-value=0.0324) revealing that PGV04 is marginally more potent than VRC01 on this panel. PGV04 was slightly less broad on this panel than VRC01 (87% of 97 viruses versus 93%) but this difference was not statistically significant.

Applicants next investigated the breadth and potency of PGV04 compared to the donor serum from which PGV04 was isolated. The $IC_{50}$ of PGV04 correlated highly with the 50% neutralization titers ($NT_{50}$) of the donor serum (Mann-Whitney test, P-value <0.0001). However, there were certain instances where PGV04 did not neutralize the virus that the donor serum was able to neutralize (5 out of 162 viruses or 3% of the viruses) (FIG. 15). In these cases, Abs distinct from PGV04 appear to be responsible for serum neutralizing activity. Surprisingly, in a few cases, PGV04 neutralized a particular isolate with an $IC_{50}<1$ mg/ml while the donor serum did not neutralize this same isolate (7 out of 162 or 4% of the viruses). The reasons for this latter observation are unclear.

Induction of the Co-Receptor Binding Site on Monomeric gp120.

It has been previously shown that soluble CD4 (sCD4) enhances the binding affinity of the mAb, 17b, to gp120 (Zhang et al. 1999; Zhang et al. 2001). Interestingly, unlike b12, VRC01 has also been shown to enhance 17b binding, although not to the same extent as CD4-IgG (Wu et al. 2010). Applicants were interested in determining whether PGV04 binding to gp120 would similarly enhance the binding of CD4i mAbs. As shown in FIG. 11B, Applicants did not detect enhancement of CD4i mAb binding in the presence of PGV04. As an alternative to this experiment, Applicants added saturating amounts of PGV04, CD4-IgG, b12, 2G12, VRC01, VRC03 or no mAb to wells coated with monomeric gp120 and then added titrating amounts of either biotinylated 17b or X5 (FIGS. 12A-B). Again, PGV04 did not enhance 17b or X5 binding to either JRFL or YU2 gp120, while, CD4-IgG and VRC01 enhanced the binding of both CD4i mAbs. Interestingly, consistent with previously published data, b12 decreased 17b and X5 binding suggesting it partially competes with the CD4i mAbs (Moore and Sodroski 1996).

Induction of the Co-Receptor Binding Site on Functional Trimers.

Applicants next investigated whether PGV04 could enable 17b to bind to the functional trimer. 293T cells were co-transfected with JRFL Env DNA, and pSG3, a plasmid containing the HIV-1 backbone. Forty-eight hours post-transfection, b12, 2G12, PGV04, sCD4, VRC01, VRC03 or 17b mAbs were pre-bound at saturating concentrations to the surface-expressed Env trimers. Biotinylated 17b was then titrated onto the pre-bound complex, and binding was detected using flow cytometry. When sCD4 bound gp120 in the context of the cell surface expressed Env, it created a structural environment that allowed for 17b binding (FIG. 12C). However, no other mAb enabled detectable levels of 17b to bind to the functional trimer. As a control, serial dilutions of biotinylated 2G12 produced identical binding curves with each of the pre-bound mAbs, demonstrating that none of the CD4bs mAbs induced a significant degree of gp120 shedding from the cell-surface trimers (FIG. 12D). These results suggest there are structural constraints in the functional trimer that prevent exposure of the co-receptor site on gp120 upon binding of CD4bs mAbs that do not exist in the gp120 monomer.

PGV04 Neutralization of JR-CSF Pseudoviruses Containing Single Alanine Substitutions.

To map the PGV04 epitope, Applicants performed neutralization assays with JR-CSF pseudovirus containing single alanine substitutions in the gp120 protein. Substitutions at D279, I420 and I423 greatly compromised PGV04 neutralization, decreasing the neutralization potency to 1%, 3% and 5% that of wildtype respectively (FIG. 13A). D279A also greatly compromised CD4 and VRC01 neutralization potency yet had little effect on b12 activity. I420A and I423A likewise decreased VRC01 neutralization potency although not to the same extent as for PGV04. Moreover, these two substitutions had the opposite effect on b12 and CD4-IgG, increasing the neutralization potency of both mAbs. Interestingly, the isoleucines found at positions 420 and 423 are highly conserved among existing HIV-1 viruses in the Los Alamos database, being found at a frequency of 0.97 and 0.88 respectively. The aspartic acid found at position 279 is less conserved and found at a frequency of 0.45, with asparagine being found at this position at a frequency of 0.51.

Other alanine substitutions also abrogated PGV04 neutralization but not to the same extent as the three residues mentioned above. N276A decreased PGV04 neutralization potency to 13% that of wild-type. Notably, the N-acetyl-glucosamine from the N-linked glycan at this residue has previously been determined to be part of the VRC01 epitope through resolution of the crystal structure of VRC01 bound to gp120 (Zhou et al.). Surprisingly, removal of this glycan resulted in to a 4-fold increase in VRC01 neutralization potency while having no impact on CD4-IgG or b12 neutralization. Additionally, I307A, I309A, F317A, and Y318A decreased PGV04 neutralization to 9-36% of wildtype. These residues are found in the tip of the V3 loop and are most likely important in maintaining local structure. Interestingly, these residues have been shown to be important in maintaining the interaction between gp120 and gp41 (Xiang et al.), and alanine substitutions at these positions have been shown to result in global sensitivity to serum neutralization (Walker et al. 2010). In contrast to PGV04 and (VRC01), these substitutions increased b12 and CD4 neutralization.

PGV04 Binding to JR-CSF gp120 Containing Single Alanine Substitutions.

To further map the PGV04 epitope, Applicants evaluated the binding activity of PGV04 to a panel of gp120 proteins containing single alanine substitutions that were captured from lysed JR-CSF pseudovirus. D279A (0%), N280A (1%), D457A (4%), and R469A (3%) gp120 variants showed severely decreased PGV04 binding relative to wild-type gp120, suggesting that the residues involved are part of the PGV04 epitope (FIG. 13B). The result for D279A gp120 is consistent with the neutralization data found for the D279A variant virus in FIG. 13A. Further, three potential residues are added to the PGV04 epitope map that could not be tested in the neutralization experiments because the corresponding variant virus infectivity values were below the detection level of the assay. One of the substitutions, R469A, is found in the V5 loop and also decreases 2G12 binding. Therefore this substitution most likely disrupts gp120 structure and is not directly part of the PGV04 epitope. The D457A substitution has previously been shown to decrease binding to below 10% of wildtype for b12 and CD4 (Pantophlet et al. 2003) and D368A which decreases PGV04 binding to 12%, has previously been shown to be part of the CD4, b12 and VRC01 epitopes but not that of HJ16 (Corti et al.; Zhou et al.; Walker et al. 2010).

PGV04 Binding to Deglycosylated BaL gp120.

In Applicants' alanine scanning studies, Applicants found certain N-linked glycans affected PGV04 binding and neutralization. Therefore, Applicants determined whether the removal of glycans by Endo H, Endo F1, Endo F2, and Endo F3 from BaL gp120 protein, produced in 293T cells, would affect binding of PGV04. PGV04 and the other CD4bs mAbs, b12, VRC01, VRC03 and b6, retained similar levels of binding to both mock and deglycosylated forms of the protein suggesting CD4bs mAbs in general do not have a strong dependence on glycans for binding to gp120 (FIGS. 14A-B).

In this Example, Applicants characterized PGV04, a new broad and potent CD4bs-directed HIV-1 neutralizing mAb. PGV04 matched the breath and potency of PG9 and VRC01, two previously described potent HIV-1 bNAbs. PG9 and PGV04 neutralization was determined on two different pseudovirus panels. For a 162-pseudovirus panel in U87 cells, PGV04 and PG9 had comparable potency, with PGV04 having greater breadth. For a different 97-pseudovirus panel in TZM-bl cells, a slightly different outcome resulted. PG9 was more potent than PGV04, and PG9 had similar breadth as PGV04. PG9 neutralized the viruses in the latter panel with greater potency than the viruses in the 162-virus panel, while, PGV04 seemed to have similar neutralization potency on both panels. This may be due to the isolates chosen on both panels and/or the target cell line used, U87 versus TZM-bl cells. PGV04 had higher breadth than PG9 on both panels although this difference was statistically significant only on the 162-virus panel.

Overall, PG9/16, VRC01 and PGV04 neutralized more than 70% of circulating viruses with 10-fold greater potency than the earlier established HIV-1 bNAbs, b12, 2G12, 2F5, and 4E10. Interestingly, the virus of the PGV04 donor was subtyped as clade A1/D recombinant, which differs from the donors associated with the other CD4bs bNAbs, VRC01 (clade B), HJ16 (clade C) and b12 (presumed clade B). Therefore, it seems that elicitation of broadly neutralizing CD4bs-directed mAbs is not dependent on the clade of the infecting isolate. Of note, the PGV04 donor virus does not appear to be of any known circulating recombinant form (CRF) listed in the Los Alamos HIV databases.

Applicants' results show significant differences between CD4bs bNAbs in their mode of recognition of the CD4bs region. For example, CD4-IgG and VRC01 enhance exposure of the co-receptor binding site on monomeric gp120, while PGV04 and b12 do not. Moreover, VRC01, b12 and PGV04, in contrast to CD4, did not induce the co-receptor site on functional trimers. These observations suggest that differences exist between the presentation of the CD4bs in recombinant gp120 versus gp120 in the context of the functional trimer. These observations also highlight differences in VRC01 and PGV04 recognition of the CD4bs, as it is exposed on monomeric gp120.

In Applicants' alanine scanning studies, several alanine substitutions affected the CD4bs mAbs differently, again illustrating that PGV04, VRC01, b12 and CD4-IgG recognize the CD4bs in somewhat different ways. For example, D279A, I420A and I423A substitutions greatly decreased neutralization of PGV04, but varied in their effects on VRC01, CD4-IgG and b12. The D279A substitution decreased neutralization by VRC01 and CD4-IgG but had no great effect on b12. The I420A and I423A substitutions decreased VRC01 neutralization but increased both CD4-IgG and b12 neutralization. In addition, certain substitutions in the V3 loop decreased neutralization by PGV04 and VRC01 but increased neutralization by CD4 and b12. Importantly, the highly conserved nature of the residues important for PGV04 recognition likely explains how PGV04 is able to achieve broad neutralization. Indeed, it will be interesting to determine which residues are important for natural escape to PGV04.

The results of this Example have implications for vaccine design. Considering that a collection of broad and potent CD4bs-directed neutralizing antibodies have been isolated from naturally infected donors, and CD4bs neutralizing activity has been detected in several broadly neutralizing sera (Li et al. 2007; Binley et al. 2008; Gray et al. 2009; Li et al. 2009; Sather et al. 2009), it appears that this region may be a particularly promising vaccine target. Also Applicants' data show that different CD4bs bNAbs can target slightly different epitopes, which may have implications for the design of immunogens that focus the immune response on the CD4bs.

Barbas, C. F., 3rd, E. Bjorling, F. Chiodi, N. Dunlop, D. Cababa, T. M. Jones, S. L. Zebedee, M. A. Persson, P. L. Nara, E. Norrby and et al. (1992). "Recombinant human Fab fragments neutralize human type 1 immunodeficiency virus in vitro." Proc Natl Acad Sci USA 89(19): 9339-43.

Binley, J. M., E. A. Lybarger, E. T. Crooks, M. S. Seaman, E. Gray, K. L. Davis, J. M. Decker, D. Wycuff, L. Harris, N. Hawkins, B. Wood, C. Nathe, D. Richman, G. D. Tomaras, F. Bibollet-Ruche, J. E. Robinson, L. Morris, G. M. Shaw, D. C. Montefiori and J. R. Mascola (2008). "Profiling the specificity of neutralizing antibodies in a large panel of plasmas from patients chronically infected with human immunodeficiency virus type 1 subtypes B and C." J Virol 82(23): 11651-68.

Burton, D. R., C. F. Barbas, 3rd, M. A. Persson, S. Koenig, R. M. Chanock and R A. Lerner (1991). "A large array of human monoclonal antibodies to type 1 human immunodeficiency virus from combinatorial libraries of asymptomatic seropositive individuals." Proc Natl Acad Sci USA 88(22): 10134-7.

Calarese, D. A., C. N. Scanlan, M. B. Zwick, S. Deechongkit, Y. Mimura, R. Kunert, P. Zhu, M. R. Wormald, R. L. Stanfield, K. H. Roux, J. W. Kelly, P. M. Rudd, R. A. Dwek, H. Katinger, D. R. Burton and I. A. Wilson (2003). "Antibody domain exchange is an immunological solution to carbohydrate cluster recognition." Science 300(5628): 2065-71.

Cardoso, R. M., M. B. Zwick, R. L. Stanfield, R. Kunert, J. M. Binley, H. Katinger, D. R. Burton and I. A. Wilson (2005). "Broadly neutralizing anti-HIV antibody 4E10 recognizes a helical conformation of a highly conserved fusion-associated motif in gp41." Immunity 22(2): 163-73.

Corti, D., J. P. Langedijk, A. Hinz, M. S. Seaman, F. Vanzetta, B. M. Fernandez-Rodriguez, C. Silacci, D. Pinna, D. Jarrossay, S. Balla-Jhagjhoorsingh, B. Willems, M. J. Zekveld, H. Dreja, E. O'Sullivan, C. Pade, C. Orkin, S. A. Jeffs, D. C. Montefiori, D. Davis, W. Weissenhorn, A. McKnight, J. L. Heeney, F. Sallusto, Q. J. Sattentau, R. A. Weiss and A. Lanzavecchia "Analysis of memory B cell responses and isolation of novel monoclonal antibodies with neutralizing breadth from HIV-1-infected individuals." PLoS One 5(1): e8805.

Doria-Rose, N. A., R. M. Klein, M. G. Daniels, S. O'Dell, M. Nason, A. Lapedes, T. Bhattacharya, S. A. Migueles, R. T. Wyatt, B. T. Korber, J. R. Mascola and M. Connors "Breadth of human immunodeficiency virus-specific neutralizing activity in sera: clustering analysis and association with clinical variables." J Virol 84(3): 1631-6.

Doria-Rose, N. A., R M. Klein, M. M. Manion, S. O'Dell, A. Phogat, B. Chakrabarti, C. W. Hallahan, S. A. Migueles, J. Wrammert, R. Ahmed, M. Nason, R. T. Wyatt, J. R. Mascola and M. Connors (2009). "Frequency and phenotype of human immunodeficiency virus envelope-specific B cells from patients with broadly cross-neutralizing antibodies." J Virol 83(1): 188-99.

Gnanakaran, S., M. G. Daniels, T. Bhattacharya, A. S. Lapedes, A. Sethi, M. Li, H. Tang, K. Greene, H. Gao, B. F. Haynes, M. S. Cohen, G. M. Shaw, M. S. Seaman, A. Kumar, F. Gao, D. C. Montefiori and B. Korber "Genetic signatures in the envelope glycoproteins of HIV-1 that associate with broadly neutralizing antibodies." PLoS Comput Biol 6(10): e1000955.

Gray, E. S., N. Taylor, D. Wycuff, P. L. Moore, G. D. Tomaras, C. K. Wibmer, A. Puren, A. DeCamp, P. B. Gilbert, B. Wood, D. C. Montefiori, J. M. Binley, G. M. Shaw, B. F. Haynes, J. R. Mascola and L. Morris (2009). "Antibody specificities associated with neutralization breadth in plasma from human immunodeficiency virus type 1 subtype C-infected blood donors." J Virol 83(17): 8925-37.

Li, M., F. Gao, J. R. Mascola, L. Stamatatos, V. R. Polonis, M. Koutsoukos, G. Voss, P. Goepfert, P. Gilbert, K. M. Greene, M. Bilska, D. L. Kothe, J. F. Salazar-Gonzalez, X. Wei, J. M. Decker, B. H. Hahn and D. C. Montefiori (2005). "Human immunodeficiency virus type 1 env clones from acute and early subtype B infections for standardized assessments of vaccine-elicited neutralizing antibodies." J Virol 79(16): 10108-25.

Li, Y., S. A. Migueles, B. Welcher, K. Svehla, A. Phogat, M. K. Louder, X. Wu, G. M. Shaw, M. Connors, R T. Wyatt and J. R. Mascola (2007). "Broad HIV-1 neutralization mediated by CD4-binding site antibodies." Nat Med 13(9): 1032-4.

Li, Y., K. Svehla, M. K. Louder, D. Wycuff, S. Phogat, M. Tang, S. A. Migueles, X. Wu, A. Phogat, G. M. Shaw, M. Connors, J. Hoxie, J. R. Mascola and R. Wyatt (2009). "Analysis of neutralization specificities in polyclonal sera derived from human immunodeficiency virus type 1-infected individuals." J Virol 83(2): 1045-59.

Moore, J. P. and J. Sodroski (1996). "Antibody cross-competition analysis of the human immunodeficiency virus type 1 gp120 exterior envelope glycoprotein." J Virol 70(3): 1863-72.

Nelson, J. D., F. M. Brunel, R. Jensen, E. T. Crooks, R. M. Cardoso, M Wang, A. Hessell, I. A. Wilson, J. M. Binley, P. E. Dawson, D. R. Burton and M. B. Zwick (2007). "An affinity-enhanced neutralizing antibody against the membrane-proximal external region of human immunodeficiency virus type 1 gp41 recognizes an epitope between those of 2F5 and 4E10." J Virol 81(8): 4033-43.

Ofek, G., M. Tang, A. Sambor, H. Katinger, J. R Mascola, R. Wyatt and P. D. Kwong (2004). "Structure and mechanistic analysis of the anti-human immunodeficiency virus type 1 antibody 2F5 in complex with its gp41 epitope." J Virol 78(19): 10724-37.

Pantophlet, R., E. Ollmann Saphire, P. Poignard, P. W. Parren, I. A. Wilson and D. R. Burton (2003). "Fine mapping of the interaction of neutralizing and nonneutralizing monoclonal antibodies with the CD4 binding site of human immunodeficiency virus type 1 gp120." J Virol 77(1): 642-58.

Richman, D. D., T. Wrin, S. J. Little and C. J. Petropoulos (2003). "Rapid evolution of the neutralizing antibody response to HIV type 1 infection." Proc Natl Acad Sci USA 100(7): 4144-9.

Sanders, R. W., M. Venturi, L. Schiffner, R. Kalyanaraman, H. Katinger, K. O. Lloyd, P. D. Kwong and J. P. Moore (2002). "The mannose-dependent epitope for neutralizing antibody 2G12 on human immunodeficiency virus type 1 glycoprotein gp120." J Virol 76(14): 7293-305.

Sather, D. N., J. Armann, L. K. Ching, A. Mavrantoni, G. Sellhorn, Z. Caldwell, X. Yu, B. Wood, S. Self, S. Kalams and L. Stamatatos (2009). "Factors associated with the development of cross-reactive neutralizing antibodies during human immunodeficiency virus type 1 infection." J Virol 83(2): 757-69.

Scanlan, C. N., R. Pantophlet, M. R. Wormald, E. Ollmann Saphire, R. Stanfield, I. A. Wilson, H. Katinger, R. A. Dwek, P. M. Rudd and D. R. Burton (2002). "The broadly neutralizing anti-human immunodeficiency virus type 1 antibody 2G12 recognizes a cluster of alpha1→2 mannose residues on the outer face of gp120." J Virol 76(14): 7306-21.

Simek, M. D., W. Rida, F. H. Priddy, P. Pung, E. Carrow, D. S. Laufer, J. K. Lehrman, M. Boaz, T. Tarragona-Fiol, G. Miiro, J. Birungi, A. Pozniak, D. A. McPhee, O. Manigart, E. Karita, A. Inwoley, W. Jaoko, J. Dehovitz, L. G. Bekker, P. Pitisuttithum, R. Paris, L. M. Walker, P. Poignard, T. Wrin, P. E. Fast, D. R. Burton and W. C. Koff (2009). "Human immunodeficiency virus type 1 elite neutralizers: individuals with broad and potent neutralizing activity identified by using a high-throughput neutralization assay together with an analytical selection algorithm." J Virol 83(14): 7337-48.

Trkola, A., A. B. Pomales, H. Yuan, B. Korber, P. J. Maddon, G. P. Allaway, H. Katinger, C. F. Barbas, 3rd, D. R. Burton, D. D. Ho and et al. (1995). "Cross-clade neutralization of primary isolates of human immunodeficiency virus type 1 by human monoclonal antibodies and tetrameric CD4-IgG." J Virol 69(11): 6609-17.

Walker, L. M., S. K. Phogat, P. Y. Chan-Hui, D. Wagner, P. Phung, J. L. Goss, T. Wrin, M. D. Simek, S. Fling, J. L. Mitcham, J. K. Lehrman, F. H. Priddy, O. A. Olsen, S. M. Frey, P. W. Hammond, S. Kaminsky, T. Zamb, M. Moyle, W. C. Koff, P. Poignard and D. R Burton (2009). "Broad and potent neutralizing antibodies from an African donor reveal a new HIV-1 vaccine target." Science 326(5950): 285-9.

Walker, L. M., M. D. Simek, F. Priddy, J. S. Gach, D. Wagner, M. B. Zwick, S. K. Phogat, P. Poignard and D. R. Burton (2010). "A limited number of antibody specificities mediate broad and potent serum neutralization in selected HIV-1 infected individuals." PLoS Pathog 6(8).

Wu, X., Z. Y. Yang, Y. Li, C. M. Hogerkorp, W. R Schief, M. S. Seaman, T. Zhou, S. D. Schmidt, L. Wu, L. Xu, N. S. Longo, K. McKee, S. O'Dell, M. K. Louder, D. L. Wycuff, Y. Feng, M. Nason, N. Doria-Rose, M. Connors, P. D. Kwong, M. Roederer, R. T. Wyatt, G. J. Nabel and J. R. Mascola (2010). "Rational design of envelope identifies broadly neutralizing human monoclonal antibodies to HIV-1." Science 329(5993): 856-61.

Xiang, S. H., A. Finzi, B. Pacheco, K. Alexander, W. Yuan, C. Rizzuto, C. C. Huang, P. D. Kwong and J. Sodroski "A V3 loop-dependent gp120 element disrupted by CD4 binding stabilizes the human immunodeficiency virus envelope glycoprotein trimer." J Virol 84(7): 3147-61.

Zhang, W., G. Canziani, C. Plugariu, R. Wyatt, J. Sodroski, R. Sweet, P. Kwong, W. Hendrickson and I. Chaiken (1999). "Conformational changes of gp120 in epitopes near the CCR5 binding site are induced by CD4 and a CD4 miniprotein mimetic." Biochemistry 38(29): 9405-16.

Zhang, W A. P. Godillot, R. Wyatt, J. Sodroski and I. Chaiken (2001). "Antibody 17b binding at the coreceptor site weakens the kinetics of the interaction of envelope glycoprotein gp120 with CD4." Biochemistry 40(6): 1662-70.

Zhou, T., I. Georgiev, X. Wu, Z. Y. Yang, K. Dai, A. Finzi, Y. D. Kwon, J. F. Scheid, W. Shi, L. Xu, Y. Yang, J. Zhu, M. C. Nussenzweig, J. Sodroski, L. Shapiro, G. J. Nabel, J. R Mascola and P. D. Kwong "Structural basis for broad and potent neutralization of HIV-1 by antibody VRC01." Science 329 (5993): 811-7.

Zhou, T., L. Xu, B. Dey, A. J. Hessell, D. Van Ryk, S. H. Xiang, X. Yang, M. Y. Zhang, M. B. Zwick, J. Arthos, D. R. Burton, D. S. Dimitrov, J. Sodroski, R Wyatt, G. J. Nabel and P. D. Kwong (2007). "Structural definition of a conserved neutralization epitope on HIV-1 gp120." Nature 445(7129): 732-7.

Example 5

Focused Evolution of HIV-1 Neutralizing Antibodies Revealed by Crystal Structures and Deep Sequencing Antibody VRC01 is a human immunoglobulin that neutralizes ~90% of HIV-1 isolates. To understand how such broadly neutralizing antibodies develop, Applicants used X-ray crystallography and 454 pyrosequencing to characterize additional VRC01-like antibodies from HIV-1-infected individuals. Crystal structures revealed a convergent mode of binding for diverse antibodies to the same CD4-binding-site epitope. A functional genomics analysis of expressed heavy and light chains revealed common pathways of antibody-heavy chain maturation, confined to the IGHV1-2*02 lineage, involving dozens of somatic changes, and capable of pairing with different light chains. Broadly neutralizing HIV-1 immunity associated with VRC01-like antibodies thus involves the evolution of antibodies to a highly affinity-matured state required to recognize an invariant viral structure, with lineages defined from thousands of sequences providing genetic roadmaps of their development.

HIV-1 exhibits extraordinary genetic diversity and has evolved multiple mechanisms of resistance to evade the humoral immune response (1-3). Despite these obstacles, 10-25% of HIV-1-infected individuals develop cross-reactive neutralizing antibodies after several years of infection (4-9). Elicitation of such antibodies could form the basis for an effective HIV-1 vaccine, and intense effort has focused on identifying responsible antibodies and delineating their characteristics. A variety of monoclonal antibodies (mAbs) have been isolated that recognize a range of epitopes on the functional HIV-1 viral spike, which is composed of three highly glycosylated gp120 exterior envelope glycoproteins and three transmembrane gp41 molecules. Some broadly neutralizing antibodies are directed against the membrane-proximal external region of gp41 (10-11), but the majority recognize gp120. These include the quaternary structure-preferring antibodies PG9, PG16, and CH01-04 (12-13), the glycan-reactive antibodies 2G12 and PGT121-144 (14-15), and antibodies b12, HJ16, and VRC01-03, which are directed against the region of HIV-1 gp120 involved in initial contact with the CD4 receptor (16-19).

One unusual characteristic of all these gp120-reactive broadly neutralizing antibodies is a high level of somatic mutation. Antibodies typically accumulate 5-15% changes in variable domain-amino acid sequence during the affinity maturation process (20), but for these gp120 reactive neutralizing antibodies, the degree of heavy chain-somatic mutation is markedly increased, ranging from 19% for the quaternary structure-preferring antibodies (12), to 31% for antibody 2G12 (21-22), and to 40-46% for the CD4-binding-site antibodies, HJ16 (17), VRC01, VRC02, and VRC03 (18).

In the case of VRC01, the mature antibody accumulates roughly 70 total changes in amino acid sequence during the maturation process. The mature VRC01 can neutralize ~90% of HIV-1 isolates at a geometric mean $IC_{50}$ of 0.3 μg/ml (18), and structural studies show that it achieves this neutralization by precisely recognizing the initial site of CD4 attachment on HIV-1 gp120 (19). By contrast, the predicted unmutated germline ancestor of VRC01 has weak affinity for typical strains of gp120 (~mM) (19). Moreover, with only three VRC01-like antibodies identified in a single individual (donor 45), it has been unclear whether the VRC01-mode of recognition, genetic origin, and pathway of affinity maturation represent general features of the B-cell response to the CD4-binding site of HIV-1 gp120. Here Applicants explore how broadly neutralizing HIV-1 immunity associated with VRC01-like antibodies develops, with an analysis of dozens of neutralizers from additional donors to answer questions of generality and to trace pathways of affinity maturation with thousands of VRC01-like antibody sequences.

Isolation of Neutralizing Antibodies from Donors 74 and 0219 with a CD4-Binding-Site Probe.

Applicants previously used structure-guided resurfacing to alter the antigenic surfaces on HIV-1 gp120 while preserving the initial site of attachment to the CD4 receptor (18). With the resurfaced stabilized core 3 probe (RSC3), over 30% of the surface residues of core gp120 were altered and the conformation stabilized by the addition of interdomain-disulfide bonds and cavity-filling point mutations (18). Applicants used RSC3 and a mutant version containing a single amino acid deletion in the CD4-binding loop (ΔRSC3) to interrogate a panel of 12 broadly neutralizing sera derived from the IAVI protocol G cohort of HIV-1 infected individuals (6, 23) (FIG. 17A). A substantial fraction of neutralization of three sera was specifically blocked by RSC3 compared with A RSC3, indicating the presence of CD4-binding-site-directed neutralizing antibodies. RSC3-neutralization competition assays also confirmed the presence of CD4-binding-site antibodies in the previously characterized sera 0219, identified in the CHAVI 001 cohort (8) (FIG. 17A). Peripheral blood mononuclear cells (PBMCs) from protocol G donor 74 (infected with AD recombinant) and from CHAVI donor 0219 (infected with clade A) were used for antigen-specific B-cell sorting and antibody isolation. For donor 74 and 0219, respectively, a total of 0.13% and 0.15% of $IgG^+$ B cells were identified (FIG. 17B). The heavy and light chain immunoglobulin genes from individual B-cells were amplified and cloned into IgG1 expression vectors that reconstituted the full IgG (18, 24). From donor 74, two somatically related antibodies named VRC-PG04 and VRC-PG04b demonstrated strong binding to several versions of gp120 and to RSC3 but >100-fold less binding to ΔRSC3. From donor 0219, five somatically related antibodies named VRC-CH30, 31, 32, 33 and 34 displayed a similar pattern of RSC3; ΔRSC3 reactivity. Sequence analysis of these two sets of antibody clones (FIG. 17C) revealed that they originated from the same inferred immunoglobulin heavy chain variable (IGHV) precursor gene allele IGHV1-2*02. Despite this similarity in heavy chain V-gene origin, the two clone sets originated from different heavy chain J segment genes and contained different light chains. The light chains of the VRC-PG04 and 04b somatic variants originated from an IGκV3 allele whereas the VRC-CH30-34 somatic variants derived from an IGκV1 allele. Of note, all seven antibodies were highly affinity matured: VRC-PG04 and 04b displayed a $V_H$ gene mutation frequency of 30% relative to the germline IGHV1-2*02 allele, a level of affinity maturation similar to that previously observed with VRC01-03; the VRC-CH30-34 antibodies were also highly affinity matured, with $V_H$ mutation frequency of 23-25%.

Figure 17D:
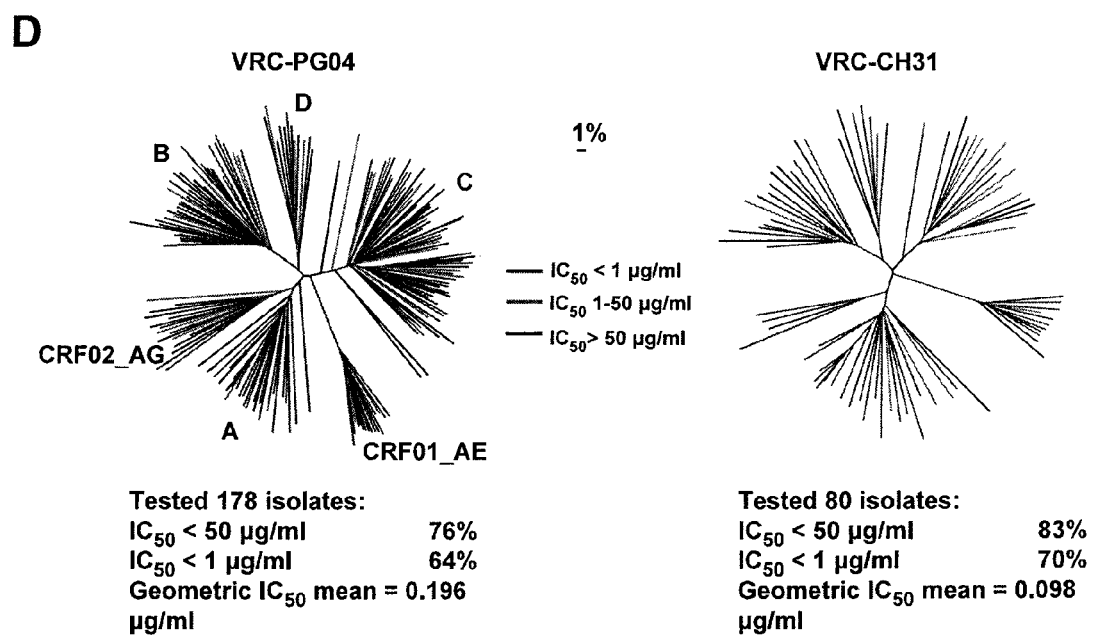

To define the reactivities of these new antibodies on gp120, Applicants performed competition ELISAs with a panel of well-characterized mAbs. Binding by each of the new antibodies was competed by VRC01-03, by other CD4-binding-site antibodies and by CD4-Ig, but not by antibodies known to bind gp120 at other sites. Despite similarities in gp120 reactivity and $V_H$-genomic origin, sequence similarities of heavy and light chain gene regions did not readily account for their mode of gp120 recognition. Finally, assessment of VRC-PG04 and VRC-CH31 neutralization on a panel of Env-pseudoviruses revealed their ability to potently neutralize a majority of diverse HIV-1 isolates (FIG. 17D).

Structural Definition of Gp120 Recognition by RSC3-Identified Antibodies from Different Donors: a Remarkable Convergence.

To define the mode of gp120 recognition employed by donor 74-derived VRC-PG04, Applicants crystallized its antigen-binding fragment (Fab) in complex with a gp120 core from the clade A/E recombinant 93TH057 that was previously crystallized with VRC01 (19). Diffraction data to 2.1 Å resolution were collected from orthorhombic crystals, and the structure solved by molecular replacement and refined to a crystallographic R-value of 19.0% (FIG. 18A). The structure of VRC-PG04 in complex with HIV-1 gp120 showed striking similarity with the previously determined complex with VRC01, despite different donor origins and only 50% amino acid identity in the heavy chain-variable region (FIG. 18). When gp120s were superimposed, the resultant heavy chain positions of VRC-PG04 and VRC01 differed by a root-mean-square deviation (rmsd) of 2.1 Å in Cα-atoms, with even more precise alignment of the heavy chain-second complementarity determining (CDR H2) region (1.5 Å rmsd). Critical interactions such as the $Asp368_{gp120}$ salt bridge to $Arg71_{VRC01}$ were maintained in VRC-PG04 (FIG. 18B).

Applicants also crystallized the gp120-Fab complex of the donor 45-derived VRC03 mAb, the isolation and initial characterization of which were previously described (18). VRC03 and VRC-PG04 share only 51% heavy chain-variable protein sequence identity, and the heavy chain of VRC03 contains an unusual insertion in the framework 3 region (18). Diffraction data to 1.9 Å resolution were collected from orthorhombic crystals, and the structure solved by molecular replacement and refined to a crystallographic R-value of 18.7% (FIG. 18). VRC03 also showed recognition of gp120 that was strikingly similar to that of VRC-PG04 and VRC01, with similar interface residues and pairwise rmsds in Cα-atoms of 2.4 and 1.9 Å, respectively. In particular, gp120-interactive surfaces of CDR H2 and CDR L3 showed similar recognition (pairwise Cα-rmds of these regions of the antibodies ranged from 0.5-1.4 Å after superposition of gp120).

In general, the repertoire of possible immunoglobulin products is very large and highly similar modes of antibody recognition are expected to occur infrequently (25). To assess how atypical the VRC01-like antibody convergence was, Applicants analyzed other families of HIV-1 specific antibodies that share common IGHV-gene origins (26-29), including the CD4-induced antibodies, 17b, 412d and X5, all of which derive from a common IGHV1-69 allele. Analysis of the recognition of gp120 by these antibodies indicated substantial variation, with angular difference in heavy chain orientation between 17b, 412d and X5 of over 90°, or roughly 10-fold greater than among the VRC01-like antibodies. Also, the RSC3 probe may select for a particular mode of recognition, so Applicants analyzed other CD4-binding-site antibodies that bind strongly to the RSC3 probe, including antibodies b12 and b13 (16, 30); these other RSC3-reactive antibodies also showed dramatic differences in heavy chain orientation relative to the VRC01-like antibodies.

The remarkable convergence in recognition observed with VRC01, VRC03, and VRC-PG04 suggested a common mode of HIV-1 gp120 recognition, conserved between donors infected with a clade B (donor 45) or a clade A/D (donor 74) strain of HIV-1. The precision required for this mode of recognition likely arises as a consequence of the multiple mechanisms of immune evasion that protect the site of CD4 attachment on HIV-1 gp120 (30). Applicants analyzed paratope surface properties and found that the average energy of antibody hydrophobic interactions ($\Delta^i G$) correlated with the convergence in antibody recognition (P=0.0427) (FIG. 19A) (31). Thus although precise H-bonding is required for this mode of recognition (FIG. 18C), the convergence in structure appears to optimize regions with hydrophobic interactions. Another important feature of this mode of recognition is its ability to focus precisely on the initial site of CD4 receptor attachment (19, 32). Indeed, the breadth of HIV-1 neutralization among CD4-binding-site ligands correlated with targeting onto this site (P=0.0405) (FIG. 19B).

This convergence in epitope recognition is accompanied by a divergence in antibody sequence identity (FIGS. 17C AND 19C). All ten antibodies isolated by RSC3 binding utilize the IGHV1-2*02 germline and accrue 70-90 nucleotide changes. Despite this similarity in the epitope recognized by these mature antibodies, only two residues from the germline IGHV1-2*02 allele mature to the same amino acids (FIG. 17C). Both of these changes occur at a hydrophobic contact in the critical CDR H2 region (56: Gly→Ala and 57: Thr→Val). The light chains for donors 45 and 74 antibodies arise from either IGVκ3-11*01 or IGVκ3-20*01, whereas the light chains of donor 0219 antibodies are derived from IGVκ1-33*01. For these light chains, no maturational changes are identical. Despite this diversity in maturation, comparison of the VRC01, VRC03, and VRC-PG04 paratopes shows that many of these changes are of conserved chemical character (FIG. 19C); a hydrophobic patch in the CDR L3, for example, is preserved. These observations suggest that divergent amino acid changes among VRC01-like antibodies nevertheless afford convergent recognition when guided by affinity maturation.

Functional complementation of heavy and light chains among VRC01-like antibodies.

Although the identification and sorting of antigen-specific B cells with resurfaced probes has resulted in the isolation of several broadly neutralizing antibodies, genomic analysis of B-cell cDNA libraries provides thousands of sequences for analysis. These sequences specify the functional 'antibodyome', the repertoire of expressed antibody heavy and light chain sequences in each individual. High-throughput sequencing methods provide heavy chain and light chain sequences, but do not retain information about their pairings. For VRC01-like antibodies, the structural convergence revealed by the crystallographic analysis indicated a potential solution: different heavy and light chains might achieve functional complementation within this antibody family.

Figure 20A:
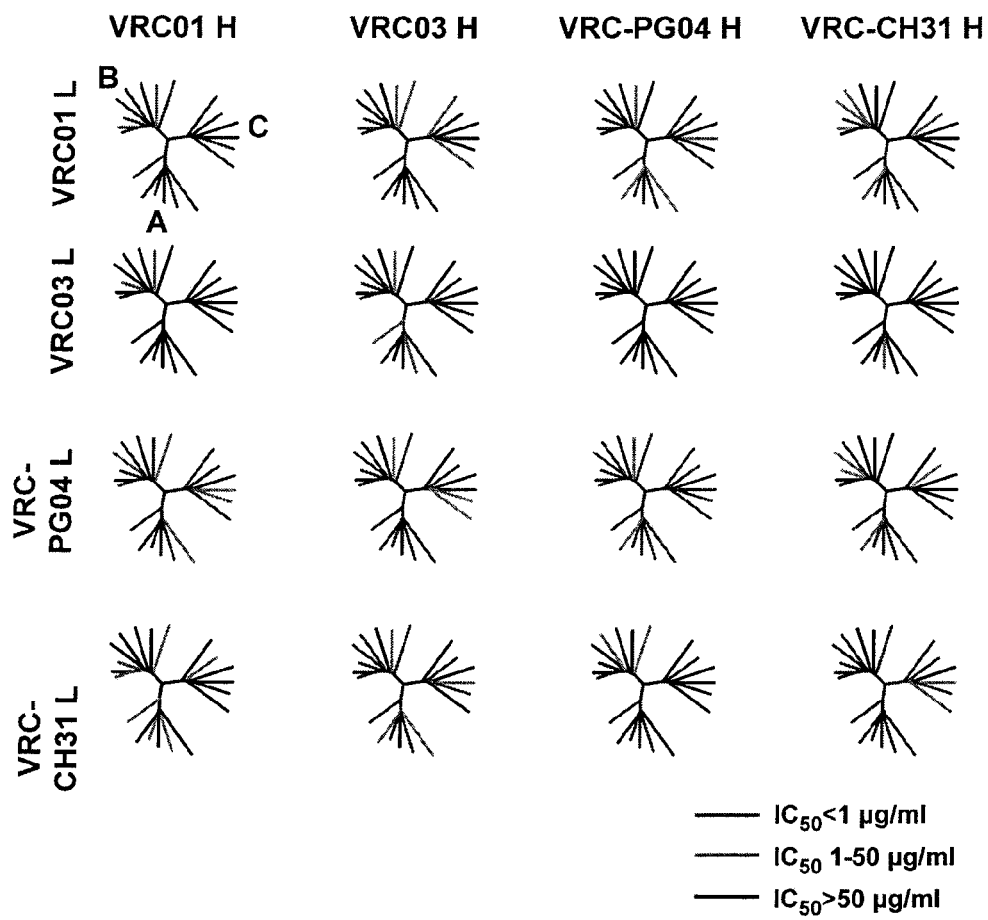

Heavy and light chain chimeras of VRC01, VRC03, VRC-PG04 and VRC-CH31 were produced by transient transfection and tested for HIV-1 neutralization. VRC01 (donor 45) and VRC-PG04 (donor 74) light chains were functionally compatible with VRC01, VRC03 and VRC-PG04 heavy chains, though the VRC03 light chain was compatible only with the VRC03 heavy chain (FIG. 20A). Similarly, despite ~50% differences in sequence identity, the VRC-CH31 (donor 0219) heavy and light chains were able to functionally complement most of the other antibodies (FIG. 20A).

Identification of VRC01-Like Antibodies by Deep Sequencing of Donors 45 and 74.

Figure 20B:
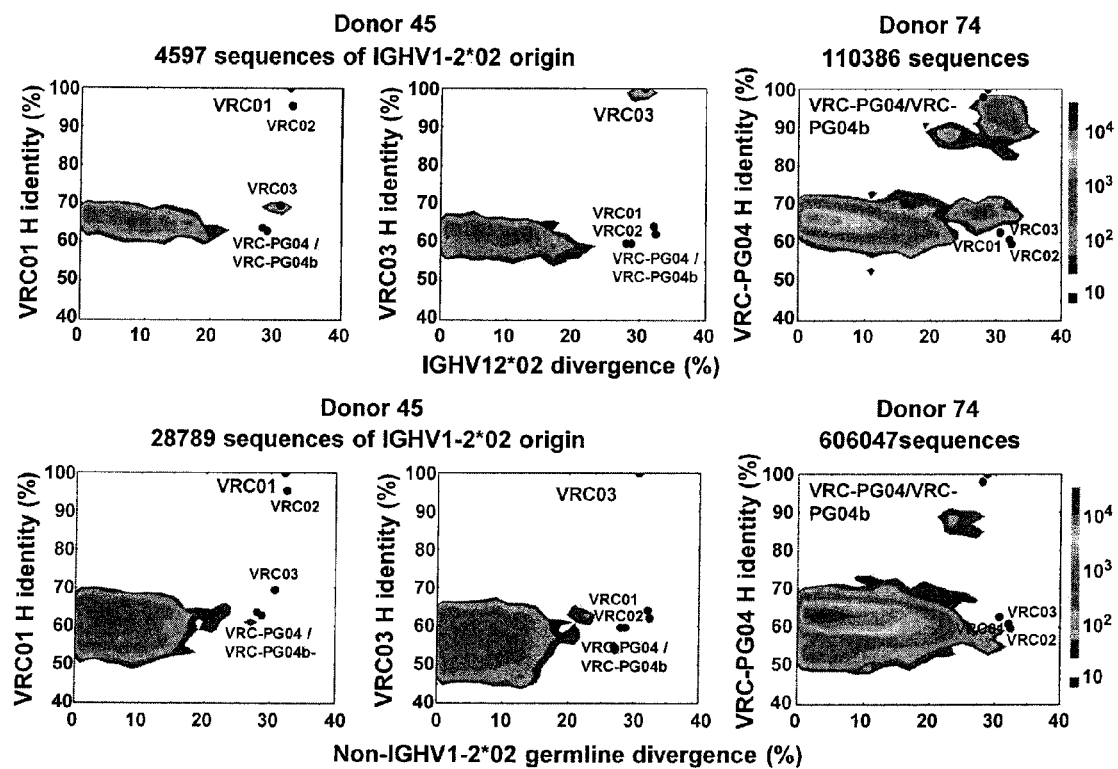

To study the antibody repertoire in these individuals, Applicants performed deep sequencing of cDNA from donor 45 PBMC (33). Because the variable regions of heavy and light chains are roughly 400 nucleotides in length, 454 pyrosequencing methods, which allow read lengths of 500 nucleotides, were used for deep sequencing. Applicants first assessed heavy chain sequences from a 2008 PBMC sample from donor 45, the same time point from which antibodies VRC01, VRC02, and VRC03 were isolated by RSC3-probing of the memory B-cell population (18). mRNA from 5 million PBMC was used as the template for PCR to preferentially amplify the IgG and IgM genes from the IGHV1 family. The 454 pyrosequencing provided 221,104 sequences of which 33,386 encoded heavy chain variable domains that encompassed the entire V(D)J region (Appendix 1). To categorize the donor 45-heavy chain sequence information, Applicants chose characteristics particular to the heavy chains of VRC01 and VRC03 as filters: (i) sequence identity, (ii) IGHV gene allele origin, and (iii) sequence divergence from the germline IGHV-gene as a result of affinity maturation (FIG. 20B). Specifically, Applicants divided sequences into IGHV1-2*02 allelic origin (4,597 sequences) and non-IGHV1-2*02 origin (28,789 sequences), and analyzed divergence from inferred germline genes, and sequence identity to the template antibodies VRC01 and VRC03 (FIG. 20B). Interestingly, no sequence of higher than 75% identity to the VRC01 or VRC02 heavy chain was found (FIG. 20B), although 109 sequences of greater than 90% sequence identity to VRC03 were found and all were of IGHV1-2*02 origin. These heavy chain sequences formed a well segregated cluster on a contour plot (FIG. 20B, top middle panel). Applicants next assessed the biological function of two randomly selected heavy chain sequences from this cluster. Chimeric antibodies were made by pairing each of the two heavy chain sequences with the VRC03 light chain. In both cases, potent neutralization was observed, with neutralization similar to the original VRC03 antibody (FIG. 20E) (34).

Figure 20E:
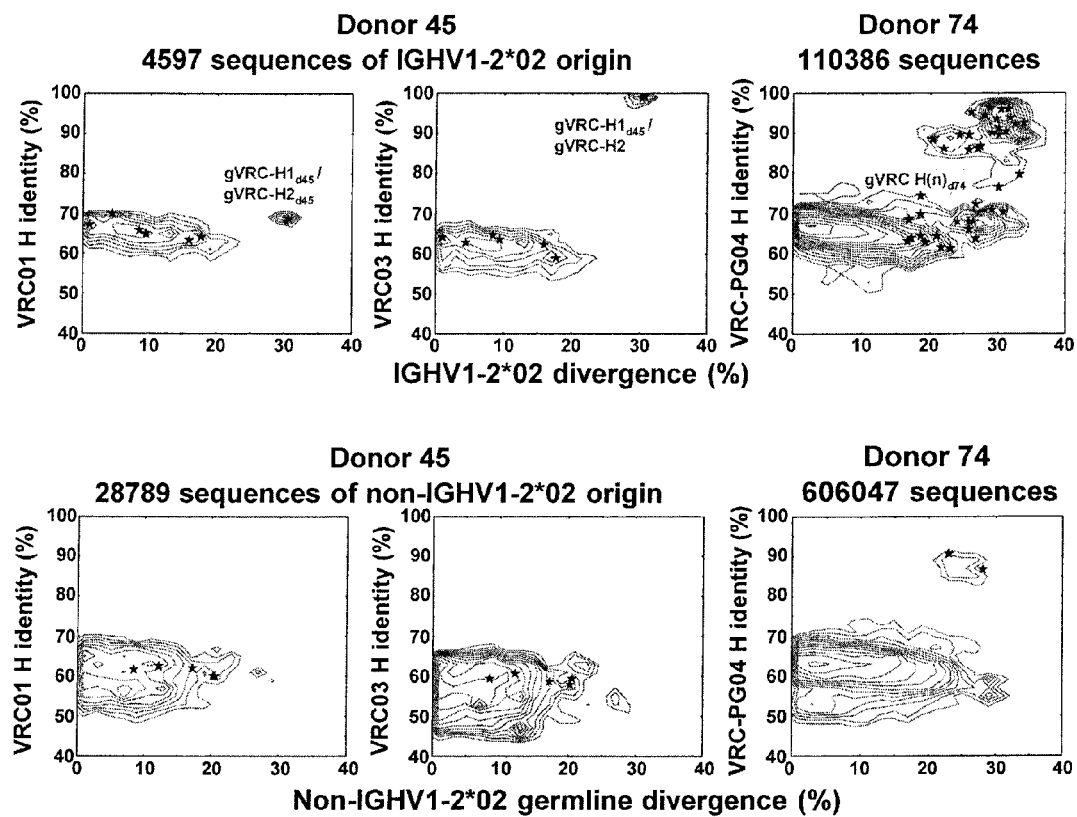

A similar heavy chain-deep sequencing analysis was performed with donor 74 PBMC from the same 2008 time point from which VRC-PG04 and VRC-PG04b were isolated. In the initial analysis, despite obtaining 263,764 sequences of which 85,851 encompassed the full V(D)J regions of the heavy chain and 93,112 were unique, no sequences of greater than 75% nucleotide identity to VRC-PG04 were found. Because the number of unique heavy chain mRNAs present in the PBMC sample was likely much larger than the number of unique sequences obtained in the initial analysis, Applicants repeated the deep sequencing of this sample with an increased number of 454 pyrosequencing reads and with protocols that optimized read length. In this analysis, 110,386 sequences of IGHV1-2*02 origin and 606,047 sequences of non-IGHV1-2*02-origin were found to encompass the V(D)J region of the heavy chain, a 10-fold increase in sequencing depth. Among these sequences, 4,920 displayed greater than 75% nucleotide identity to VRC-PG04 (FIG. 20B). Heavy chain sequences of the IGHV1-2*02 allelic origin segregated into several clusters, one at ~25% divergence and ~85% identity to the VRC-PG04 heavy chain, and several at 25-35% divergence and 65%, 85%, and 95% identity to VRC-PG04 (FIG. 20B, top right panel). To assess the biological function of these numerous 454-identified heavy chain sequences, Applicants selected 56 representative sequences from the quadrant defined by high divergence (16-38%) and high sequence similarity (60-100%) to VRC-PG04. The 56 sequences were synthesized and expressed with the VRC-PG04 light chain). Remarkably, many of these antibodies displayed potent HIV-1 neutralization (35), confirming that these were functional VRC-PG04-like heavy chains (FIG. 20E).

Applicants next performed a similar analysis of the antibody light chain. Because VRC01-03 and VRC-PG04 derive from IGκV3 alleles, Applicants used primers designed to amplify the IGκV3 gene family. Applicants chose a donor 45 2001 time point to maximize the likelihood of obtaining light chain sequences capable of functional complementation (36). A total of 305,475 sequences were determined of which 87,658 sequences encompassed the V-J region of the light chain (Appendix 4). To classify the donor 45-light chain sequences into useful subsets, Applicants again chose biologically specific characteristics: A distinctive 2-amino acid deletion in CDR L1 and high affinity maturation (17% and 19% for VRC01 and VRC-PG04, respectively). Two such sequences with ~90% sequence identity to the VRC01 and VRC03 light chains respectively, were identified (FIG. 20C). Applicants assessed the biological function of these two light chains after synthesis and expression in combination with the VRC01, VRC03, and VRC-PG04 heavy chains. When paired with their respective matching wild type heavy chain to produce a full IgG, both chimeric antibodies displayed neutralization similar to the wild type antibody (FIG. 20D).

Maturation Similarities of VRC01-Like Antibodies in Different Donors Revealed by Phylogenetic Tools.

Figure 21A:
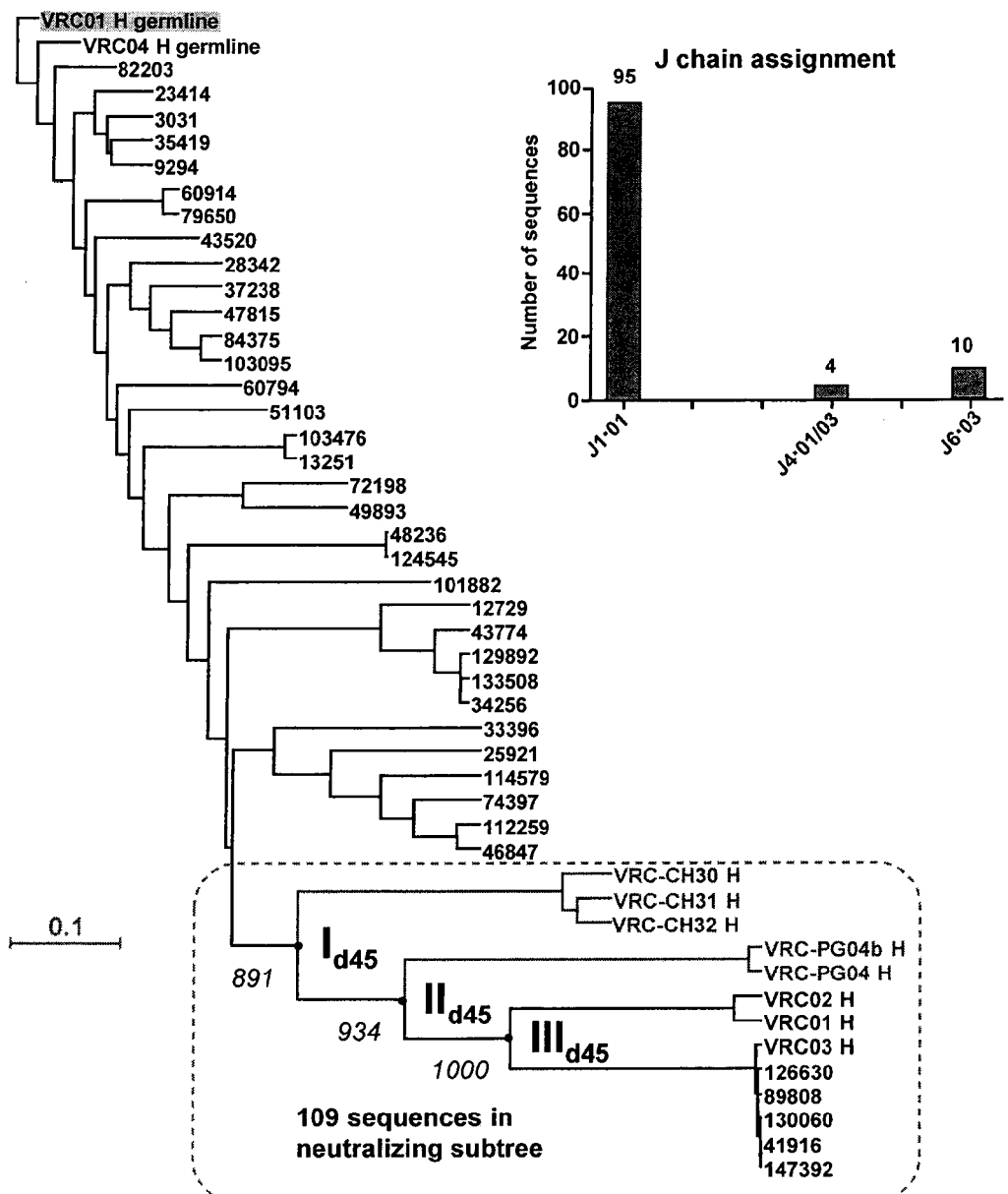

The structural convergence in gp120 recognition and the functional complementation between VRC01-like antibodies from different donors suggested similarities in their maturation processes. Applicants therefore used well-established phylogenetic tools to assess the evolutionary relationship among sequences derived from the same precursor germline gene (37). Applicants hypothesized that if known VRC01-like sequences from one donor were added to the analysis of sequences of another donor, the resultant 'cross-donor phylogenetic' analysis might reveal similarities in antibody maturation pathways. Specifically, with such an analysis, the exogenous sequences would be expected to interpose between dendrogram branches contain VRC01-like antibodies from the original donor's antibodyome. Applicants performed this analysis with heavy chains, as all of the probe-identified VRC01-like antibodies derived from the same heavy chain IGHV1-2*02 allele. Applicants added the donor 74-derived VRC-PG04 and 4b and donor 0219-derived VRC-CH30-32 heavy chain sequences to the donor 45 heavy chain sequences of IGHV1-2*02 genomic origin and constructed a tree rooted by the predicted VRC01-unmutated germline ancestor (18). This analysis revealed that sequences of high identity to VRC03 clustered as a subtree of a common node that was also the parent to donor 74 and 0219 VRC01-like heavy chain sequences (FIG. 21A, left). Two donor 45 sequences chosen at random from the subtree derived from this common node were shown to neutralize HIV-1, whereas 11 heavy chain sequences from outside this node did not neutralize (P<0.0001).

Figure 22A:
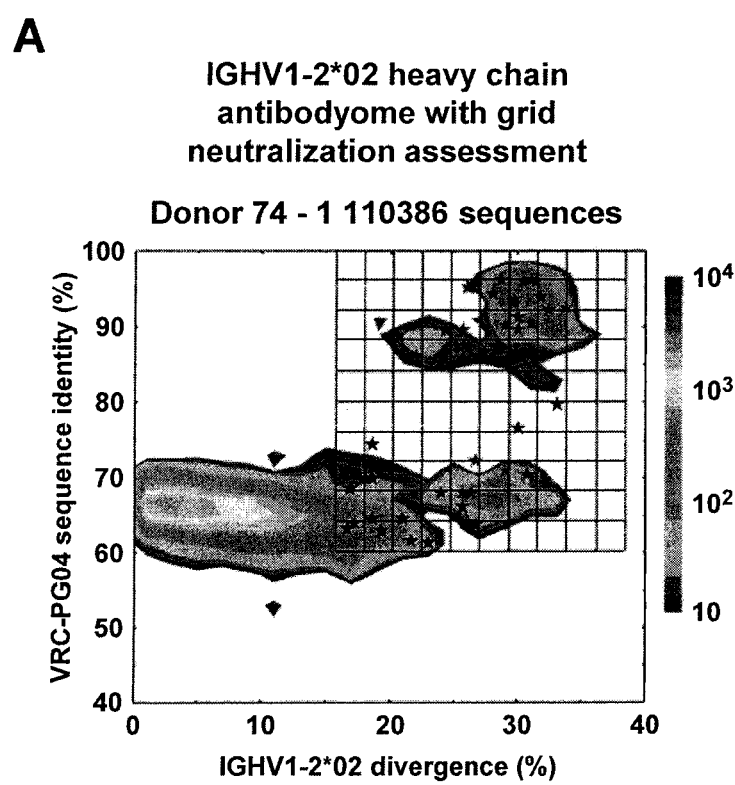
Figure 22B:
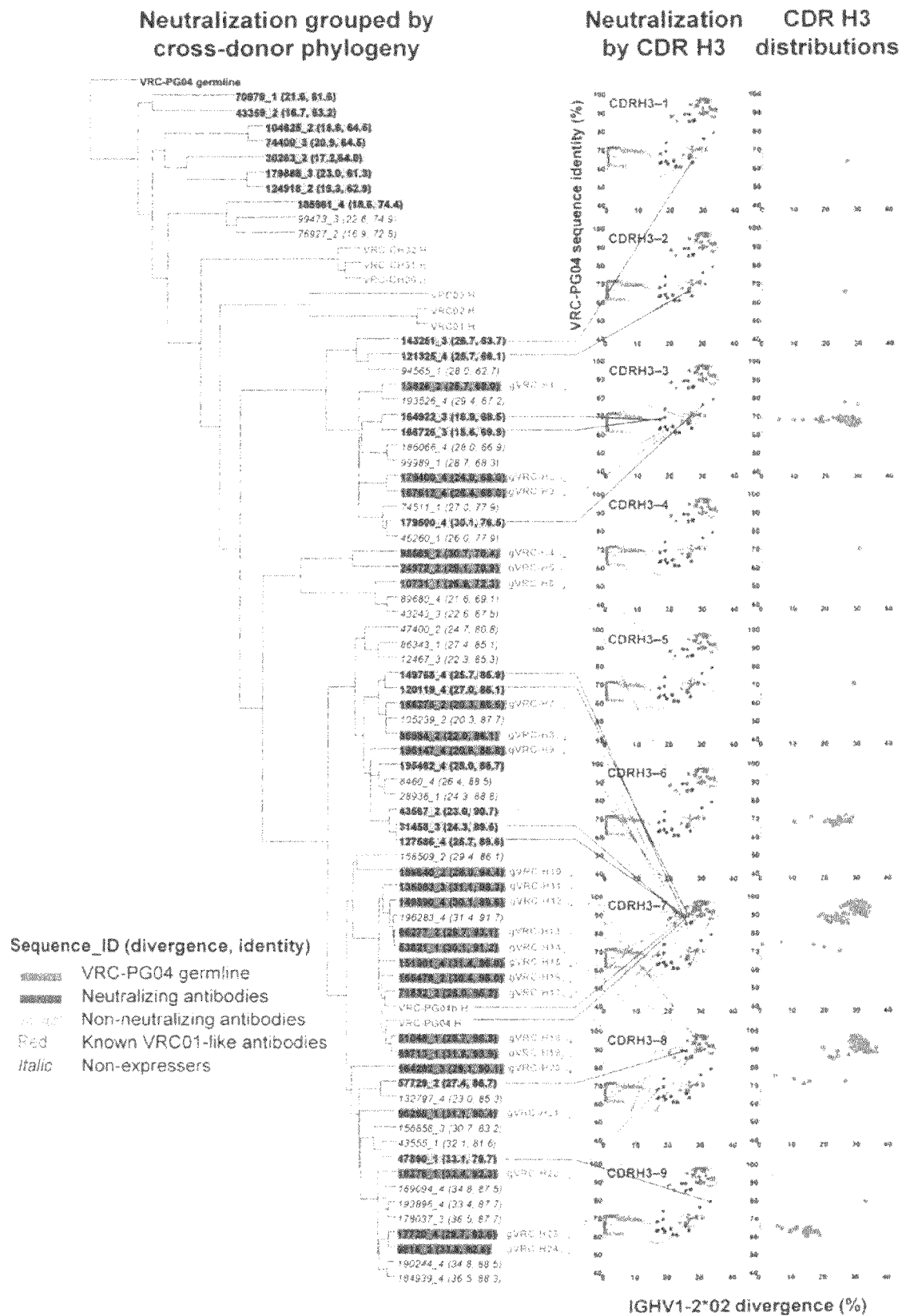

Applicants also assessed the donor 74-derived IGHV1-2*02 heavy chain sequences by including probe-identified VRC01-like antibodies from donor 45 and donor 0219 in the cross-donor phylogenetic analysis. In the tree rooted by the predicted VRC-PG04 unmutated germline ancestor, 5,047 sequences segregated within the donor 45 and 0219-identified subtree (FIG. 21A, right). This subtree included the actual VRC-PG04 and 04b heavy chain sequences, 4,693 sequences of >85% identity to VRC-PG04, and several hundred sequences with identities as low as 68% to VRC-PG04. To test the functional activity of heavy chain sequences identified by this analysis, Applicants first assessed the tree location of the 56 heavy chain sequences that were identified and expressed from the previously described identity/divergence grid (FIG. 22A). To these 56 sequences, Applicants added 7 additional sequences from the donor 74 tree and 7 non-IGHV1-2*02 sequences to enhance coverage of the cross-donor segregated sequences (FIG. 22B). These 70 sequences were synthesized and expressed with the VRC-PG04 light chain (FIG. 22C). Among these 70 synthesized heavy chain sequences, 25 did not express. Of the remaining 45 reconstituted antibodies, 24 were able to neutralize HIV-1 (FIG. 22B). Remarkably, all of the neutralizing sequences segregated into the subtree identified by the exogenously added donor 45 and 0219 VRC01-like antibodies (P-value=0.0067) (FIG. 22D).

Applicants also applied this cross-donor segregation method to the light chains antibodyome of donor 45. The light chains from donors 74 and 0219 did not segregate with known VRC01-like light chains from donor 45, likely because these three light chains do not arise from the same inferred germline sequences. This difference may also reflect the dissimilarities in focused maturation of the two chains (see FIG. 19A): in the heavy chain, focused maturation occurs in the CDR H2 region (encompassed solely within the IGHV1-2*02 $V_H$ gene from which all VRC01-like heavy chains derive) and, in the light chain, selection pressures occur in the CDR L3 region (which is a product of different types of V-J recombination).

CDR H3-Lineage Analysis.

The 37 heavy chain sequences that both segregated into the VRC01 neutralizing subtree and expressed when reconstituted with the VRC-PG04 light chain could be clustered into 9 CDR H3 classes (FIG. 22B), with sequences in each class containing no more than 5 nucleotide differences in CDR H3 from other sequences in the same class. A detailed junction analysis of the V(D)J recombination origins of these classes suggested that 8 of the 9 classes arose by separate recombination events; two of the classes (7 and 8) differed primarily by a single three-residue insertion deletion, Arg-Tyr-Ser, and may have arisen from a single V(D)J recombination event. Three of these classes (CDR H3-1, 2, and 9) were represented only by non-neutralizing antibodies, three by a single neutralizing antibody (CDR H3-4, 5 and 6), and three by a mixtures of neutralizing and non-neutralizing antibodies (CDR H3-3, 7 and 8) (38). Although it was not clear if the nonneutralizing heavy chain sequences truly lacked neutralization function or if this phenotype was due to incompatibilities in light chain pairing, Applicants chose to analyze CDR H3 classes only for those in which neutralization had been confirmed.

Applicants further analyzed donor 74 IGHV1-2*02 heavy chain sequences to provide an overview of CDR H3 diversity relative to sequence identity and divergence (FIG. 22E) and to identify those with CDR H3 sequences identical to the CDR H3s in each of the neutralizing classes. This analysis identified four clonal lineages (CDR H3-classes 3, 6, 7 and 8), with sequences that extended to 15% or less affinity maturation. CDR H3 class 7 included the probe-identified antibodies, VRC-PG04 and 04b (FIG. 22B). In each case, a steady accumulation of changes in both framework and CDR regions led to increased neutralization activity (39), and changes at positions 48, 52, 58, 69, 74, 82 and 94 in the V gene, among others, appeared to be selected in several lineages. Overall, more than 1,500 unique sequences could be classified into these four CDR H3 lineages. Although these CDR H3 lineages were inferred from a single timepoint, they likely provide insight into the specific maturation pathways by which the heavy chains of VRC01-like antibodies evolve from an initial unmutated recombinant to a broadly neutralizing antibody.

J Chain Analysis and Maturation Complexities.

Among the heavy chain VRC01-like sequences identified in donors 45 and 74, a significant skewing of J chain usage was observed (FIG. 21A): in donor 45, over 87% of the cross donor-segregated sequences utilize the IGHJ1*01 allele, and in donor 74, 99% of the segregated sequences utilize the IGHJ2*01 allele. This preferential heavy J chain usage does not appear to be a requirement for binding specificity; indeed, the use of the J1 allele in VRC01, the J2 allele in VRC-PG04, and the J4 allele in VRC-CH31 provide examples for the functional compatibility of at least three different IGHJ alleles in VRC01-like antibodies. In addition to preferential J chain usage, other complexities in the maturation process could be inferred from similarities in mature heavy chain genes and differences in CDR H3 sequence. In the absence of information on the natural pairing of heavy and light chains, the antibody maturation processes underlying these complexities is difficult to infer. Nevertheless, the deep sequencing data, with thousands of CDR H3-defined maturation intermediates, provide sufficient information to suggest that the maturation process may involve heavy chain revision or other mechanisms of B cell diversification (40, 41).

Antibody Genomics, HIV-1 Immunity, and Vaccine Implications.

Affinity maturation that focuses a developing antibody onto a conserved site of HIV-1 vulnerability provides a mechanism to achieve broad recognition of HIV-1 gp120. Such focused evolution may be common to broadly neutralizing antibodies that succeed in overcoming the immune evasion that protects HIV-1 gp120 from humoral recognition; the multiple layers of evasion may constrain or focus the development of nascent antibodies to particular pathways during maturation.

The structure-based genomics approach described provides tools for understanding antibody maturation. Applicants show how deep sequencing can be utilized to determine the repertoire of specific families of heavy and light chain sequences in HIV-1 infected individuals. These partial antibodyomes can then be interrogated for unusual properties in sequence, or in maturation, to identify antibodies for functional characterization. Applicants demonstrate three means of sieving a large database of antibody sequences: 1) by identity to a known mAb sequence and by divergence from putative germline (identity/divergence-grid analysis), 2) by cross-donor phylogenetic analysis of maturation pathway relationships, and 3) by CDR H3-lineage analysis. These three means of sieving can be deployed both iteratively or in combination (FIG. 22). An important aspect of Applicants' analyses was the functional characterization of selected sequences achieved through expression of and reconstitution with known VRC01-like heavy or light chains, although other means of pairing such as by frequency analysis (42) are possible. Although neutralization has been assessed on less than 100 reconstituted antibodies, the thousands of identified heavy and light chain sequences provide a large dataset for analysis, which should enhance Applicants' understanding of the critical features of VRC01-like antibodies. For example, the correlation of sequence variation at particular positions with neutralization should provide insight into the allowed diversity and required elements of neutralization by this family of antibodies.

Figure 21B:
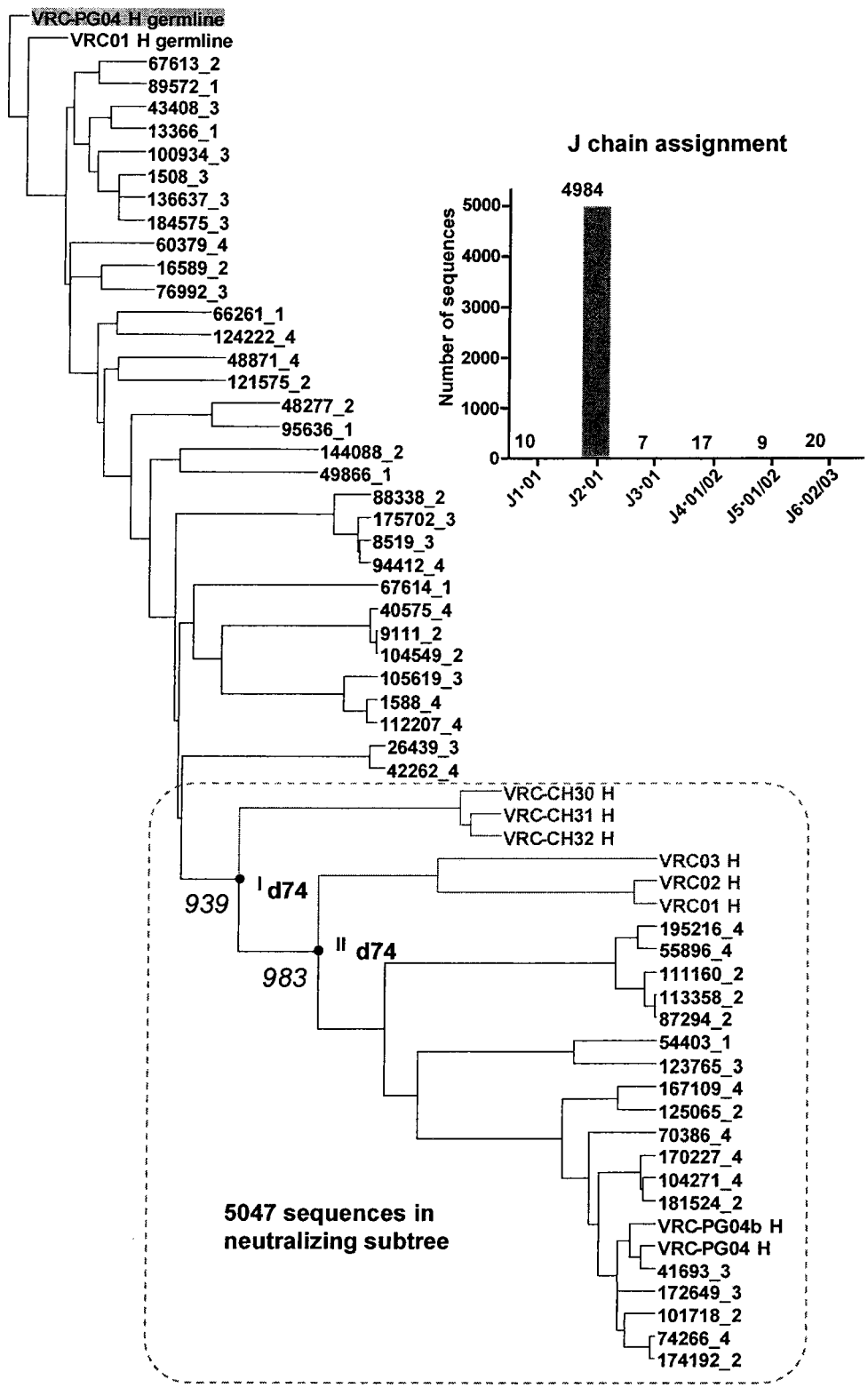

The deep sequencing and structural bioinformatics methodologies presented here facilitate analysis of the human antibodyome. This genomics technology allows interrogation of the antibody responses from infected donors, uninfected individuals, or even vaccine recipients and has several implications. For example, a genomic rooted analysis of the VRC01 antibodyome with standard phylogenetic tools may reveal a general B cell maturation pathway for the production of VRC01-like antibodies. Indeed, cross-donor phylogenetic analysis (FIG. 21B) suggests that common maturation intermediates with 20-30 affinity maturation changes from the IGHV1-2*02 genomic precursor are found in different individuals. These intermediates give rise to mature, broadly neutralizing VRC01-like antibodies, which have about 70-90 changes from the IGHV1-2*02 precursor (FIG. 21B). If modified gp120s with affinity to the maturation intermediates represented by the nodes of the tree were to stimulate the elicitation of these intermediates, then the analysis presented here can help guide the vaccine-induced elicitation of VRC01-like antibodies. Deep sequencing not only provides a means to identify such intermediates, but also a means to facilitate their detection. Overall, the application of genomic technologies to analysis of antibodies facilitates both highly sensitive feedback and an unprecedented opportunity to understand the response of the antibodyome to infection and vaccination.

REFERENCES AND NOTES IN THIS EXAMPLE

1. D. R. Burton et al., HIV vaccine design and the neutralizing antibody problem. *Nat Immunol* 5, 233-236 (2004).

2. R. Pantophlet, D. R. Burton, GP120: target for neutralizing HIV-1 antibodies. *Annu Rev Immunol* 24, 739-769 (2006).

3. P. D. Kwong et al., HIV-1 evades antibody-mediated neutralization through conformational masking of receptor-binding sites. *Nature* 420, 678-682 (2002).

4. L. Stamatatos, L. Morris, D. R. Burton, J. R. Mascola, Neutralizing antibodies generated during natural HIV-1 infection: good news for an HIV-1 vaccine? *Nat Med* 15, 866-870 (2009).

5. D. N. Sather et al., Factors associated with the development of cross-reactive neutralizing antibodies during human immunodeficiency virus type 1 infection. *J Virol* 83, 757-769 (2009).

6. M. D. Simek et al., Human immunodeficiency virus type 1 elite neutralizers: individuals with broad and potent neutralizing activity identified by using a high-throughput neutralization assay together with an analytical selection algorithm. *J Virol* 83, 7337-7348 (2009).

7. N. A. Doria-Rose et al., Breadth of human immunodeficiency virus-specific neutralizing activity in sera: clustering analysis and association with clinical variables. *J Virol* 84, 1631-1636 (2010).

8. S. Gnanakaran et al., Genetic signatures in the envelope glycoproteins of HIV-1 that associate with broadly neutralizing antibodies. *PLoS Comput Biol* 6, e1000955 (2010).

9. E. S. Gray et al., Antibody specificities associated with neutralization breadth in plasma from human immunodeficiency virus type 1 subtype C-infected blood donors. *J Virol* 83, 8925-8937 (2009).

10. T. Muster et al., A conserved neutralizing epitope on gp41 of human immunodeficiency virus type 1. *J Virol* 67, 6642-6647 (1993).

11. M. B. Zwick et al., Broadly neutralizing antibodies targeted to the membrane-proximal external region of human immunodeficiency virus type 1 glycoprotein gp41. *J Virol* 75, 10892-10905 (2001).

12. L. M. Walker et al., Broad and potent neutralizing antibodies from an African donor reveal a new HIV-1 vaccine target. *Science* 326, 285-289 (2009).

13. M. Bonsignori et al., Immunoregulation of HIV-1 broadly neutralizing antibody responses: deciphering maturation paths for antibody induction. *AIDS Res Hum Retroviruses* 26, A153 (2010).

14. A. Trkola et al., Human monoclonal antibody 2G12 defines a distinctive neutralization epitope on the gp120 glycoprotein of human immunodeficiency virus type 1. *J Virol* 70, 1100-1108. (1996).

15. L. M. Walker, et al., High through-put functional screening of activated B cells from 4 African elite neutralizers yields a panel of novel broadly neutralizing antibodies. *AIDS Res Hum Retroviruses* 26, A32 (2010).

16. D. R. Burton et al., Efficient neutralization of primary isolates of HIV-1 by a recombinant human monoclonal antibody. *Science* 266, 1024-1027 (1994).

17. D. Corti et al., Analysis of memory B cell responses and isolation of novel monoclonal antibodies with neutralizing breadth from HIV-1-infected individuals. *PLoS One* 5, e8805 (2010).

18. X. Wu et at, Rational design of envelope identifies broadly neutralizing human monoclonal antibodies to HIV-1. *Science* 329, 856-861 (2010).

19. T. Zhou et al., Structural basis for broad and potent neutralization of HIV-1 by antibody VRC01. *Science* 329, 811-817 (2010).

20. J. Wrammert et al., Broadly cross-reactive antibodies dominate the human B cell response against 2009 pandemic H1N1 influenza virus infection. *J Exp Med* 208, 181-193 (2011).

21. M. Huber et al., Very few substitutions in a germ line antibody are required to initiate significant domain exchange. *J Virol* 84, 10700-10707 (2010).

22. X. Xiao et al., Germline-like predecessors of broadly neutralizing antibodies lack measurable binding to HIV-1 envelope glycoproteins: implications for evasion of immune responses and design of vaccine immunogens. *Biochem Biophys Res Commun* 390, 404-409 (2009).

23. Materials and Methods are available as Supporting Material on Science Online.

24. J. F. Scheid et al., Broad diversity of neutralizing antibodies isolated from memory B cells in HIV-infected individuals. *Nature* 458, 636-640 (2009).

25. R. A. Lerner, Rare antibodies from combinatorial libraries suggests an S.O.S. component of the human immunological repertoire. *Mol Biosyst* 7, 1004-1012 (2011).

26. C. C. Huang et al., Structural basis of tyrosine sulfation and VH-gene usage in antibodies that recognize the HIV type 1 coreceptor-binding site on gp120. *Proc Natl Acad Sci USA* 101, 2706-2711 (2004).

27. C. Sabin et al., Crystal structure and size-dependent neutralization properties of HK20, a human monoclonal antibody binding to the highly conserved heptad repeat 1 of gp41. *PLoS Pathog* 6, e1001195 (2010).

28. F. Breden et al., Comparison of antibody repertoires produced by HIV-1 infection, other chronic and acute infections, and systemic autoimmune disease. *PLoS One* 6, e16857 (2011).

29. M. K. Gorny et al., Preferential use of the VH5-51 gene segment by the human immune response to code for antibodies against the V3 domain of HIV-1. *Mol Immunol* 46, 917-926 (2009).

30. L. Chen et al., Structural basis of immune evasion at the site of CD4 attachment on HTV-1 gp120. *Science* 326, 1123-1127 (2009).

31. Significant correlations were observed between rmsd of VRC01-like antibody interaction with gp120 and size of CDR interaction but not of surface area in general.

32. T. Zhou et al., Structural definition of a conserved neutralization epitope on HIV-1 gp120. *Nature* 445, 732-737 (2007).

33. The mRNA was extracted from 20 million PBMC, reverse transcribed with oligo (dT)12-18 (SEQ ID NO: 1), and a quarter of the resultant cDNA (equivalent to the transcripts of 5 million PBMC) was used as the template for PCR to preferentially amplify the IGHV1 gene family from both the IgG and IgM expressing cells. PCR products were gel purified and analyzed by 454 pyrosequencing.

34. Applicants also assessed 454-derived sequences for structural compatibility with the VRC01, VRC03, and VRC-PG04 gp120-complex crystal structures using a threading algorithm which assessed structural compatibility using the DFIRE statistical potential (43). None of the ten sequences with optimal DFIRE scores, nor those with high germline divergence of non-IGHV1-2*02 genomic origin displayed neutralization when reconstituted with the VRC01 light chain (FIG. 20E). Thus, sequence similarity, IGHV1-2*02 origin, and divergence all correlate with neutralization potential, but other factors such as predicted structural compatibility failed to identify VRC01-like antibodies.

35. Six of the reconstituted antibodies displayed a mean $IC_{50}$ of ~0.1 µg/ml, a level of potency similar to that observed with the original probe-identified VRC-PG04 antibodies.

36. 1) VRC03L does not complement well with other heavy chains; 2) VRC03 H was readily found among donor 45 2008 sequences; 3) VRC01 and VRC02 H were not found among donor 45 2008 sequences; 4) VRC01-03 were isolated from the memory B-cell population. Results 1-4 suggests that VRC03 came after VRC01; Applicants therefore choose a pre-2008 timepoint to maximize chances of obtaining light chains that allowed for functional complementation with known VRC01 heavy chains.

37. Although phylogenetic analysis is often used to study the evolution of a family of sequences and to understand the relationships between ancestral sequences and their descendants, Applicants appreciate that there are some unique aspects to antibody evolution. Due to the nature of activation-induced cytidine deaminase (AID) activity, antibodies accumulate mutations at hotspots (CDRs) and thus do not occur is a stochastic manner throughout the antibody genome. Also, the process of VDJ recombination introduces nucleotide insertions and deletions that alter germline DNA sequence. Applicants' goal here was to elucidate the ontogeny of recombined antibody sequences in order to identify intermediate sequences related to mature neutralizing antibodies. Applicants therefore used well established maximum likelihood phylogenetic algorithms to analyze antibody sequence data and to build rooted trees of antibody sequences that are derived from a common ancestor (i.e., same VH-germline gene).

38. Several of the non-neutralizing heavy chain sequences shown in the CDR H3 distribution of FIG. 22 are likely the result of PCR template switching. The single heavy chain depicted in the CDR H3 classes 1 contour plot contains an unique CDR H3, but with a V-gene that displays high similarity to class 3 sequences. The same observation occurs for the two sequences in class 2 contour plot. Also, the highly divergent (and outlier) sequence on the CDR H3 class 9 distribution plot contains the same CDR H3 as the other 140 class 9 sequences, but with a V-gene that closely matches sequences found in class 8. Because only a few of more than 1,500 unique sequences identified by CDR H3 analysis showed dissimilar V-genes and all of these appeared as single or double outliers, template switching can occur but appears to be rare. This rarity is also suggested by an analysis of 606,047 non-IGHV1-2*02 from donor 74 for sequences with the CDR H3s identified in FIG. 22B, which finds less than 100 sequences, of which the majority corresponds to the likely miss-assigned cluster in the non-IGHV1-2*02 sequence of donor 45 in FIG. 20, as described in note (44).

39. A similar accumulation of somatic mutations was shown (45) with the broadly neutralizing antibodies PG9 and PG16 to correlate with an increase in neutralization breadth and potency.

40. D. Nemazee, M. Weigert, Revising B cell receptors. *J Exp Med* 191, 1813-1817 (2000).

41. E. Edry, D. Melamed, Receptor editing in positive and negative selection of B lymphopoiesis. *J Immunol* 173, 4265-4271 (2004).

42. J. Glanville et al., Precise determination of the diversity of a combinatorial antibody library gives insight into the human immunoglobulin repertoire. *Proc Natl Acad Sci USA* 106, 20216-20221 (2009).

43. H. Zhou, Y. Zhou, Distance-scaled, finite ideal-gas reference state improves structure-derived potentials of mean force for structure selection and stability prediction. *Protein Sci* 11, 2714-2726 (2002).

44. The peak at ~25% IGHV1-2*02 divergence and 88% identity was also seen in the sequence plot for sequences of non-IGHV1-2*02 origin. Cross-donor and CDR H3 analyses shows that these putative non-IGHV1-2*02 derived sequences segregate with VRC01-like antibodies in dendrograms and have CDR H3s which are identical to confirmed VRC01-like antibodies, indicating that sequences in the non-IGHV1¬-2*02 cluster are likely miss-assigned and actually of IGHV1-2*02 origin.

45. M. Pancera et al., Crystal structure of PG16 and chimeric dissection with somatically related PG9: structure-function analysis of two quaternary-specific antibodies that effectively neutralize HIV-1. *J Virol* 84, 8098-8110 (2010).

46. E. A. Kabat, T. T. Wu, K. S. Gottesman, C. Foeller, Sequences of Proteins of Immunological Interest. 5th Edition (1991).

47. E. Krissinel, K. Henrick, Inference of macromolecular assemblies from crystalline state. *J Mol Biol* 372, 774-797 (2007).

48. Y. Li et al., Broad HIV-1 neutralization mediated by CD4-binding site antibodies. *Nat Med* 13, 1032-1034 (2007).

49. L. M. Walker et al., A limited number of antibody specificities mediate broad and potent serum neutralization in selected HIV-1 infected individuals. *PLoS Pathog* 6 (2010).

50. Y. Li et al., Analysis of neutralization specificities in polyclonal sera derived from human immunodeficiency virus type 1-infected individuals. *J Virol* 83, 1045-1059 (2009).

51. D. H. Barouch, G. J. Nabel, Adenovirus vector-based vaccines for human immunodeficiency virus type 1. *Hum Gene Ther* 16, 149-156 (2005).

52. T. Tiller et al., Efficient generation of monoclonal antibodies from single human B cells by single cell RT-PCR and expression vector cloning. *J Immunol Methods* 329, 112-124 (2008).

53. M. M. Souto-Carneiro, N. S. Longo, D. E. Russ, H. W. Sun, P. E. Lipsky, Characterization of the human Ig heavy chain antigen binding complementarity determining region 3 using a newly developed software algorithm, JOINSOLVER. *J Immunol* 172, 6790-6802 (2004).

54. X. Brochet, M. P. Lefranc, V. Giudicelli, IMGT/V-QUEST: the highly customized and integrated system for IG and TR standardized V-J and V-D-J sequence analysis. *Nucleic Acids Res* 36, W503-508 (2008).

55. S. Malcolm et al., Localization of Human Immunoglobulin κ Light Chain Variable Region Genes to the Short Arm of Chromosome 2 by in situ Hybridization. *Proc Natl Acad Sci USA* 79, 4957-4961 (1982).

56. M. Li et al., Human Immunodeficiency Virus Type 1 env Clones from Acute and Early Subtype B Infections for Standardized Assessments of Vaccine-Elicited Neutralizing Antibodies. *J Virol* 79, 10108-10125 (2005).

57. M. S. Seaman et al., Tiered categorization of a diverse panel of HIV-1 Env pseudoviruses for neutralizing antibody assessment. *J Virol* 84, 1439-1452 (2010).

58. X. Wu et al., Mechanism of human immunodeficiency virus type 1 resistance to monoclonal antibody B12 that effectively targets the site of CD4 attachment. *J Virol* 83, 10892-10907 (2009).

59. R. C. Edgar, MUSCLE: a multiple sequence alignment method with reduced time and space complexity. *BMC Bioinformatics* 5, 113 (2004).

60. R. C. Edgar, MUSCLE: multiple sequence alignment with high accuracy and high throughput. *Nucleic Acids Res* 32, 1792-1797 (2004).

61. D. T. Jones, W. R. Taylor, J. M. Thornton, The rapid generation of mutation data matrices from protein sequences. *Comput Appl Biosci* 8, 275-282 (1992).

62. M. K. Kuhner, J. Felsenstein, A simulation comparison of phylogeny algorithms under equal and unequal evolutionary rates. *Mol Biol Evol* 11, 459-468 (1994).

63. D. H. Huson et al., Dendroscope: An interactive viewer for large phylogenetic trees. *BMC Bioinformatics* 8, 460 (2007).

64. Z. Otwinowski, W. Minor, Processing of X-ray diffraction data collected in oscillation mode. *Methods in Enzymology* 276, 307-326 (1997).

65. A. J. McCoy et al., Phaser crystallographic software. *J Appl Crystallogr* 40, 658-674 (2007).

66. N. Collaborative Computational Project, The CCP4 suite: programs for protein crystallography. *Acta Crystallographica* Section D 50, 760-763 (1994).

67. P. D. Adams et al., PHENIX: building new software for automated crystallographic structure determination. *Acta Crystallographica* Section D 58, 1948-1954 (2002).

68. D. E. McRee, XtalView/Xfit—A versatile program for manipulating atomic coordinates and electron density. *J Struct Biol* 125, 156-165 (1999).

69. P. Emsley, K. Cowtan, Coot: model-building tools for molecular graphics. *Acta Crystallographica* Section D 60, 2126-2132 (2004).

70. I. W. Davis et al., MolProbity: all-atom contacts and structure validation for proteins and nucleic acids. *Nucleic Acids Res* 35, W375-383 (2007).

71. T. Lutteke, C. W. von der Lieth, pdb-care (PDB carbohydrate residue check): a program to support annotation of complex carbohydrate structures in PDB files. *BMC Bioinformatics* 5, 69 (2004).

72. A. Nicholls, K. A. Sharp, B. Honig, Protein folding and association: insights from the interfacial and thermodynamic properties of hydrocarbons. *Proteins* 11, 281-296 (1991).

73. N. A. Baker, D. Sept, S. Joseph, M. J. Hoist, J. A. McCammon, Electrostatics of nanosystems: application to microtubules and the ribosome. *Proc Natl Acad Sci USA* 98, 10037-10041 (2001).

74. W. L. DeLano, The PyMOL Molecular Graphics System. DeLano Scientific, San Carlos, Calif., USA (2002).

75. W. Brockman et al., Quality scores and SNP detection in sequencing-by-synthesis systems. *Genome Res* 18, 763-770 (2008).

76. M. A. Larkin et al., Clustal W and Clustal X version 2.0. *Bioinformatics* 23, 2947-2948 (2007).

77. D. Petrey et al., Using multiple structure alignments, fast model building, and energetic analysis in fold recognition and homology modeling. *Proteins* 53 Suppl 6, 430-435 (2003).

78. R. Chenna et al., Multiple sequence alignment with the Clustal series of programs. *Nucleic Acids Res* 31, 3497-3500 (2003).

79. S. F. Altschul et al., Gapped BLAST and PSI-BLAST: a new generation of protein database search programs. *Nucleic Acids Res* 25, 3389-3402 (1997).

80. S. Munshaw, T. B. Kepler, SoDA2: a Hidden Markov Model approach for identification of immunoglobulin rearrangements. *Bioinformatics* 26, 867-872 (2010).

81. G. E. Crooks, G. Hon, J. M. Chandonia, S. E. Brenner, WebLogo: a sequence logo generator. *Genome Res* 14, 1188-1190 (2004).

82. J. Zhu, H. Fan, Refining homology models by combining replica-exchange molecular dynamics and statistical potentials. *Proteins* 72, 1171-1188 (2008).

Support for this Example was provided by the Intramural Research Program of the Vaccine Research Center, National Institute of Allergy and Infectious Diseases and the National Human Genome Research Institute, National Institutes of Health, and by grants from the International AIDS Vaccine Initiative's Neutralizing Antibody Consortium and by the Center for HIV AIDS Vaccine Immunology Grant AI 5U19 AI 067854-06 from the National Institutes from Health. Use of sector 22 (Southeast Region Collaborative Access team) at the Advanced Photon Source was supported by the US Department of Energy, Basic Energy Sciences, Office of Science, under contract number W-31-109-Eng-38. Structure factors and coordinates for antibodies VRC03 and VRC-PG04 in complex with HIV-1 gp120 have been deposited with the Protein Data Bank under accession codes 3SE8 and 3SE9, respectively. Applicants have also deposited deep sequencing data for donors 45 and 74 used in this Example to NCBI Short Reads Archives (SRA) under accession number SRP006992, the heavy and light chain variable region sequences of probe-identified antibodies VRC-PG04 and VRC-PG04b (GenBank accession numbers JN159464-JN159467), VRC-CH30, VRC-CH31 and VRC-CH32 (JN159434-JN159439), and VRC-CH33 and VRC-CH34 (JN159470-159473), as well as the sequences of genomically identified neutralizers: 24 heavy chains from donor 74, 2008 (JN159440-JN159463), 2 heavy chains from donor 45, 2008 (JN159474-JN159475), 2 light chains from donor 45, 2001 (JN159468-JN159469), and 1,561 unique sequences associated with neutralizing CDR H3 distributions with at least one low divergent member (JN157873-JN159433).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated or non-naturally occurring human monoclonal antibody, wherein said monoclonal antibody neutralizes an HIV-1 virus in vitro, and further wherein the monoclonal antibody is selected from the group consisting of VRC-PG-04 or VRC-PG-05.

2. A diagnostic composition comprising a labeled antibody of claim 1, or a fragment thereof, to detect the presence of an HIV immunogen, antigen or epitope in a sample.

3. The composition of claim 2, wherein the sample is a biological sample.

4. The composition of claim 3, wherein the biological sample is blood, semen or vaginal fluid.

5. An isolated or non-naturally occurring VRC-PG-04 monoclonal antibody comprising a heavy chain sequence of SEQ ID NO: 6, 21 or 22 and a light chain sequence of SEQ ID NO: 14.

6. An isolated or non-naturally occurring variant of a VRC-PG-04 monoclonal antibody comprising a heavy chain sequence selected from SEQ ID NOS: 21 or 22 and a light chain sequence selected from SEQ ID NOS: 33 or 34.

7. A vector containing and expressing a nucleic acid encoding the VRC-PG-04 monoclonal antibody of claim 5.

8. A vector containing and expressing a nucleic acid encoding the VRC-PG-04 monoclonal antibody of claim 6.

* * * * *